United States Patent [19]

Takiguchi et al.

[11] Patent Number: 5,733,476
[45] Date of Patent: Mar. 31, 1998

[54] MESOMORPHIC COMPOUND, LIQUID CRYSTAL COMPOSITION, LIQUID CRYSTAL DEVICE, DISPLAY APPARATUS AND DISPLAY METHOD

[75] Inventors: Takao Takiguchi, Tokyo; Takashi Iwaki, Machida; Takeshi Togano, Yokohama; Yoko Yamada; Shinichi Nakamura, both of Isehara, all of Japan

[73] Assignee: Canon Kabushiki Kaisha, Tokyo, Japan

[21] Appl. No.: 609,055

[22] Filed: Feb. 29, 1996

Related U.S. Application Data

[63] Continuation of Ser. No. 196,752, Feb. 15, 1994, abandoned.

[30] Foreign Application Priority Data

Feb. 15, 1993 [JP] Japan ................ 5-025658

[51] Int. Cl.$^6$ .......... C09K 19/32; C09K 19/34; G02F 1/13; C07D 307/78
[52] U.S. Cl. ........... 252/299.62; 252/299.61; 252/299.63; 252/299.64; 252/299.65; 252/299.66; 252/299.67; 349/182; 549/462; 549/468; 549/469; 549/470
[58] Field of Search ............ 252/299.01, 299.61, 252/299.62, 299.63, 299.64, 299.65, 299.66, 299.67; 359/103; 349/182; 549/462, 468, 469, 470

[56] References Cited

U.S. PATENT DOCUMENTS

| | | | |
|---|---|---|---|
| 4,213,999 | 7/1980 | Witiak et al. | 424/285 |
| 4,367,924 | 1/1983 | Clark et al. | 350/334 |
| 5,091,109 | 2/1992 | Takiguchi et al. | 252/299.61 |
| 5,098,600 | 3/1992 | Nakamura et al. | 252/299.61 |
| 5,194,177 | 3/1993 | Nohira et al. | 252/299.61 |
| 5,213,709 | 5/1993 | Takiguchi et al. | 252/299.61 |
| 5,217,645 | 6/1993 | Iwaki et al. | 252/299.61 |
| 5,236,619 | 8/1993 | Iwaki et al. | 252/299.61 |
| 5,244,595 | 9/1993 | Yamada et al. | 252/299.61 |
| 5,284,599 | 2/1994 | Iwaki et al. | 252/299.61 |

FOREIGN PATENT DOCUMENTS

107216  8/1981  Japan.

OTHER PUBLICATIONS

CA 109: 91319, 1988.
CA 121: 218276, 1993.
Chemical Abstracts, vol. 94, No. 7 (Feb. 16, 1981) 47126.
Chemical Abstracts, vol. 94, No. 1 (Jan. 5, 1981) 3912a.
Chemical Abstracts, vol. 90, No. 17 (Apr. 23, 1979) 137661u.
Chemical Abstracts, vol. 112, No. 19 (May 7, 1990) 178875.
Patent Abstracts of Japan, vol. 7, No. 277 (Dec. 9, 1983) (C-199).
Takehara et al., "New Chiral Dopants for FLC Materials: Optically Active Cyclic Ethers", Ferroelectrics, vol. 148 (1993) pp. 195–202.
Schadt et al., App. Phys. Lett., vol. 18, No. 1 (1971) 127–8.
Gabert et al., Comptes Rendus Acad. Sci., vol. 235 (1952) 1407–8.
Davies et al., J. Chem. Soc., No. 624 (1950 pt. 4) 3195–201.
Hercouet et al., Tetra. Lett., No. 23 (1979) 2145–8.
Doad et al., Tetra. Lett., vol. 30, No. 13 (1989) 1597–8.
Toda et al., J. Org. Chem., vol. 55, No. 11 (1990) 3446–7.

*Primary Examiner*—Shean C. Wu
*Attorney, Agent, or Firm*—Fitzpatrick, Cella, Harper & Scinto

[57] ABSTRACT

A mesomorphic compound of the formula (I) having a coumaran skeleton is suitable as a component for a liquid crystal composition providing improved response characteristics. A liquid crystal device is constituted by disposing the liquid crystal composition between a pair of electrode plates. The liquid crystal device is used as a display panel constituting a display apparatus providing good display characteristics.

63 Claims, 4 Drawing Sheets

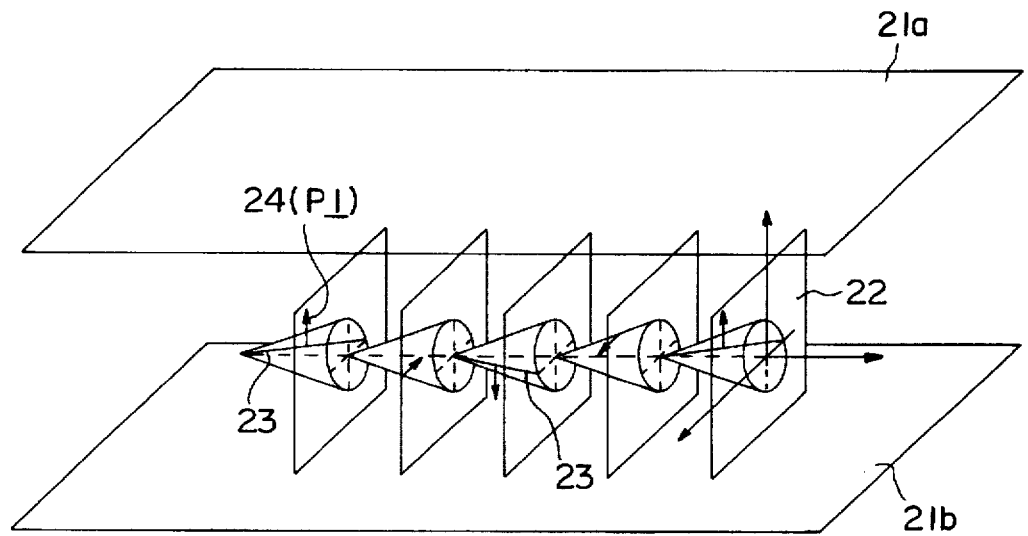
F I G. 2
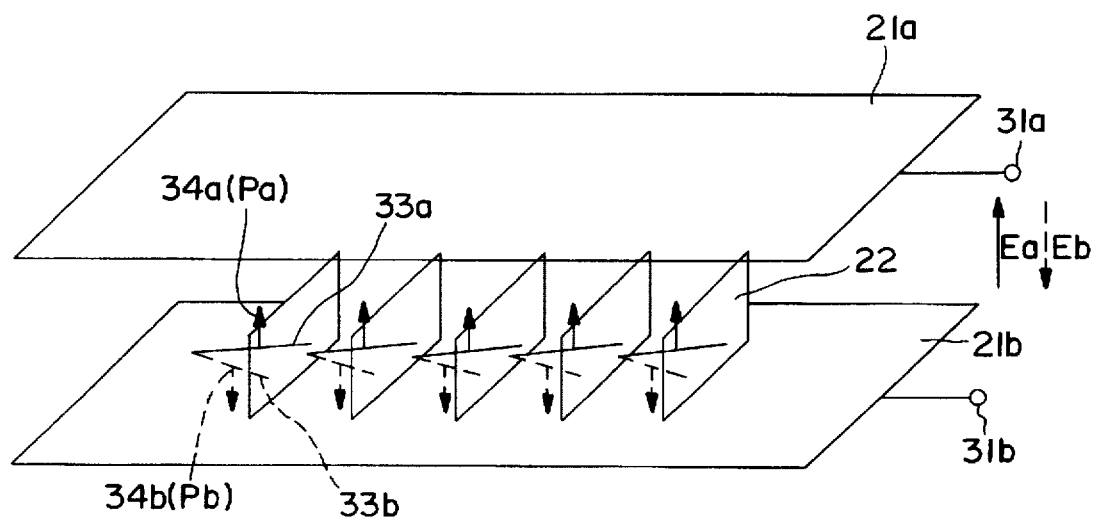
F I G. 3

MESOMORPHIC COMPOUND, LIQUID CRYSTAL COMPOSITION, LIQUID CRYSTAL DEVICE, DISPLAY APPARATUS AND DISPLAY METHOD

This application is a continuation of application Ser. No. 08/196,752, filed Feb. 15, 1994, now abandoned.

FIELD OF THE INVENTION AND RELATED ART

The present invention relates to a mesomorphic compound, a liquid crystal composition, a liquid crystal device, a display apparatus and a display method, and more particularly to a mesomorphic compound, a liquid crystal composition containing the mesomorphic compound with improved responsiveness to an electric field, a liquid crystal device using the liquid crystal composition for use in a display device, a liquid crystal-optical shutter, etc., a display apparatus using the device, and a display method of using the composition and device.

Hitherto, liquid crystal devices have been used as an electro-optical device in various fields. Most liquid crystal devices which have been put into practice use TN (twisted nematic) type liquid crystals, as shown in "Voltage-Dependent Optical Activity of a Twisted Nematic Liquid Crystal" by M. Schadt and W. Helfrich "Applied Physics Letters" Vol. 18, No. 4 (Feb. 15, 1971) pp. 127–128.

These devices are based on the dielectric alignment effect of a liquid crystal and utilize an effect that the average molecular axis direction is directed to a specific direction in response to an applied electric field because of the dielectric anisotropy of liquid crystal molecules. It is said that the limit of response speed is on the order of μsec, which is too slow for many uses. On the other hand, a simple matrix system of driving is most promising for application to a large-area flat display in view of cost, productivity, etc., in combination. In the simple matrix system, an electrode arrangement wherein scanning electrodes and signal electrodes are arranged in a matrix, and for driving, a multiplex driving scheme is adapted wherein an address signal is sequentially, periodically and selectively applied to the scanning electrodes and prescribed data signals are selectively applied in parallel to the signal electrodes in synchronism with the address signal.

When the above-mentioned TN-type liquid crystal is used in a device of such a driving system, a certain electric field is applied to regions where a scanning electrode is selected and signal electrodes are not selected (or regions where a scanning electrode is not selected and a signal electrode is selected), which regions are called "half-selected points". If the difference between a voltage applied to the selected points and a voltage applied to the half-selected points is sufficiently large, and a voltage threshold level required for allowing liquid crystal molecules to be aligned or oriented perpendicular to an electric field is set to a value therebetween, display devices normally operate. However, in fact, as the number (N) of scanning lines increases, a time (duty ratio) during which an effective electric field is applied to one selected point when a whole image area (corresponding to one frame) is scanned decreases with a ratio of 1/N. Accordingly, the larger the number of scanning lines are, the smaller is the voltage difference of an effective value applied to a selected point and non-selected points when scanning is repeatedly effected. This leads to unavoidable drawbacks of lowering of image contrast or occurrence of interference or crosstalk. These phenomena are regarded as essentially unavoidable problems appearing when a liquid crystal having no bistability (i.e. liquid crystal molecules are horizontally oriented with respect to the electrode surface as stable state and is vertically oriented with respect to the electrode surface only when an electric field is effectively applied) is driven (i.e. repeatedly scanned) by making use of a time storage effect. To overcome these drawbacks, the voltage averaging method, the two-frequency driving method, the multiple matrix method, etc. has been already proposed. However, any method is not sufficient to overcome the above-mentioned drawbacks. As a result, the development of large image area or high packaging density in respect to display elements is delayed because it is difficult to sufficiently increase the number of scanning lines.

To overcome drawbacks with such prior art liquid crystal devices, the use of liquid crystal devices having bistability has been proposed by Clark and Lagerwall (e.g. Japanese Laid-Open Patent Appln. No. 56-107216; U.S. Pat. No. 4,367,924, etc.). In this instance, as the liquid crystals having bistability, ferroelectric liquid crystals having chiral smectic C-phase (SmC*) or H-phase (SmH*) are generally used. These liquid crystals have bistable states of first and second stable states with respect to an electric field applied thereto. Accordingly, as different from optical modulation devices in which the above-mentioned TN-type liquid crystals are used, the bistable liquid crystal molecules are oriented to first and second optically stable states with respect to one and the other electric field vectors, respectively. Further, this type of liquid crystal has a property (bistability) of assuming either one of the two stable states in response to an applied electric and retaining the resultant state in the absence of an electric field.

In addition to the above-described characteristic of showing bistability, such a ferroelectric liquid crystal (hereinafter sometimes abbreviated as "FLC") has an excellent property, i.e., a high-speed responsiveness. This is because the spontaneous polarization of the ferroelectric liquid crystal and an applied electric field directly interact with each other to induce transition of orientation states. The resultant response speed is faster than the response speed due to the interaction between dielectric anisotropy and an electric field by 3 to 4 digits.

Thus, a ferroelectric liquid crystal potentially has very excellent characteristics, and by making use of these properties, it is possible to provide essential improvements to many of the above-mentioned problems with the conventional TN-type devices. Particularly, the application to a high-speed optical shutter and a display of a high density end a large picture is expected. For this reason, there has been made extensive research with respect to liquid crystal materials showing ferroelectricity. However, previous ferroelectric liquid crystal materials do not sufficiently satisfy characteristics required for a liquid crystal device including low-temperature operation characteristic, high-speed responsiveness, etc.

More specifically, among a response time $\tau$, the magnitude of spontaneous polarization Ps and viscosity $\eta$, the following relationship (II) exists: $\tau = \eta/(Ps \cdot E) \ldots$ (II), where E is an applied voltage. Accordingly, a high response speed can be obtained by (a) increasing the spontaneous polarization Ps, (b) lowering the viscosity $\eta$, or (c) increasing the applied voltage E. However, the driving voltage has a certain upper limit in view of driving with IC, etc., and should desirably be as low as possible. Accordingly, it is actually necessary to lower the viscosity or increase the spontaneous polarization.

A ferroelectric chiral smectic liquid crystal having a large spontaneous polarization generally provides a large internal electric field in a cell given by the spontaneous polarization and is liable to pose many constraints on the device construction giving bistability. Further, an excessively large spontaneous polarization is liable to accompany an increase in viscosity, so that remarkable increase in response speed may not be attained as a result.

Moreover, if it is assumed that the operation temperature of an actual display device is 5°–40° C., the response speed changes by a factor of about 20, so that it actually exceeds the range controllable by driving voltage and frequency.

Thus, as described hereinabove, commercialization of a ferroelectric liquid crystal device requires a liquid crystal composition assuming a chiral smectic phase which has a low viscosity, a high-speed responsiveness and a small temperature-dependence of response speed.

In order to afford uniform switching characteristics at display, a good view-angle characteristic, a good storage stability at a low temperature, a decrease in a load to a driving IC (integrated circuit), etc. to the above-mentioned ferroelectric liquid crystal device or a display apparatus including the ferroelectric liquid crystal device, the above-mentioned liquid crystal composition is required to optimize its properties such as spontaneous polarization, an chiral smectic C (SmC*) pitch, a cholesteric (Ch) pitch, a temperature range showing a mesomorphic phase, optical anisotropy, a tilt angle and dielectric anisotropy.

SUMMARY OF THE INVENTION

An object of the present invention is to provide a mesomorphic compound having a low viscosity, a high speed responsiveness and a decreased temperature-dependence of response speed; a liquid crystal composition, particularly a chiral smectic liquid crystal composition containing the mesomorphic compound for providing a practical ferroelectric liquid crystal device as described above; a liquid crystal device including the liquid crystal composition and affording a Good switching, a low-temperature operation and an improved temperature-dependence of response speed; a display apparatus including the device; and a display method of using the composition and device.

According to the present invention, there is provided a mesomorphic compound represented by the following formula (I):

$$R_1-A_1-X_1-A_2-X_2-A_3-R_2 \qquad (I),$$

wherein $R_1$ and $R_2$ independently denote hydrogen, halogen, —CN,

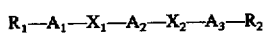

or a linear or branched alkyl group having 1–18 carbon atoms capable of including one or non-neighboring two or more —CH$_2$— groups which can be replaced with —O—, —S—,

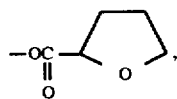

—CH=CH— or —C≡C—; said linear or branched alkyl group being capable of including hydrogen which can be replaced with fluorine;

$X_1$ and $X_2$ independently denote a single bond,

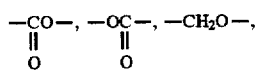

—OCH$_2$—, —CH$_2$CH$_2$— or —C≡C—;

$A_1$, $A_2$ and $A_3$ independently denote a single bond,

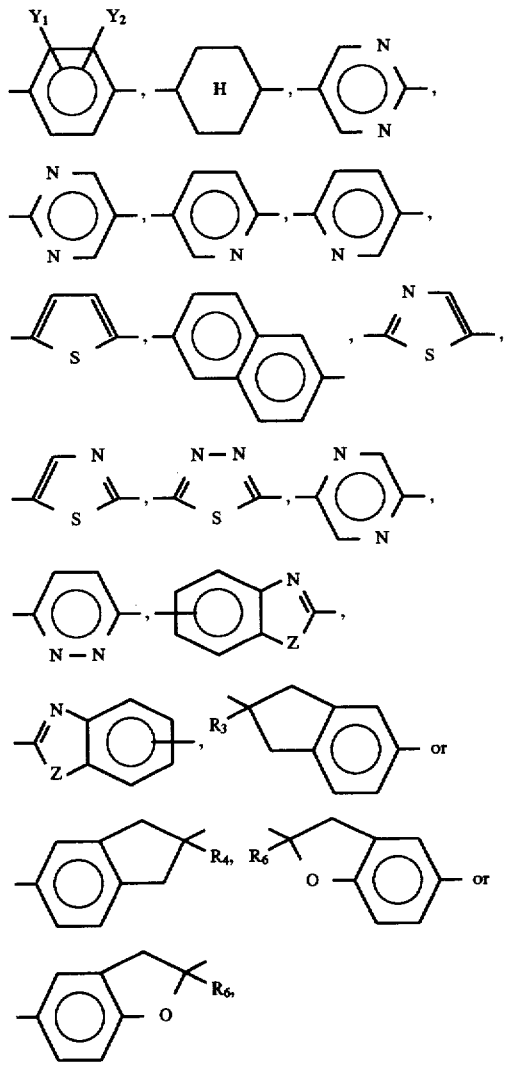

wherein $R_3$, $R_4$, $R_5$ and $R_6$ independently denote hydrogen, halogen or a linear or branched alkyl group having 1–18 carbon atoms; $Y_1$ and $Y_2$ independently denote H, F, Cl, Br, —CH$_3$, —CF$_3$ or —CN; Z denotes O or S; and at least one group of $A_1$, $A_2$ and $A_3$ is

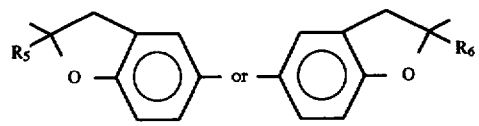

and the remaining two groups of $A_1$, $A_2$ and $A_3$ cannot be a single bond simultaneously.

According to the present invention, there is further provided a liquid crystal composition containing at least one species of the above-mentioned mesomorphic compounds.

The present invention provides a liquid crystal device comprising a pair of electrode plates and the liquid crystal composition described above disposed between the electrode plates.

The present invention further provides a display apparatus comprising the liquid crystal device, and voltage application means for driving the liquid crystal device.

The present invention still further provides a display method using the liquid crystal composition or the liquid crystal device described above and switching the alignment direction of liquid crystal molecules by applying voltages to the liquid crystal composition to effect display.

We have found that a mesomorphic compound represented by the formula (I) having at least one coumaran skeleton is suitable as a component of a liquid crystal composition, particularly a ferroelectric chiral smectic liquid crystal composition and a liquid crystal device including the liquid crystal composition which provide good display characteristics based on improvements in various characteristics such as an alignment characteristic, high speed responsiveness, and a temperature-dependence of response speed. As the mesomorphic compound of the formula (I) according to the present invention has a good compatibility with another (mesomorphic) compound used herein, it is possible to use the mesomorphic compound of the formula (I) for controlling various properties such as spontaneous polarization, SmC* pitch, Ch pitch, a temperature range showing a mesomorphic phase, optical anisotropy, a tilt angle and dielectric anisotropy, as to a liquid crystal mixture or composition.

These and other objects, features and advantages of the present invention will become more apparent upon a consideration of the following description of the preferred embodiments of the present invention taken in conjunction with the accompanying drawings.

BRIEF DESCRIPTION OF THE DRAWINGS

FIGS. 2 and 3 are schematic perspective views of a device cell embodiment for illustrating the operation principle of a liquid crystal device utilizing ferroelectricity of a liquid crystal composition;

DETAILED DESCRIPTION OF THE INVENTION

Figure 1:
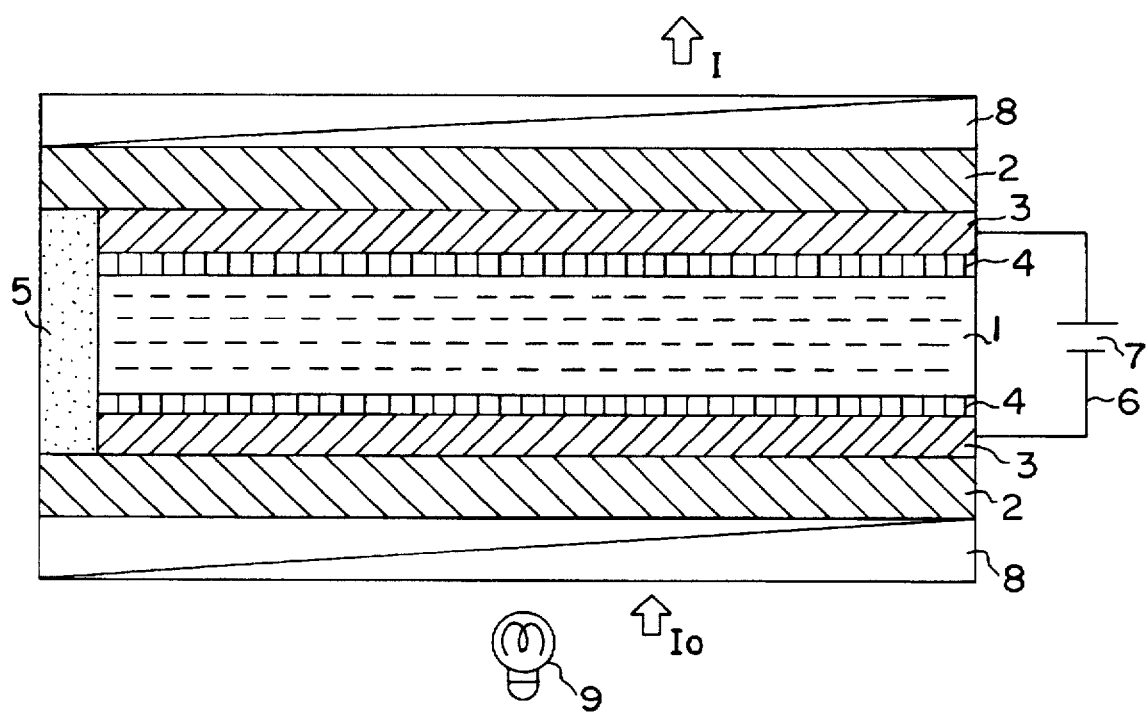
FIG. 1 is a schematic sectional view of a liquid crystal display device using a liquid crystal composition assuming a chiral smectic phase.

Preferred examples of the mesomorphic compound of the formula (I) may include those of the following formulas (Ia) to (It):

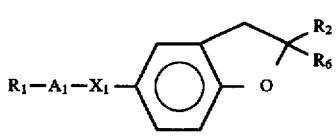

(Ia)

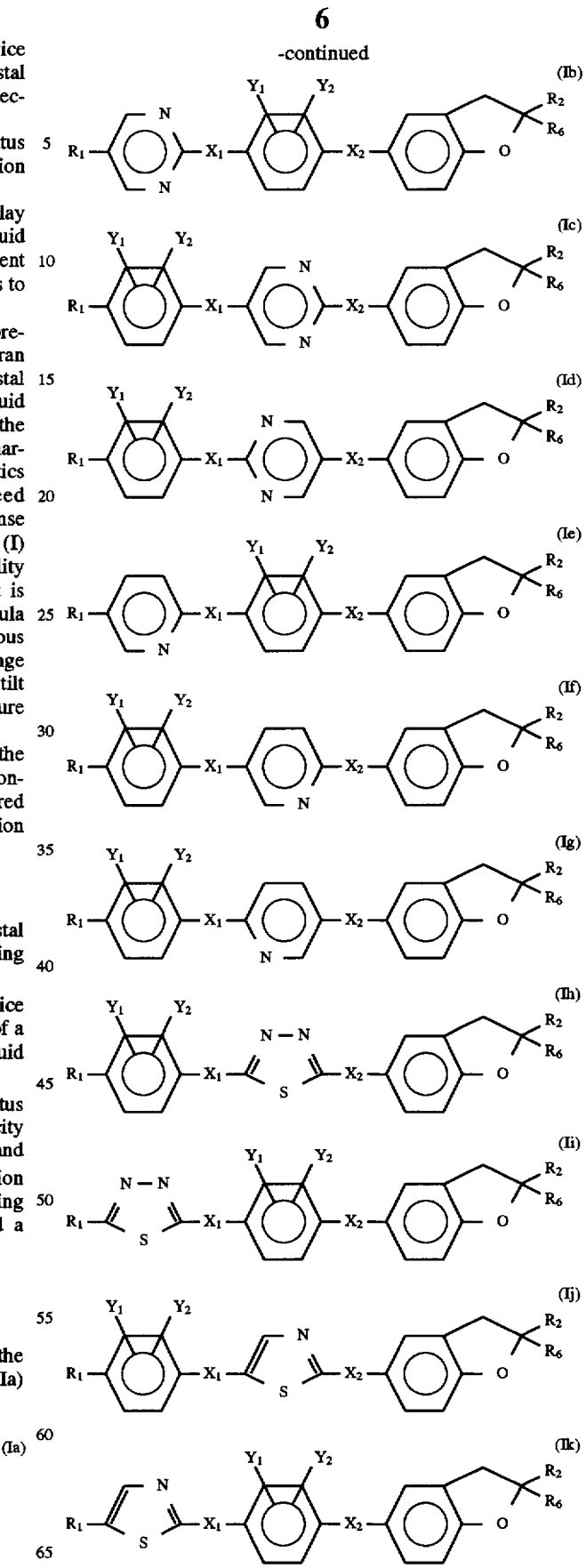

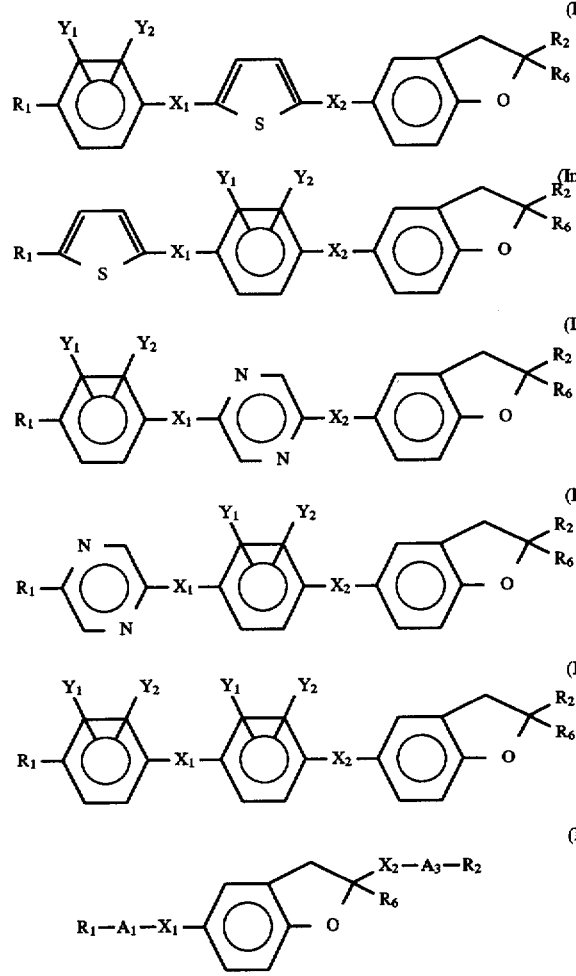
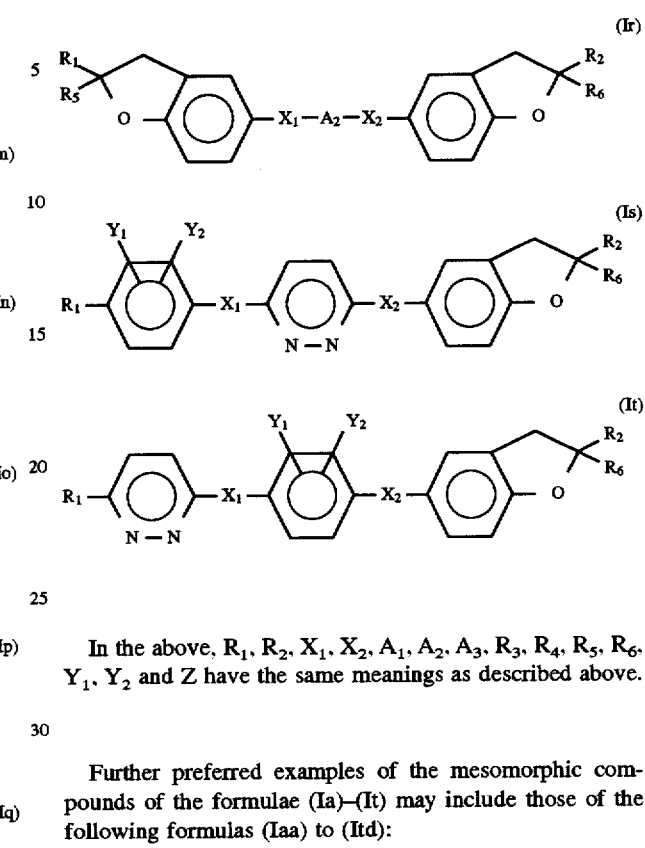
In the above, $R_1$, $R_2$, $X_1$, $X_2$, $A_1$, $A_2$, $A_3$, $R_3$, $R_4$, $R_5$, $R_6$, $Y_1$, $Y_2$ and Z have the same meanings as described above.
Further preferred examples of the mesomorphic compounds of the formulae (Ia)–(It) may include those of the following formulas (Iaa) to (Itd):
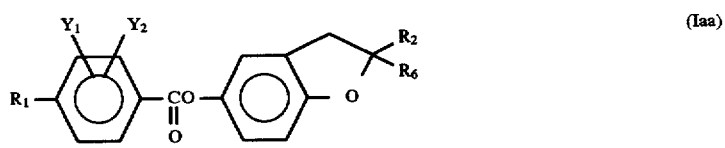
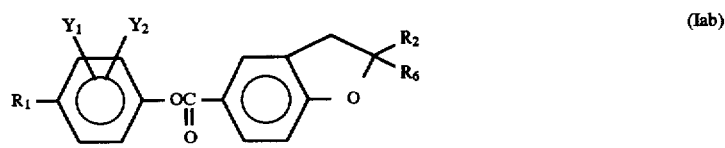
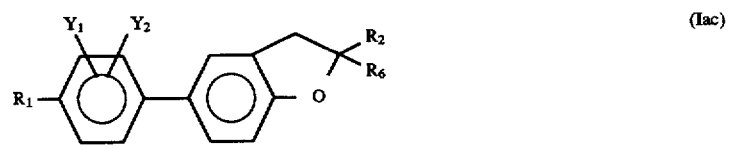
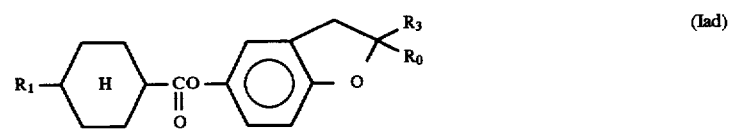

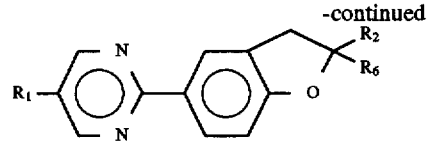(Iae)
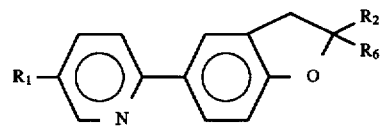(Iaf)
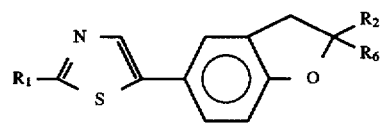(Iag)
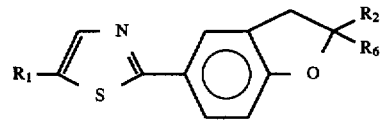(Iah)
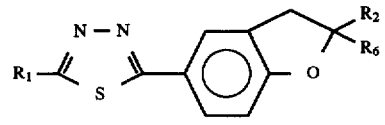(Iai)
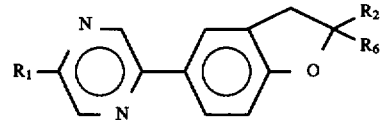(Iaj)
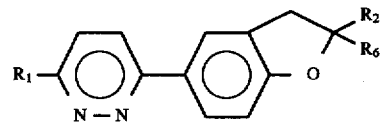(Iak)
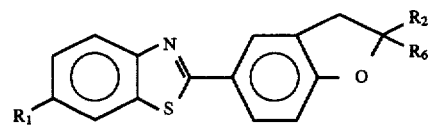(Ial)
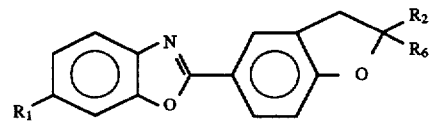(Iam)
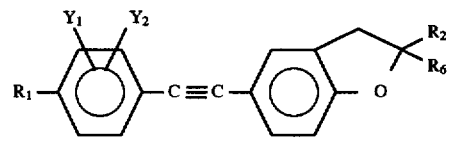(Ian)
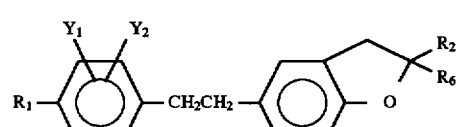(Iao)
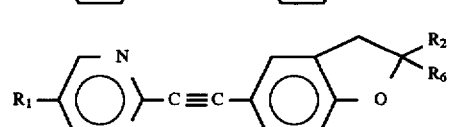(Iap)

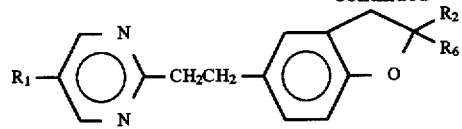
(Iaq)
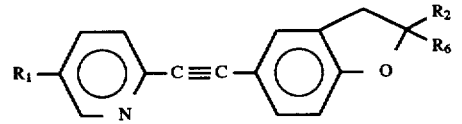
(Iar)
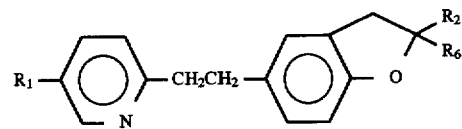
(Ias)
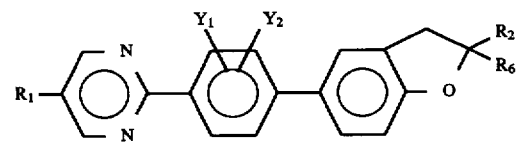
(Iba)
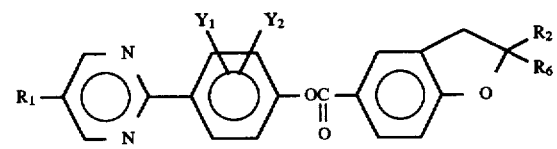
(Ibb)
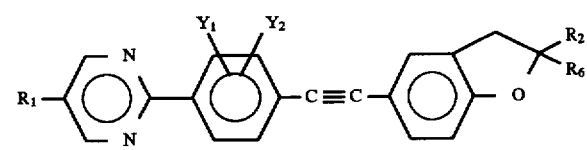
(Ibc)
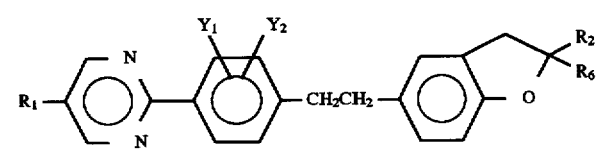
(Ibd)
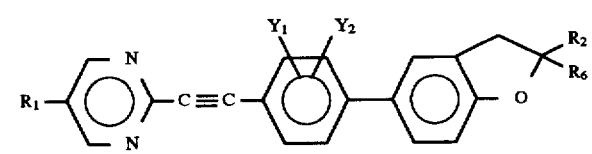
(Ibe)
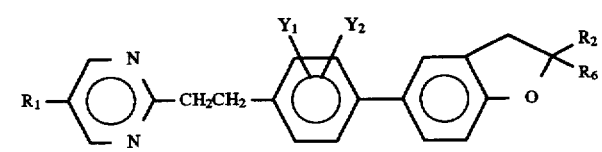
(Ibf)
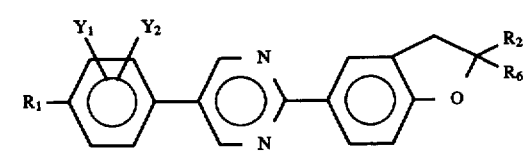
(Ica)
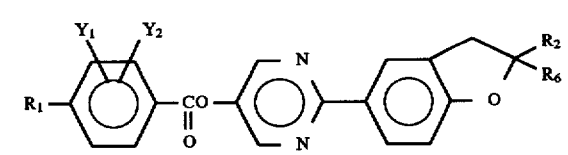
(Icb)

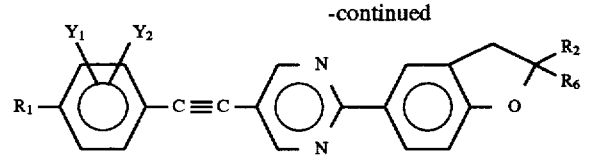
(Icc)
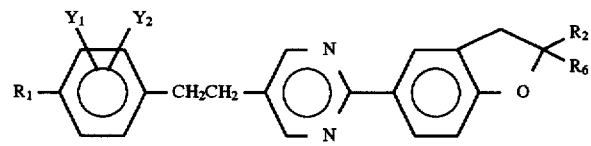
(Icd)
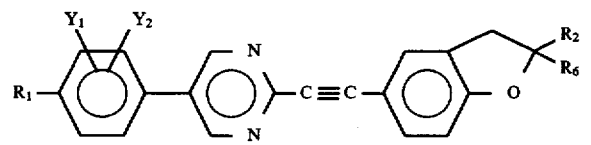
(Ice)
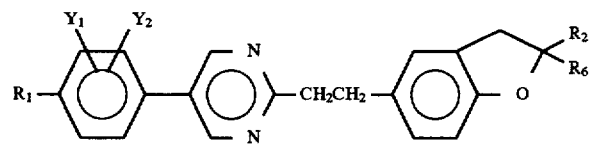
(Icf)
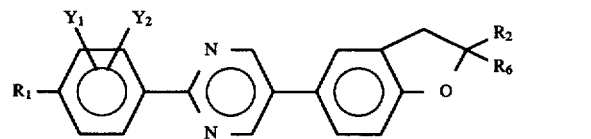
(Ida)
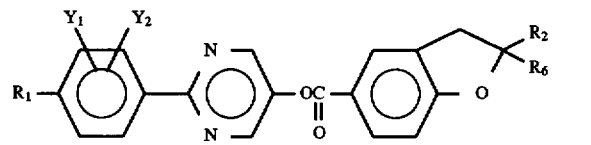
(Idb)
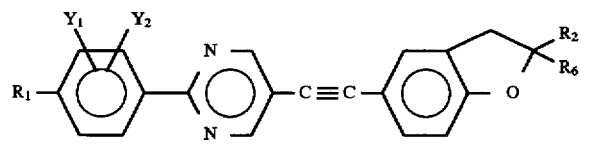
(Idc)
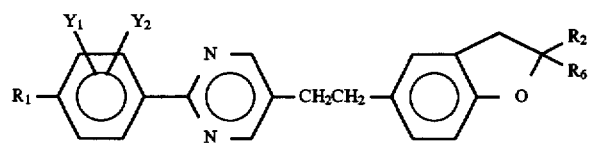
(Idd)
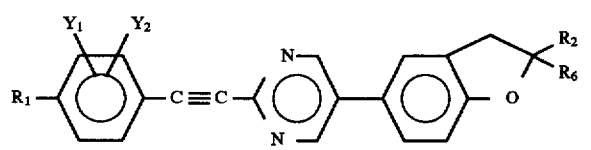
(Ide)
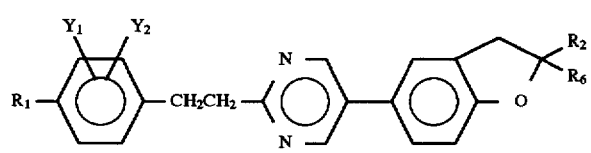
(Idf)
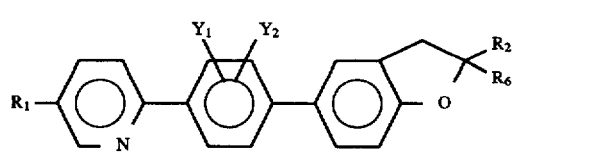
(Iea)

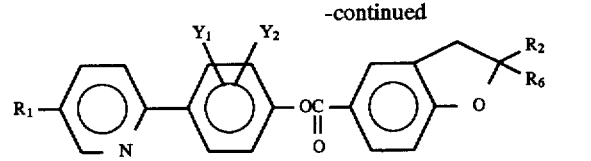 (Ieb)
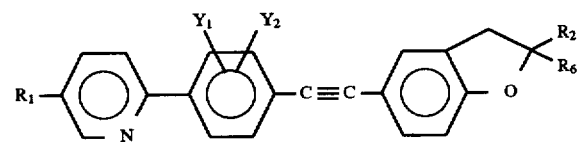 (Iec)
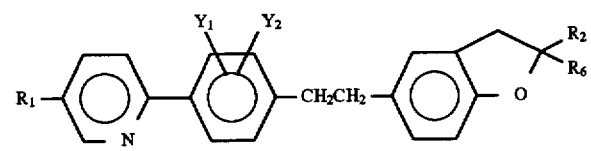 (Ied)
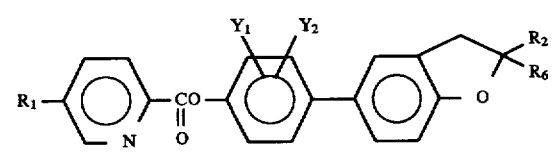 (Iee)
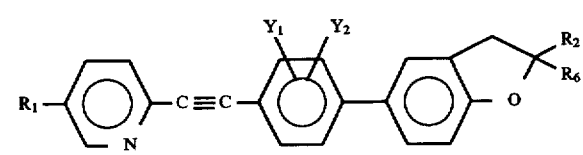 (Ief)
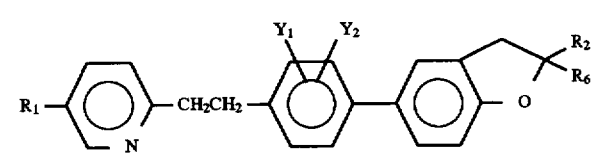 (Ieg)
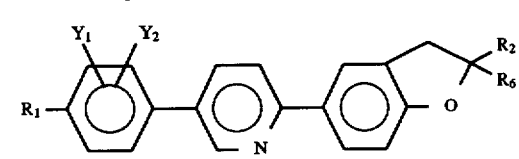 (Ifa)
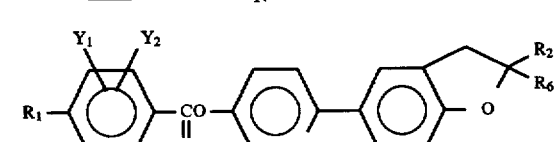 (Ifb)
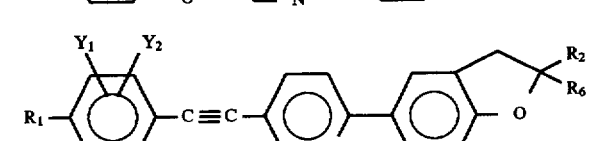 (Ifc)
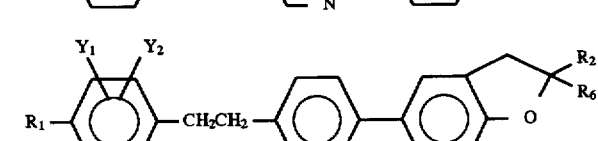 (Ifd)
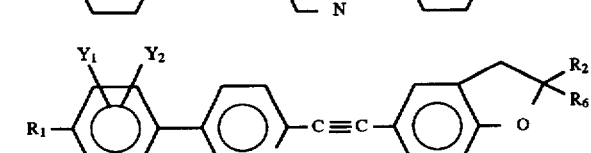 (Ife)

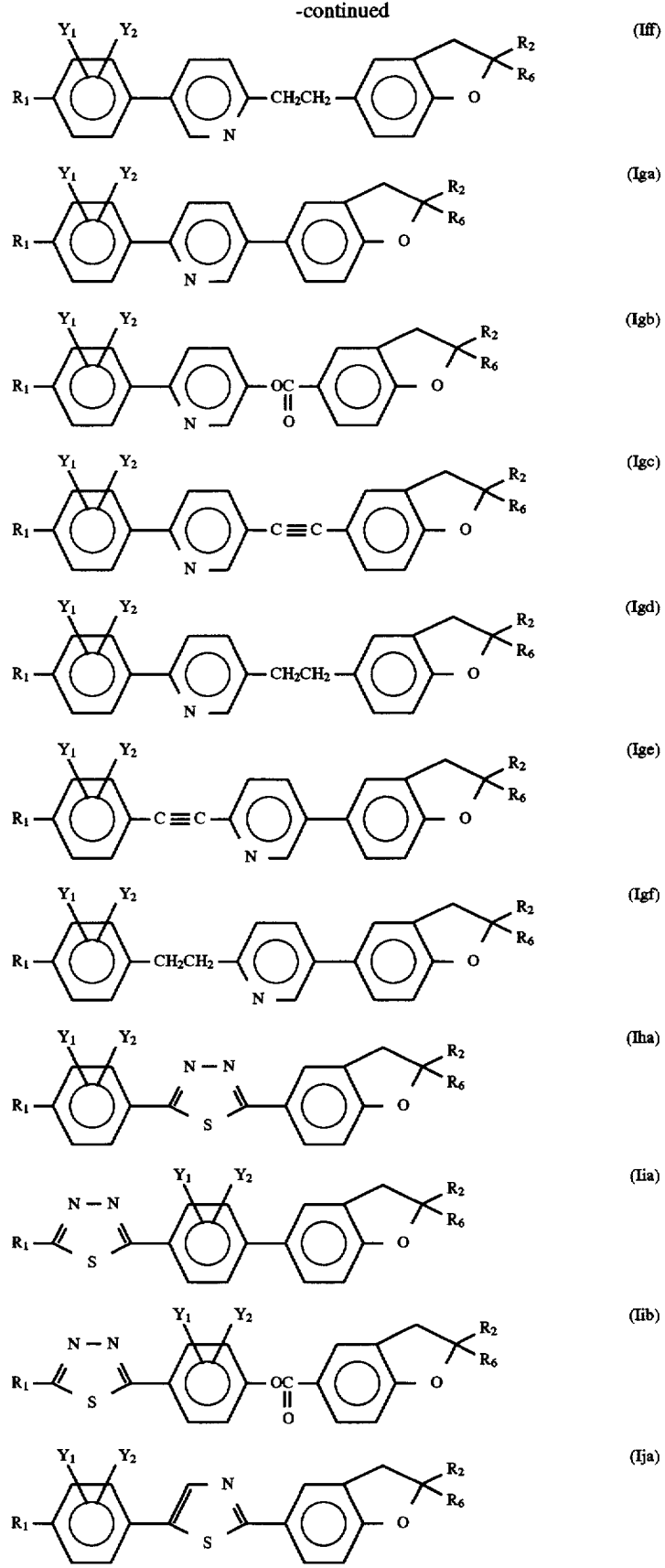

-continued
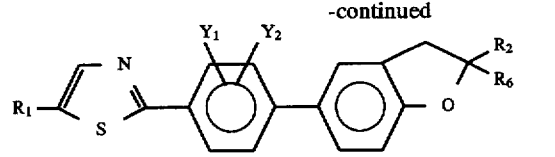 (Ika)
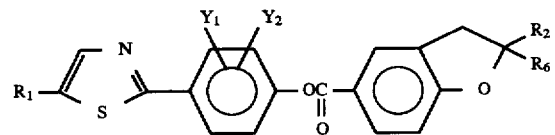 (Ikb)
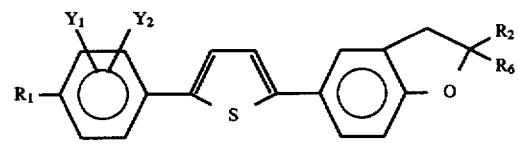 (Ila)
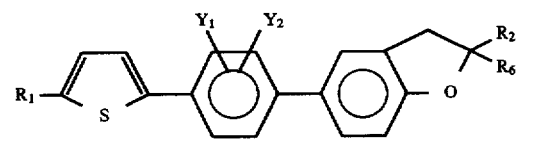 (Ima)
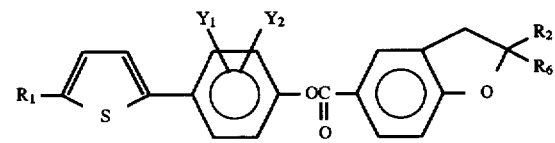 (Imb)
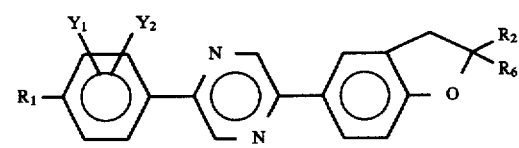 (Ina)
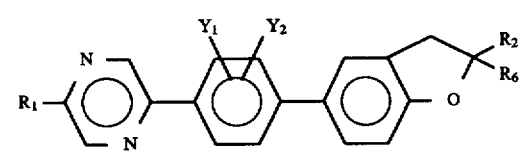 (Ioa)
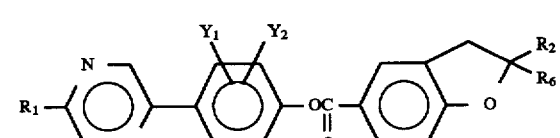 (Iob)
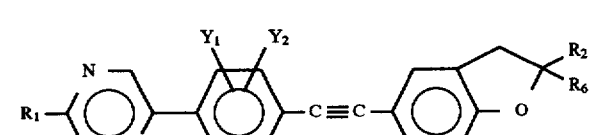 (Ioc)
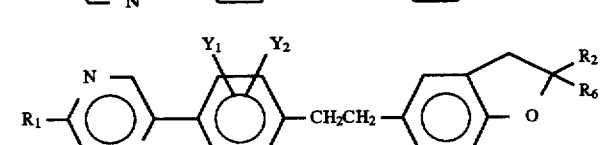 (Iod)
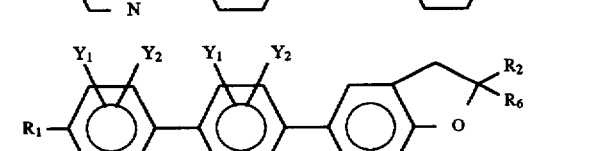 (Ipa)

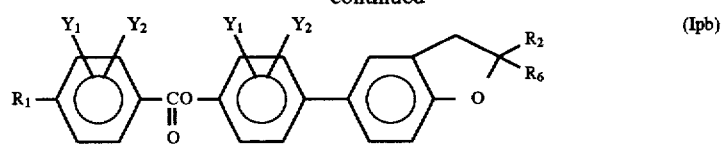
(Ipb)
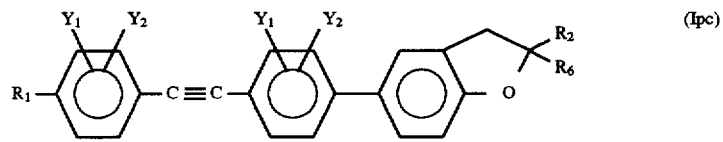
(Ipc)
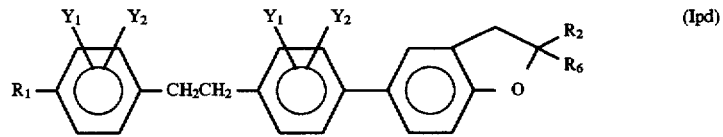
(Ipd)
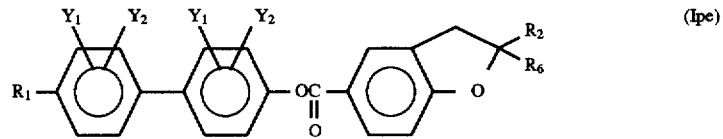
(Ipe)
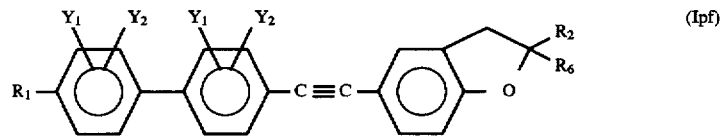
(Ipf)
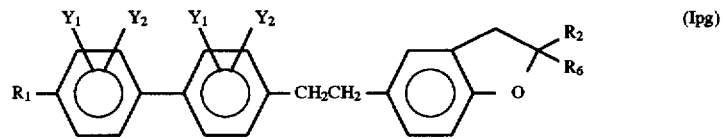
(Ipg)
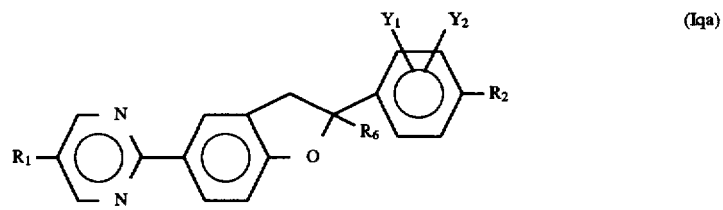
(Iqa)
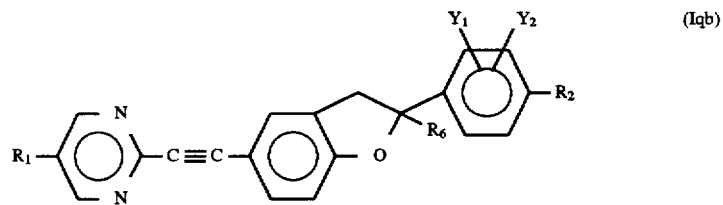
(Iqb)
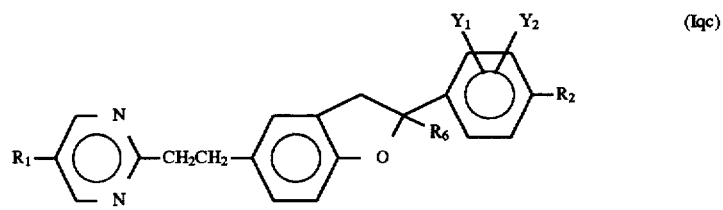
(Iqc)

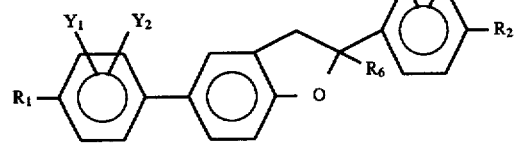  (Iqd)
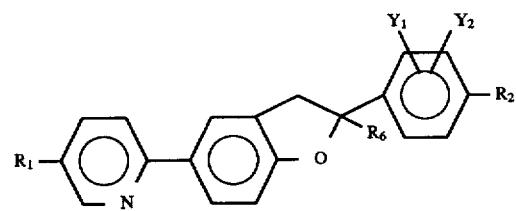  (Iqe)
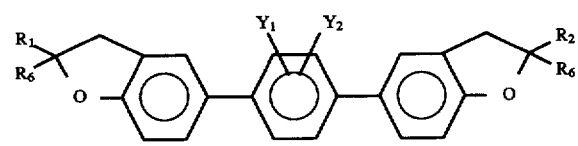  (Ira)
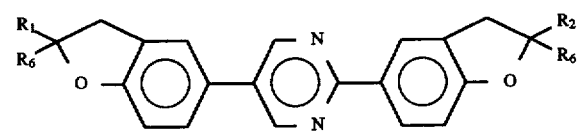  (Irb)
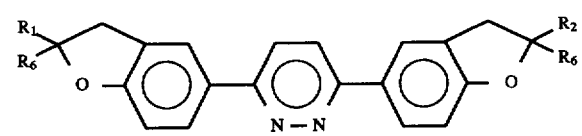  (Irc)
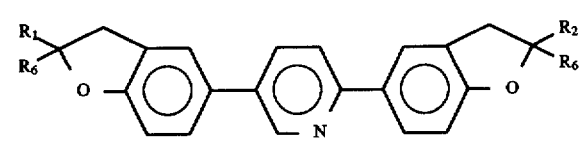  (Ird)
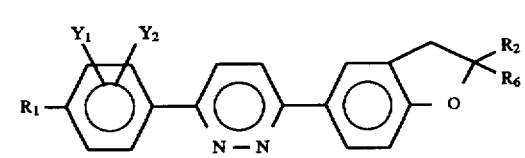  (Isa)
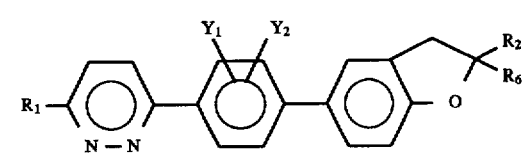  (Ita)
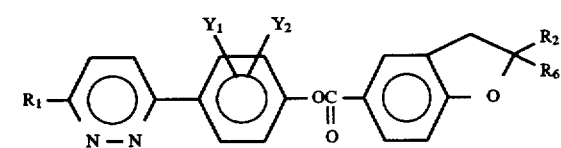  (Itb)
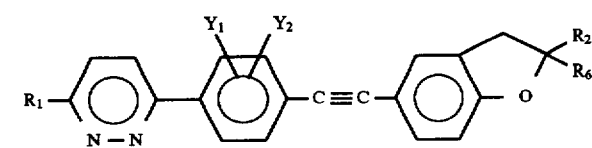  (Itc)

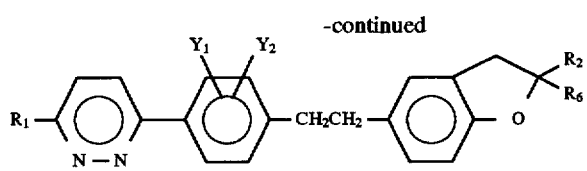

(Itd)

In the above formulae (Iaa–(Itd), $R_1$, $R_2$, $R_5$, $R_6$, $Y_1$ and $Y_2$ have the same meanings as described above.

In the mesomorphic compound of the formula (I) (including (Ia) to (It) and (Iaa) to (Itd)), $Y_1$ and $Y_2$ may preferably be hydrogen (H), halogen (F, Cl or Br) or trifluoromethyl (—CF$_3$), particularly H or F.

$R_1$ and $R_2$ in the formula (I) may preferably be selected from the following groups (i) to (vii):

(i) n-$C_aH_{2a+1}$—$X_3$—, (ii) $C_bH_{2b+1}\overset{CH_3}{\underset{|}{CH}}\text{+}CH_2\text{)}_d X_3$—, (iii) $C_eH_{2e+1}O\text{+}CH_2\text{)}_f\overset{CH_3}{\underset{|}{CH}}\text{+}CH_2\text{)}_g X_3$—, (iv) $C_hF_{2h+1}\text{+}CH_2\text{)}_i X_3$, (v) $C_jH_{2j+1}\overset{F}{\underset{|}{CH}}\text{+}CH_2\text{)}_k X_3$—, (vi) H, and

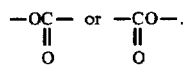

(vii) F, wherein a is an integer of 1–17; d, g and i are an integer of 0–7; b, e and h are an integer of 1 and 8, f and k are 0 or 1, j is an integer of 1–15; and $X_3$ denotes a single bond, —O—, $$-\underset{\underset{O}{\|}}{OC}-\text{ or }-\underset{\underset{O}{\|}}{CO}-.$$

$R_1$ and $R_2$ may more preferably be the group (i), the group (ii) or the group (v), particularly the group $X_3$ in the above groups (i) to (vi) may preferably be a single bond or —O—, particularly a single bond.

$R_5$ and $R_6$ in the formula (I) may preferably be hydrogen.

Further, the mesomorphic compound of the formula (I) may include a compound which does not show mesomorphism singly but shows mesomorphism in combination with another mesomorphic compound and/or the mesomorphic compound of the formula (I) which shows mesomorphism singly.

The mesomorphic compound of the above-mentioned formula (I) may generally be synthesized through, e.g., the following reaction scheme.

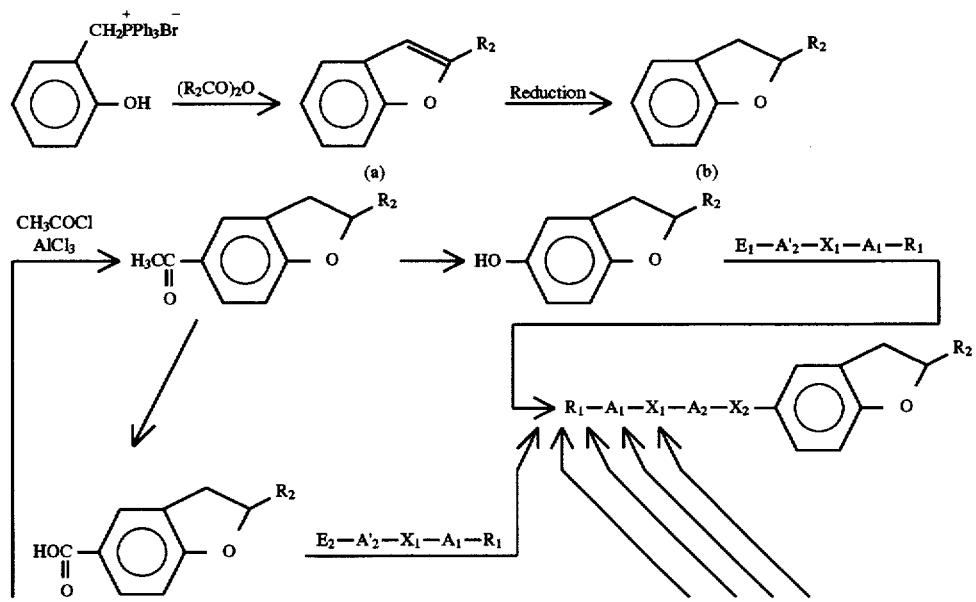

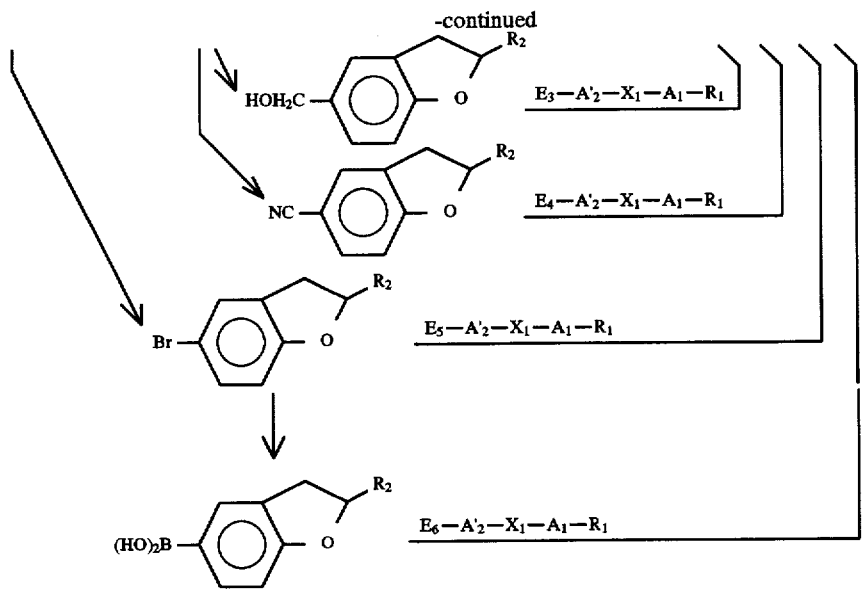

In the above reaction scheme, $R_1$, $R_2$, $A_1$, $A_2$, $X_1$ and $X_2$ have the same meanings given above. In case where $X_2$ is not a single bond; $E_1$ to $E_6$ are appropriate groups for forming $X_2$ and $A_2'$ is $A_2$. For example, $E_1$ may be carboxyl group when $X_2$ is —COO—; $E_2$ and $E_3$ may be hydroxyl group when $X_2$ is —OCO— or —OCH$_2$—; and $E_5$ may be —C≡CH when $X_2$ is —C≡C—. Further, in case where $X_2$ is a single bond, $E_1$—$A_2'$ to $E_6$—$A_2'$ are appropriate groups for forming $A_2$ after the reactions. For example, $E_5$—$A_2'$ may be $(HO)_2B$—$A_2$, and $E_6$—$A_2'$ may be Br—$A_2$ or $CF_3SO_2O$—$A_2$.

Further, in the above reaction scheme, the intermediate products having a benzofuran ring (a) and coumaran ring (b) can be synthesized through processes shown in the following documents (i)–(iv).

(i) Gabriert, A. et al., Compt. rend., 235, 1407 (1952)

(ii) Davies, J. S. H. et al., J. Chem. Soc., 1950, 3195, P. 3210

(iii) A. Hercouet et al., Tetrahedron Lett., 2145 (1979), pp. 2145–2147

(iv) Gurinder J. S. Doad et al., Tetrahedron Lett., 30, 1597 (1989), pp. 1597–1598.

(v) Fumio Toda et al., J. Org. Chem., 55, 3447 (1990). p. 3449.

Specific examples of the mesomorphic compounds represented by the formula (I) may include those shown in the following structural formulae.

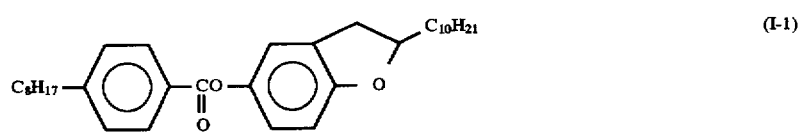

(I-1)

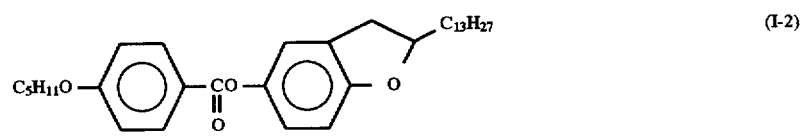

(I-2)

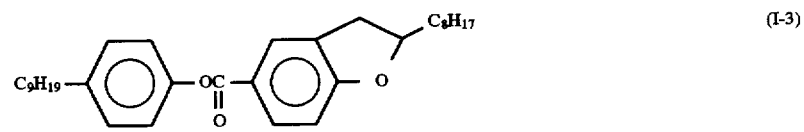

(I-3)

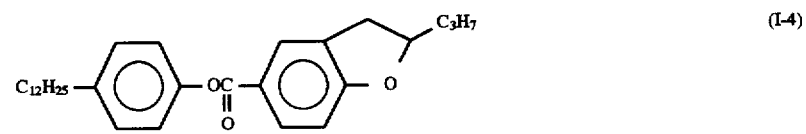

(I-4)

-continued
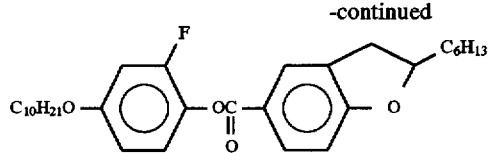
(I-5)
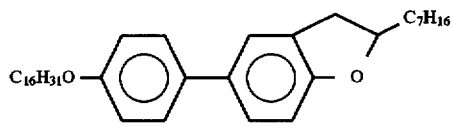
(I-6)
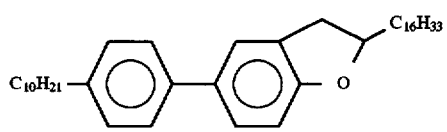
(I-7)
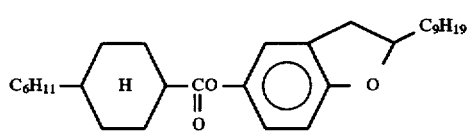
(I-8)
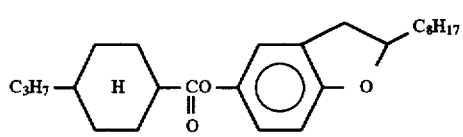
(I-9)
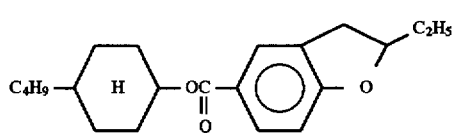
(I-10)
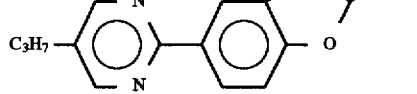
(I-11)
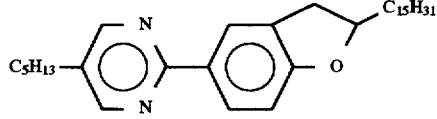
(I-12)
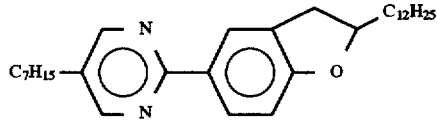
(I-13)
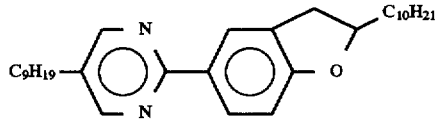
(I-14)
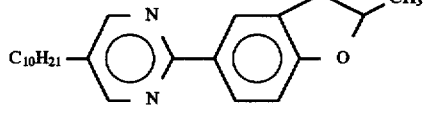
(I-15)
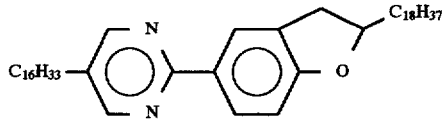
(I-16)

-continued
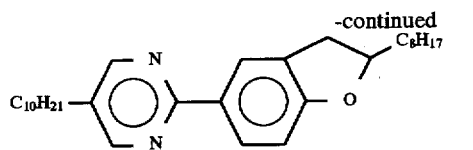 (I-17)
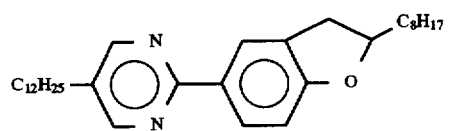 (I-18)
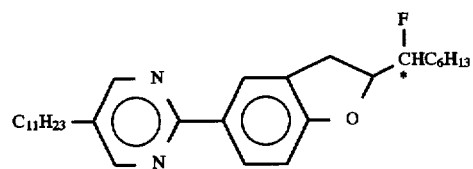 (I-19)
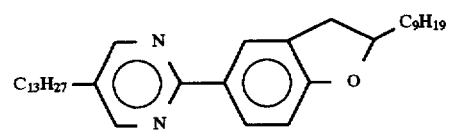 (I-20)
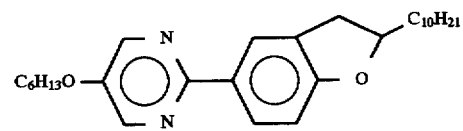 (I-21)
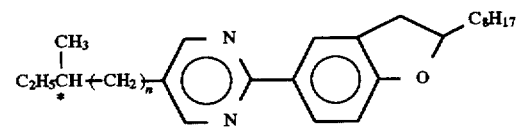 (I-22)
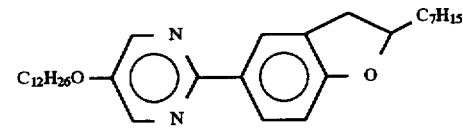 (I-23)
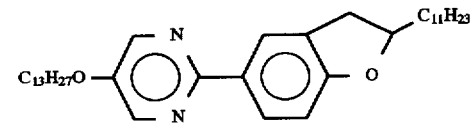 (I-24)
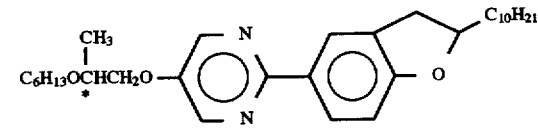 (I-25)
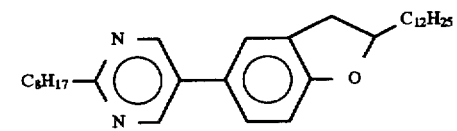 (I-26)
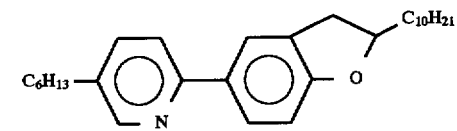 (I-27)
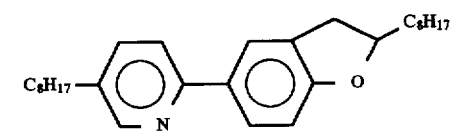 (I-28)

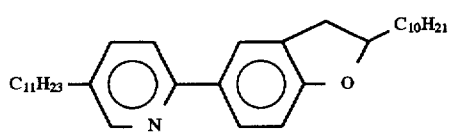 (I-29)
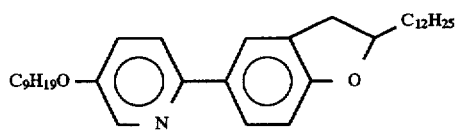 (I-30)
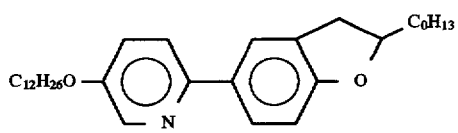 (I-31)
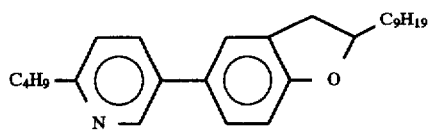 (I-32)
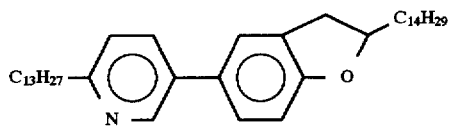 (I-33)
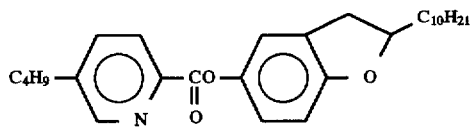 (I-34)
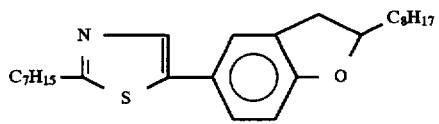 (I-35)
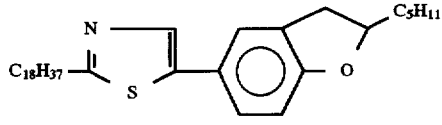 (I-36)
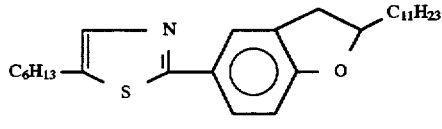 (I-37)
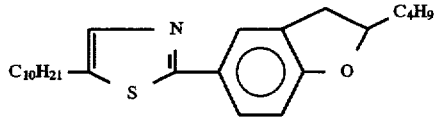 (I-38)
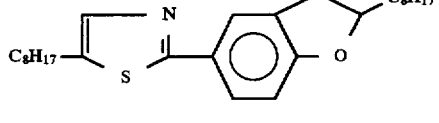 (I-39)
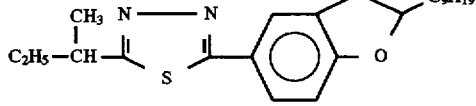 (I-40)

-continued
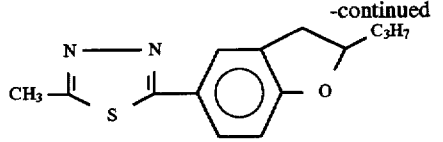 (I-41)
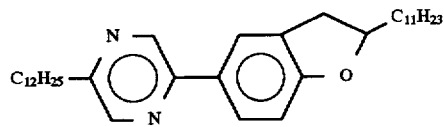 (I-42)
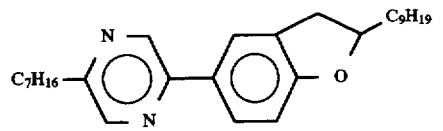 (I-43)
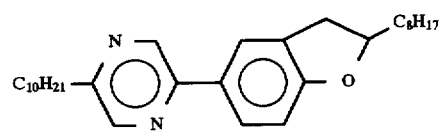 (I-44)
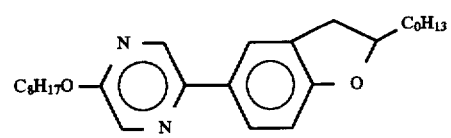 (I-45)
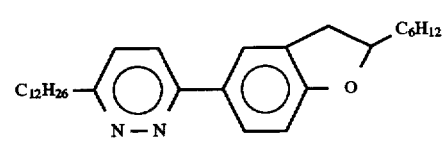 (I-46)
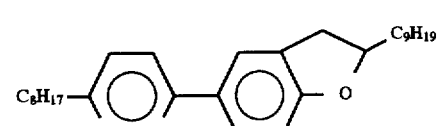 (I-47)
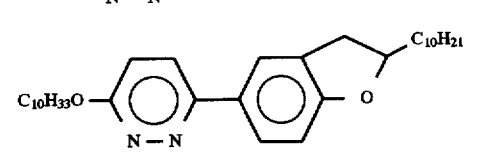 (I-48)
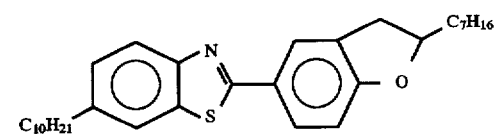 (I-49)
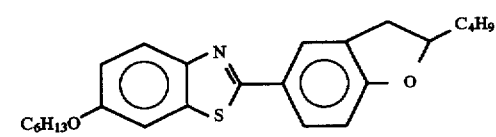 (I-50)
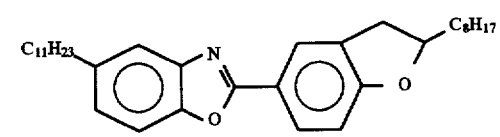 (I-51)
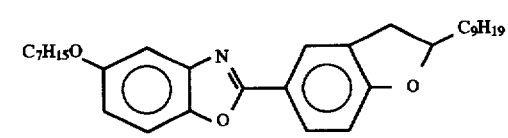 (I-52)

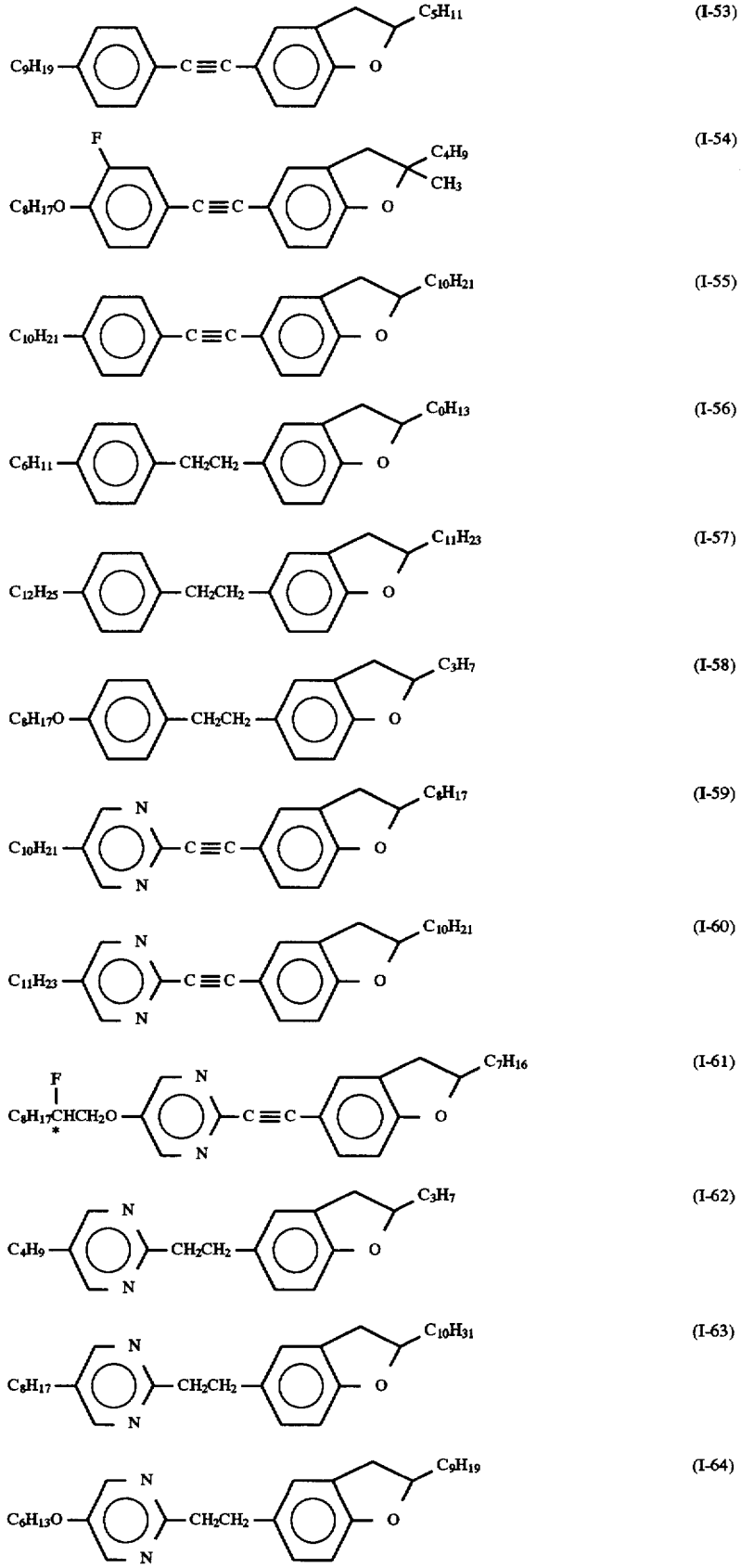

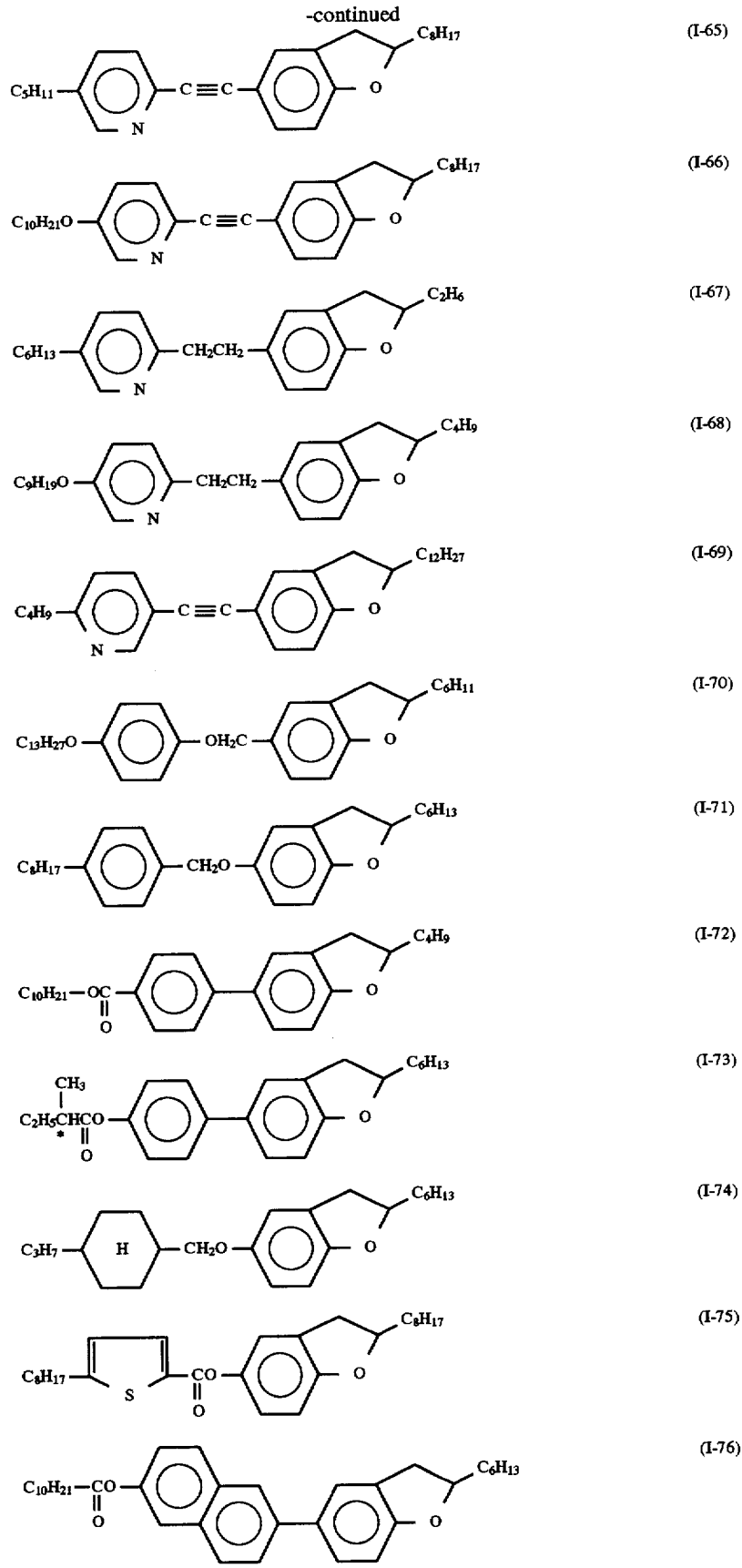

-continued
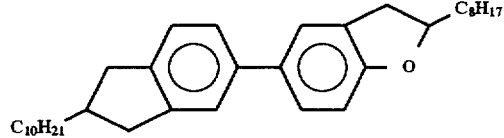 (I-77)
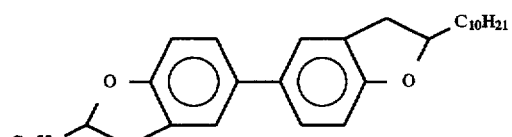 (I-78)
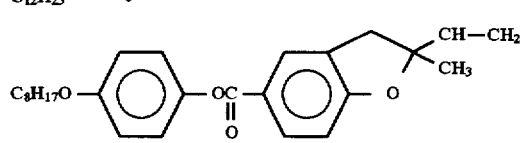 (I-79)
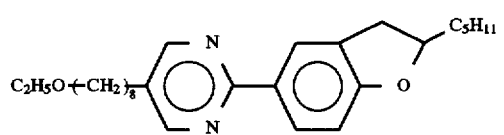 (I-80)
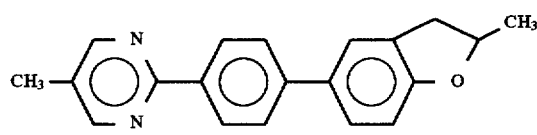 (I-81)
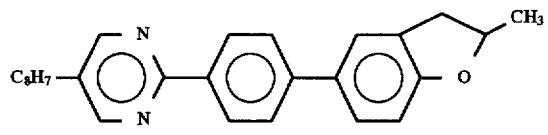 (I-82)
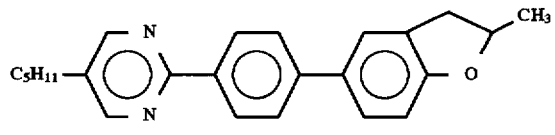 (I-83)
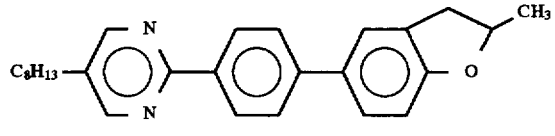 (I-84)
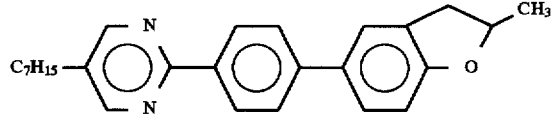 (I-85)
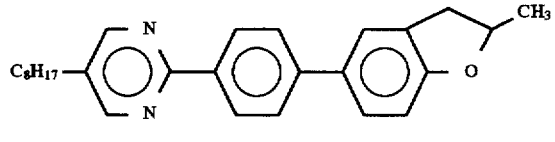 (I-86)
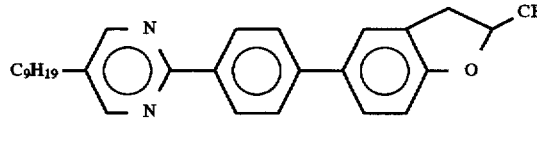 (I-87)
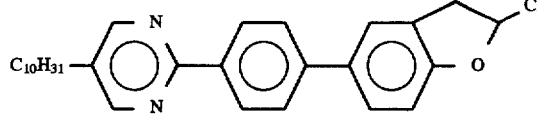 (I-88)

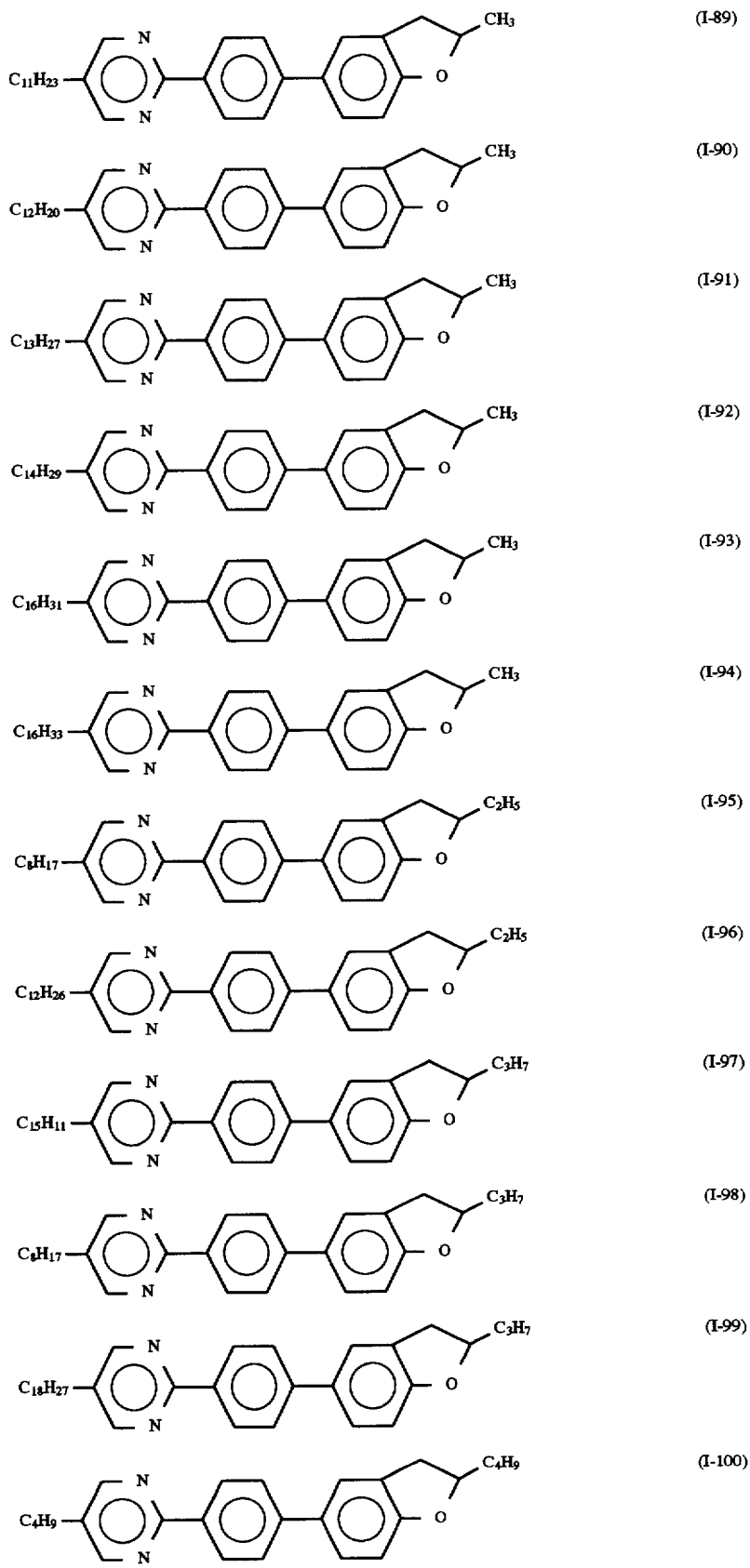

-continued
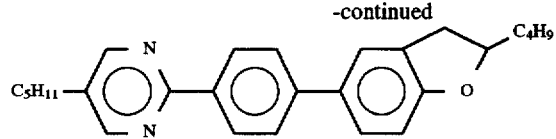 (I-101)
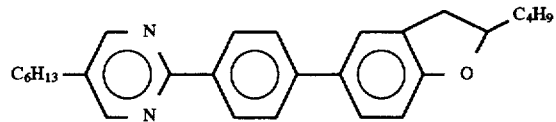 (I-102)
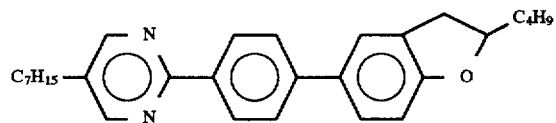 (I-103)
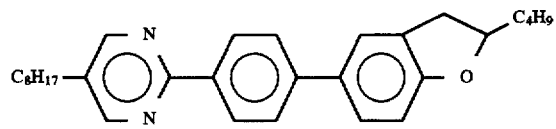 (I-104)
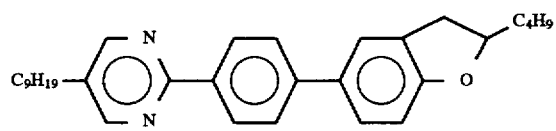 (I-105)
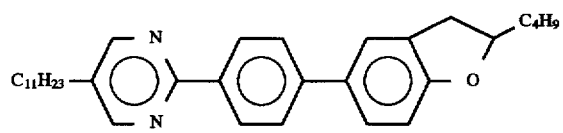 (I-106)
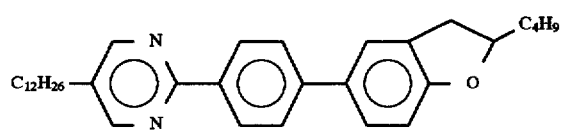 (I-107)
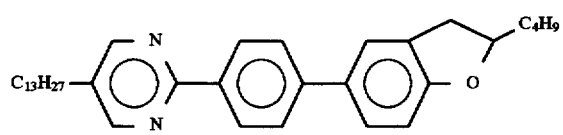 (I-108)
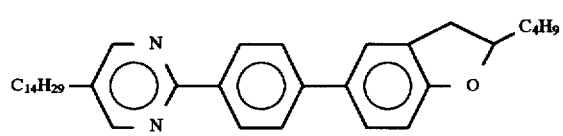 (I-109)
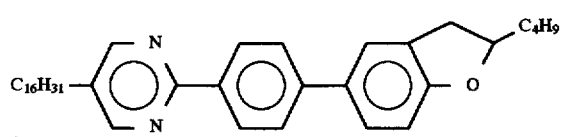 (I-110)
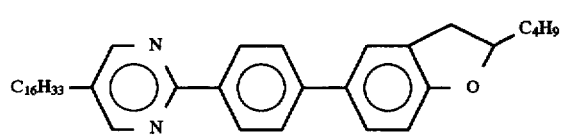 (I-111)
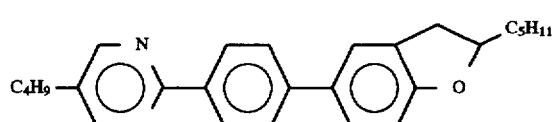 (I-112)

-continued
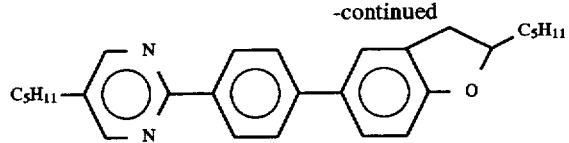 (I-113)
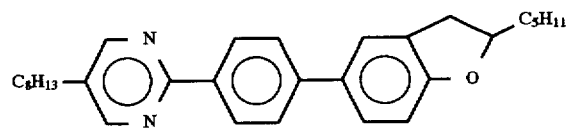 (I-114)
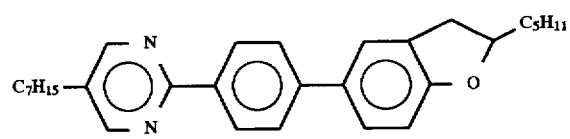 (I-115)
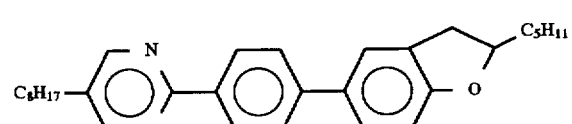 (I-116)
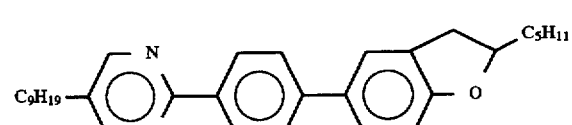 (I-117)
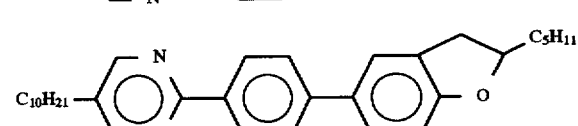 (I-118)
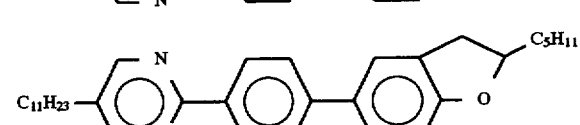 (I-119)
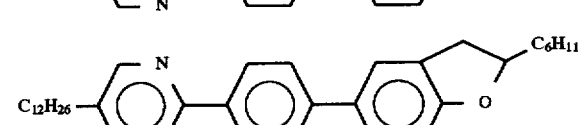 (I-120)
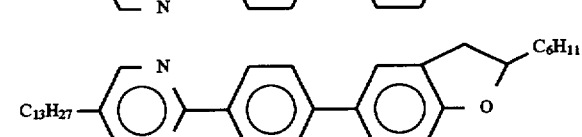 (I-121)
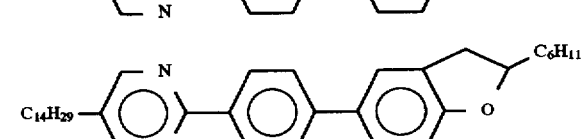 (I-122)
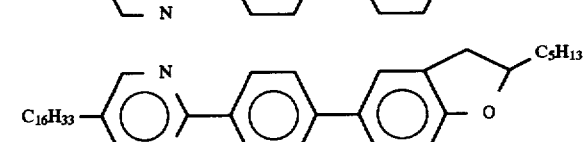 (I-123)
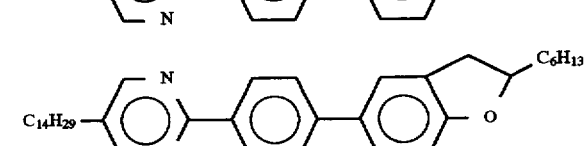 (I-124)

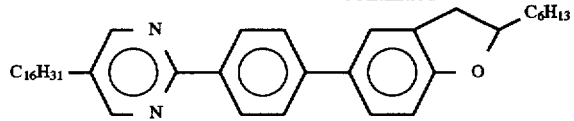 (I-125)
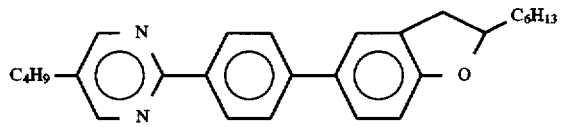 (I-126)
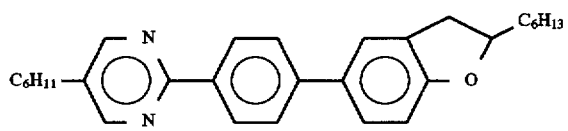 (I-127)
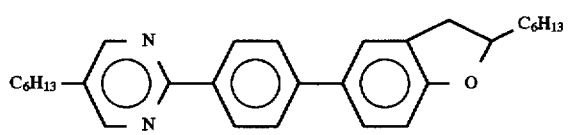 (I-128)
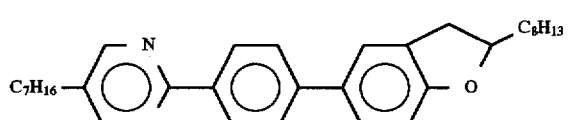 (I-129)
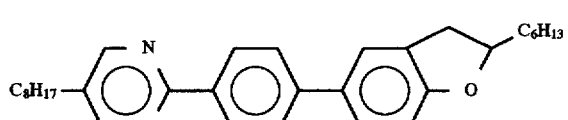 (I-130)
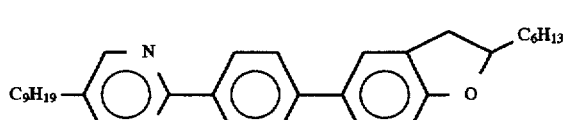 (I-131)
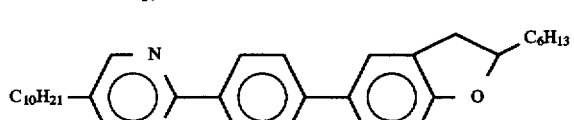 (I-132)
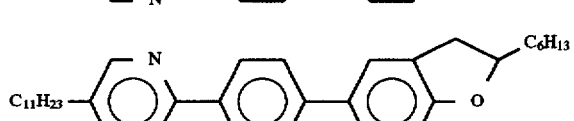 (I-133)
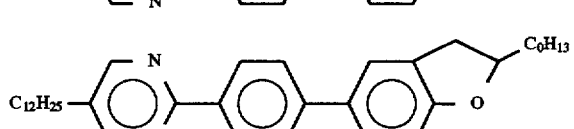 (I-134)
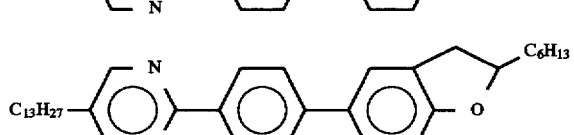 (I-135)
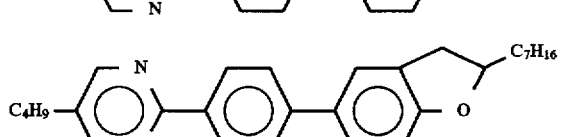 (I-136)

-continued
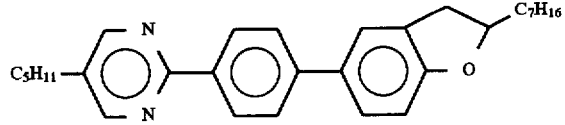 (I-137)
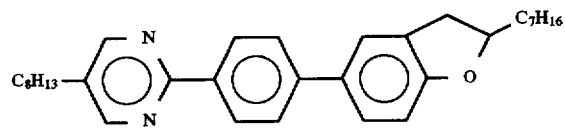 (I-138)
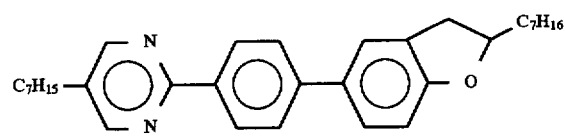 (I-139)
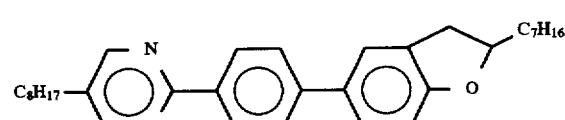 (I-140)
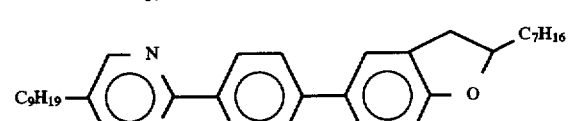 (I-141)
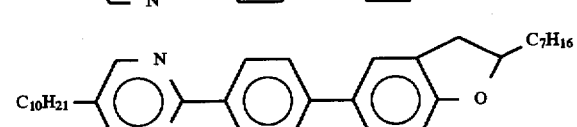 (I-142)
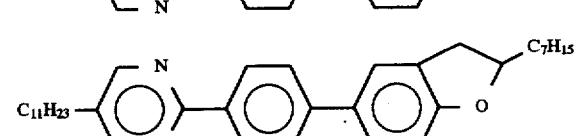 (I-143)
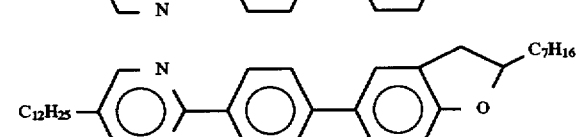 (I-144)
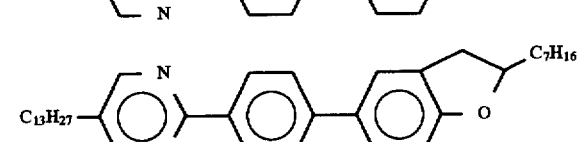 (I-145)
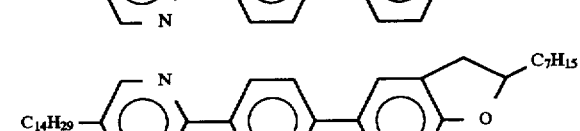 (I-146)
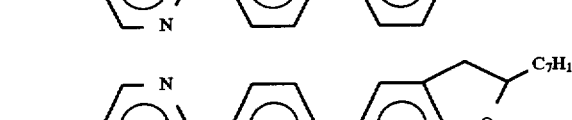 (I-147)
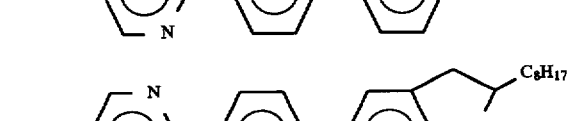 (I-148)

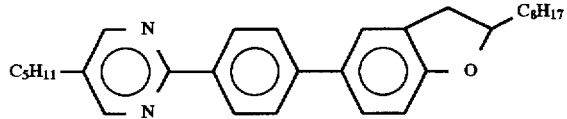 (I-149)
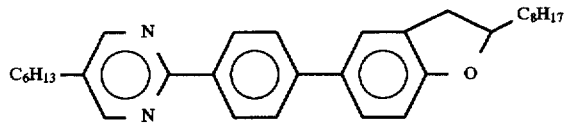 (I-150)
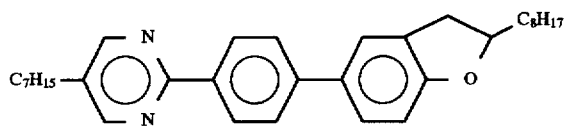 (I-151)
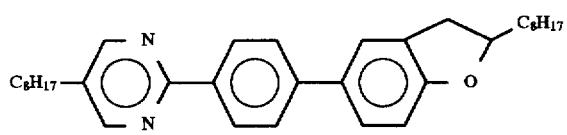 (I-152)
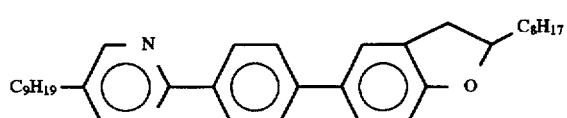 (I-153)
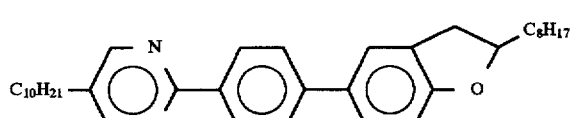 (I-154)
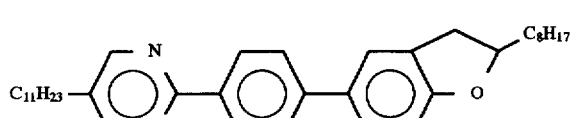 (I-155)
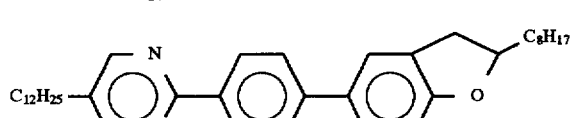 (I-156)
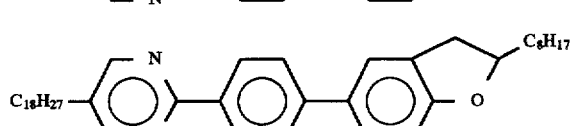 (I-157)
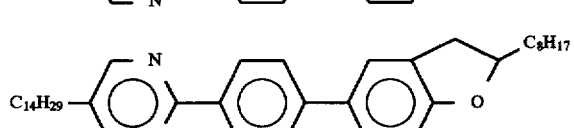 (I-158)
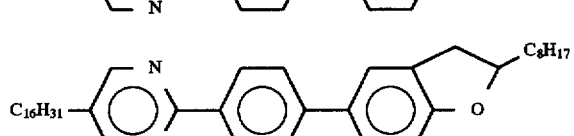 (I-159)
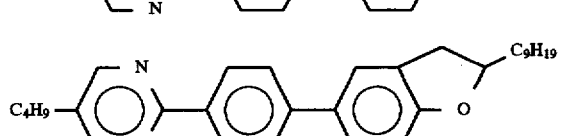 (I-160)

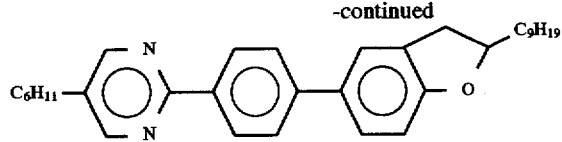 (I-161)
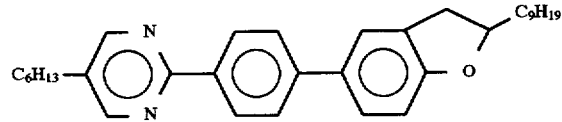 (I-162)
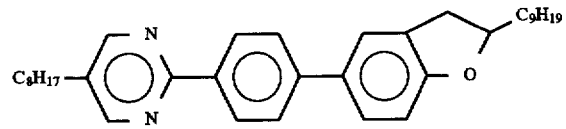 (I-163)
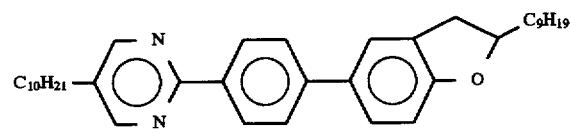 (I-164)
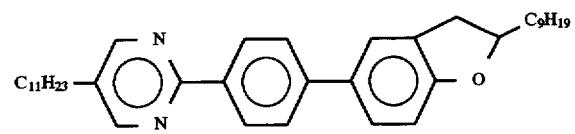 (I-165)
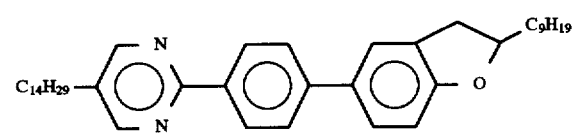 (I-166)
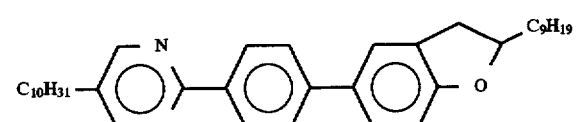 (I-167)
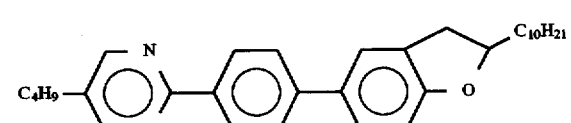 (I-168)
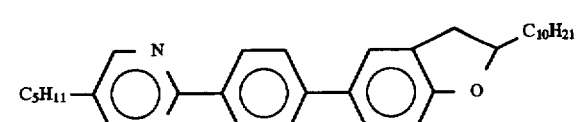 (I-169)
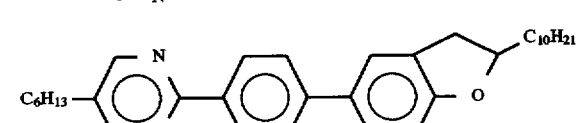 (I-170)
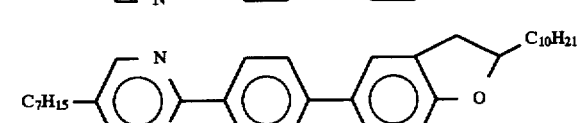 (I-171)
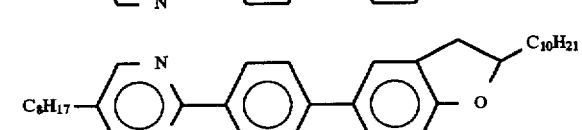 (I-172)

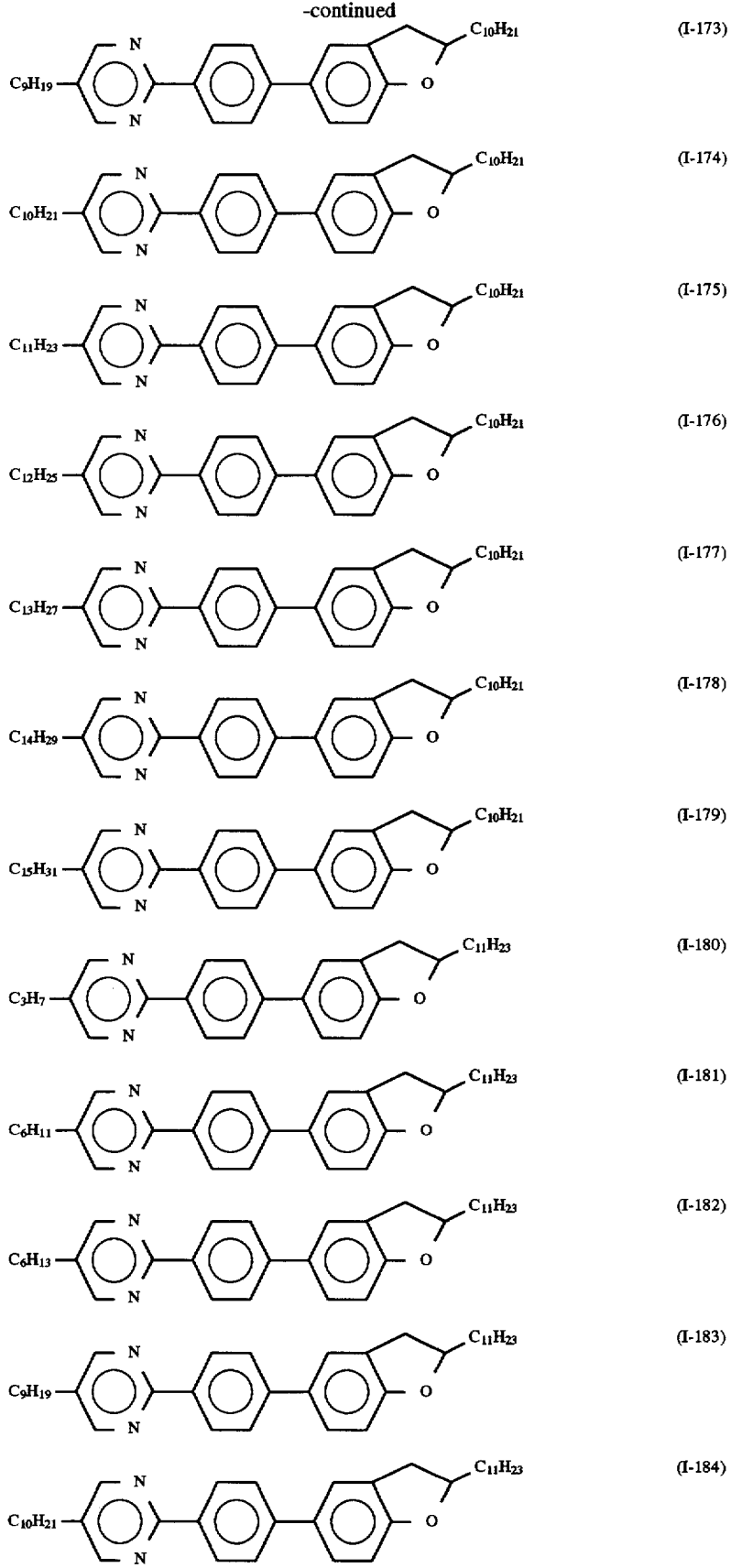

-continued
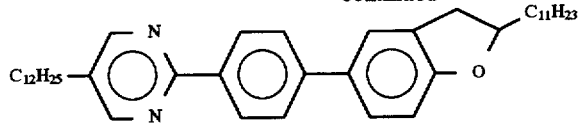 (I-185)
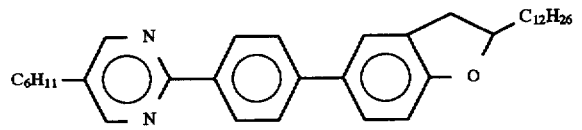 (I-186)
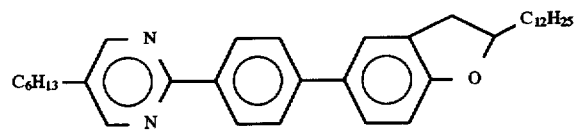 (I-187)
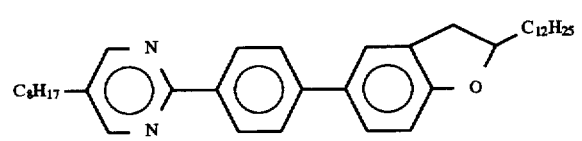 (I-188)
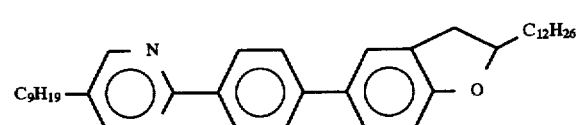 (I-189)
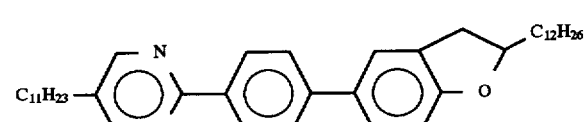 (I-190)
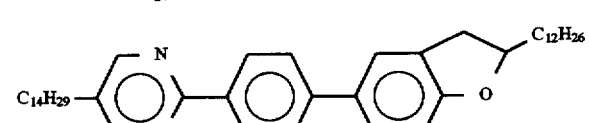 (I-191)
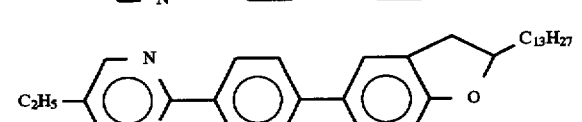 (I-192)
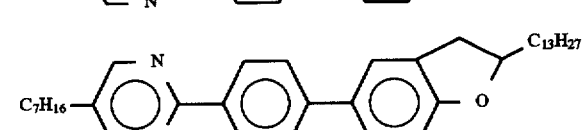 (I-193)
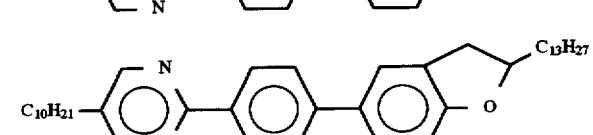 (I-194)
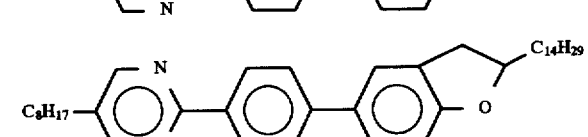 (I-195)
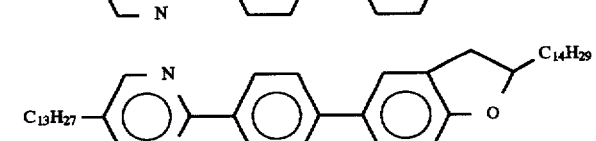 (I-196)

-continued
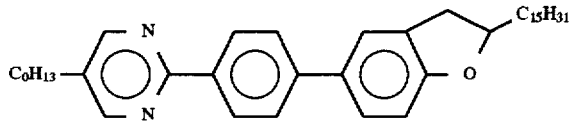 (I-197)
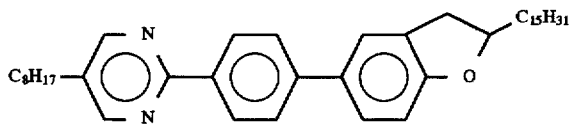 (I-198)
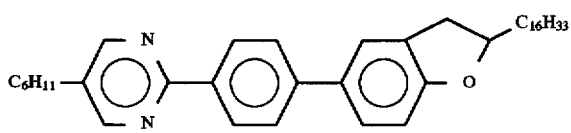 (I-199)
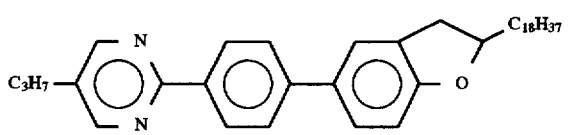 (I-200)
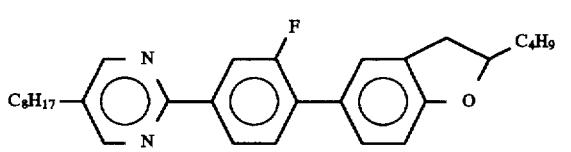 (I-201)
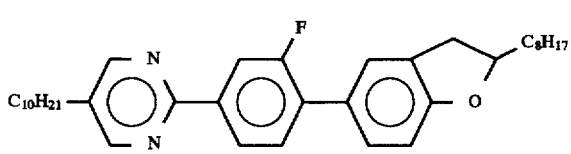 (I-202)
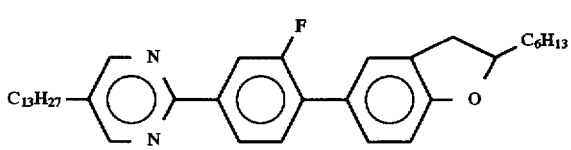 (I-203)
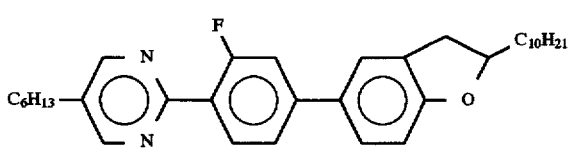 (I-204)
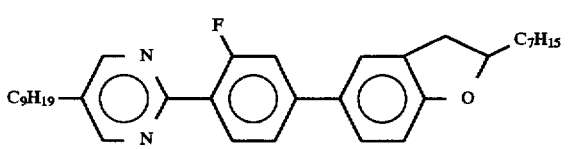 (I-205)
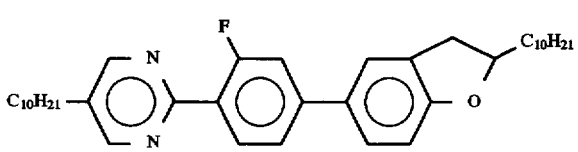 (I-206)
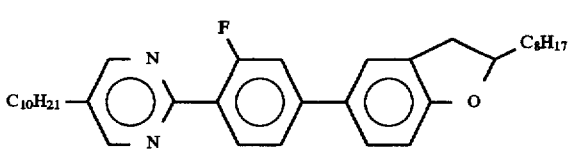 (I-207)

-continued
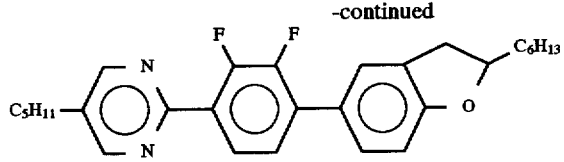 (I-208)
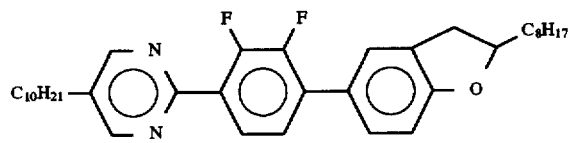 (I-209)
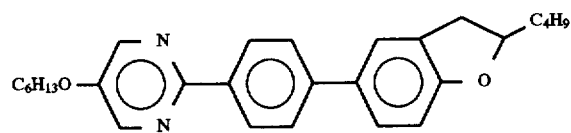 (I-210)
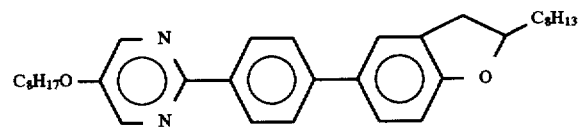 (I-211)
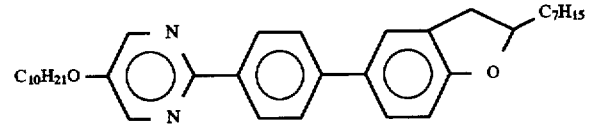 (I-212)
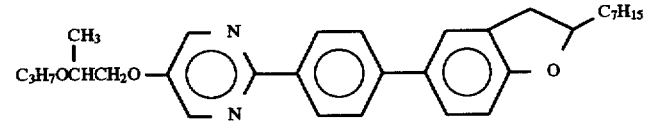 (I-213)
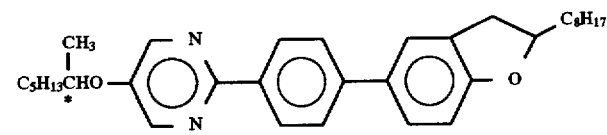 (I-214)
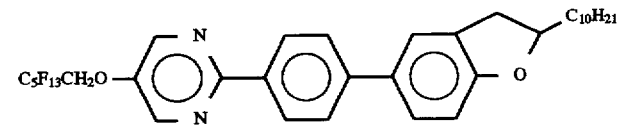 (I-215)
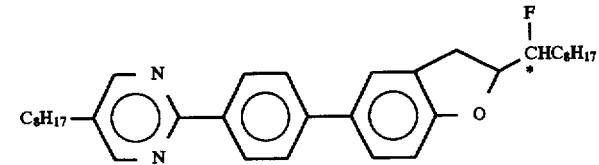 (I-216)
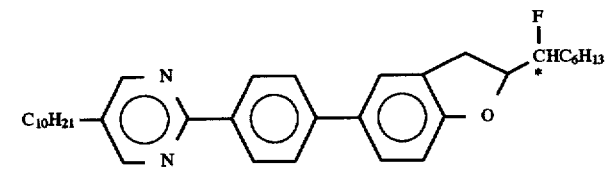 (I-217)
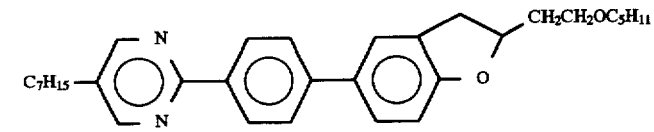 (I-218)

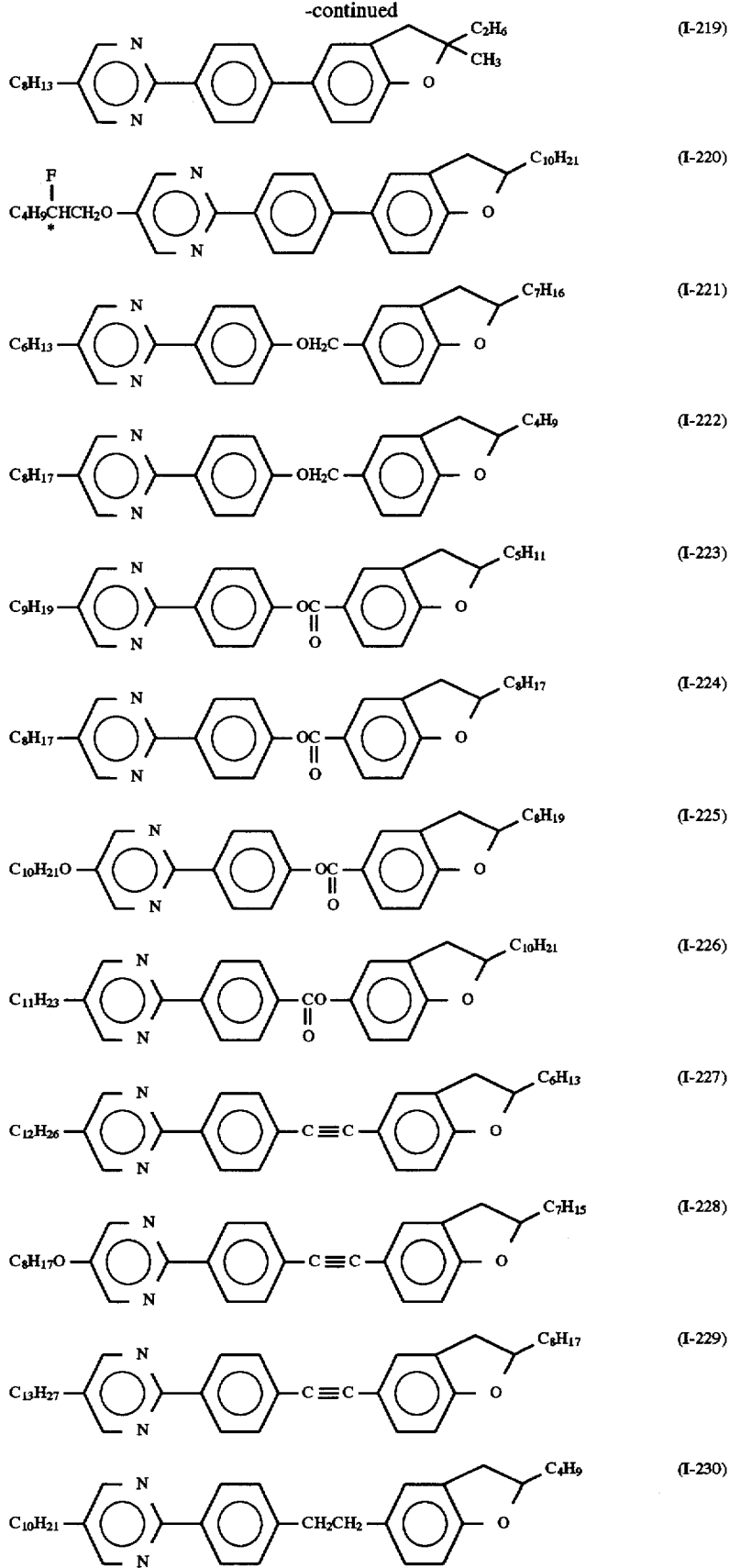

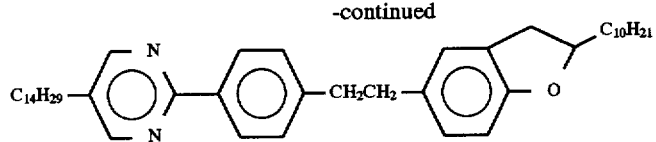 (I-231)
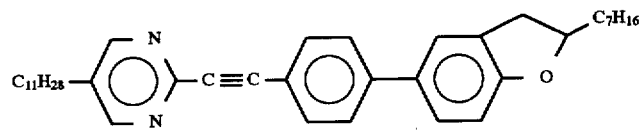 (I-232)
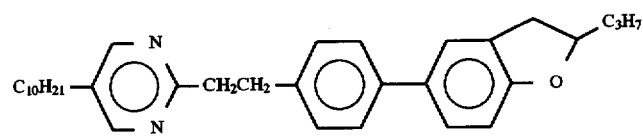 (I-233)
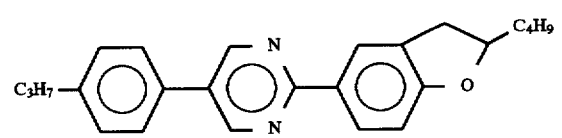 (I-234)
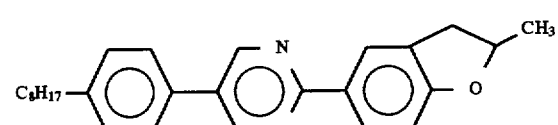 (I-235)
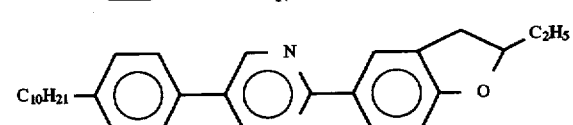 (I-236)
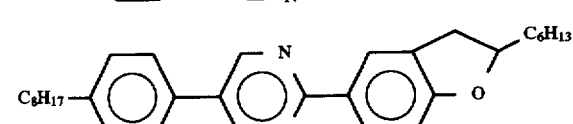 (I-237)
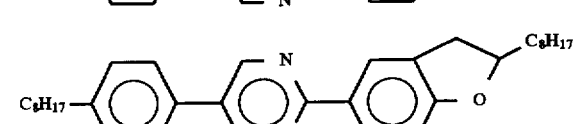 (I-238)
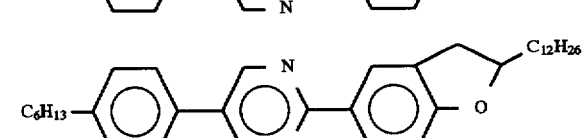 (I-239)
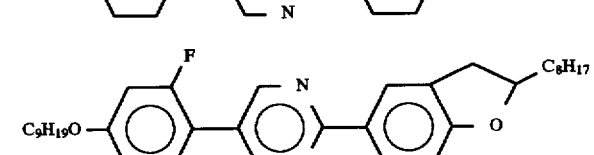 (I-240)
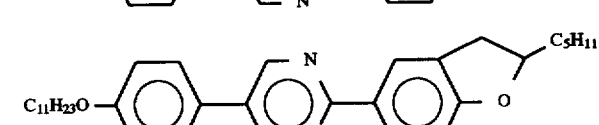 (I-241)
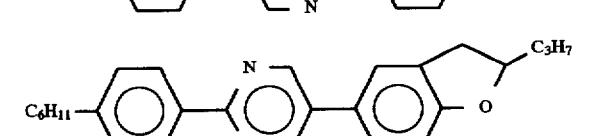 (I-242)

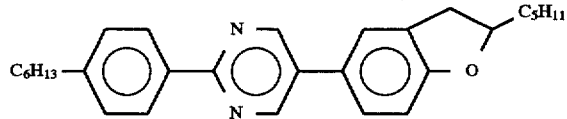 (I-243)
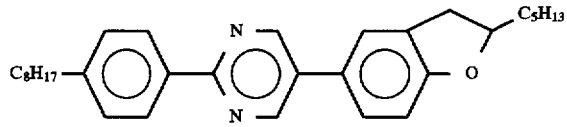 (I-244)
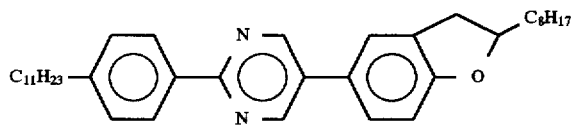 (I-245)
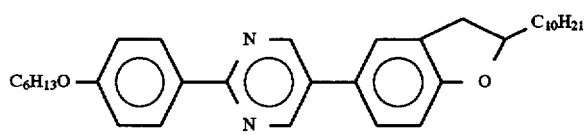 (I-246)
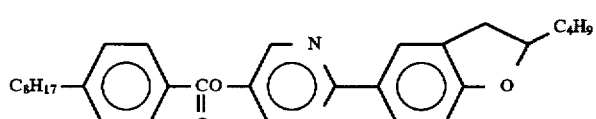 (I-247)
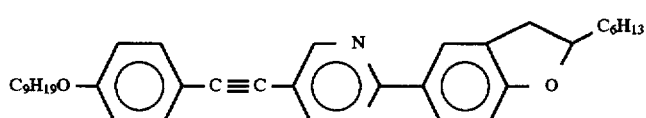 (I-248)
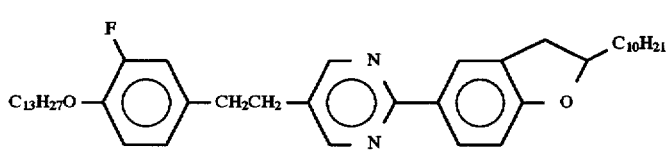 (I-249)
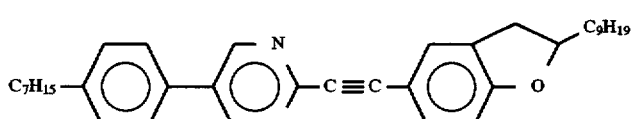 (I-250)
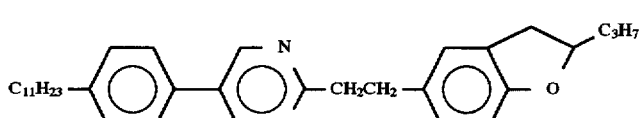 (I-251)
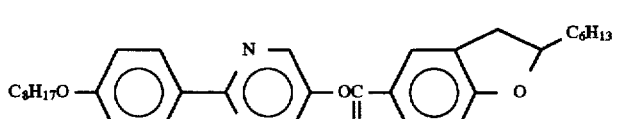 (I-252)
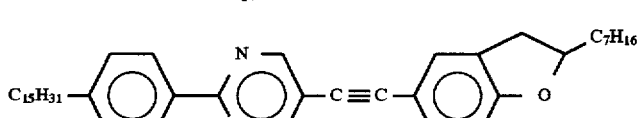 (I-253)
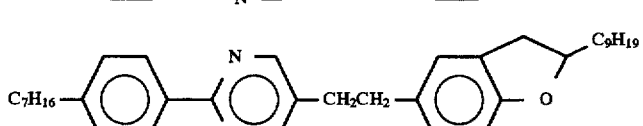 (I-254)

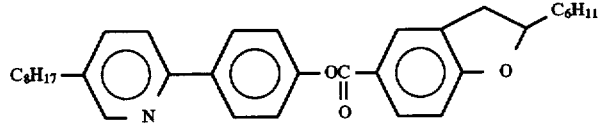 (I-255)
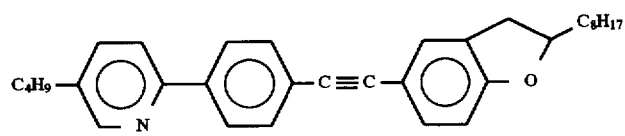 (I-256)
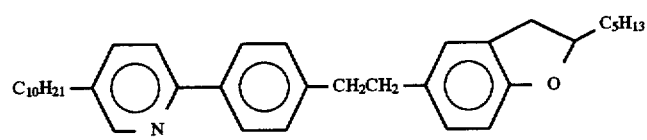 (I-257)
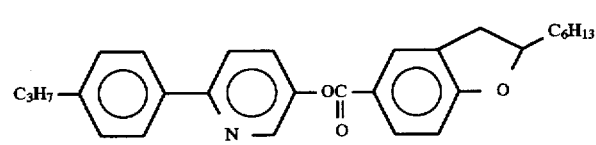 (I-258)
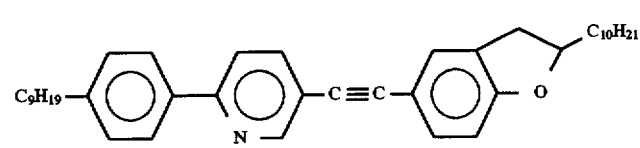 (I-259)
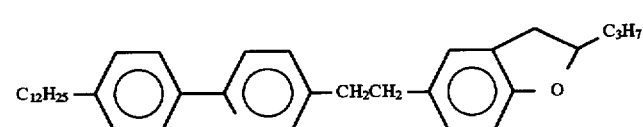 (I-260)
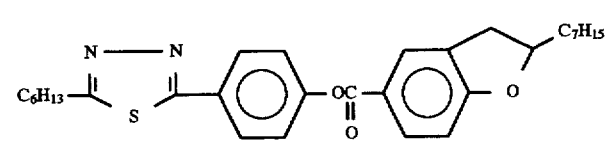 (I-261)
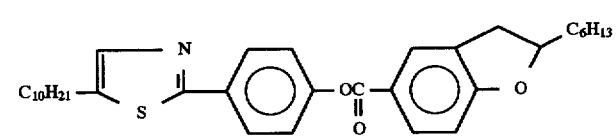 (I-262)
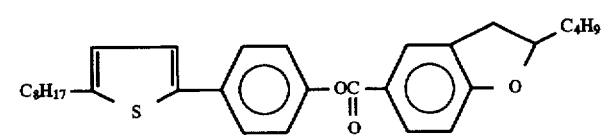 (I-263)
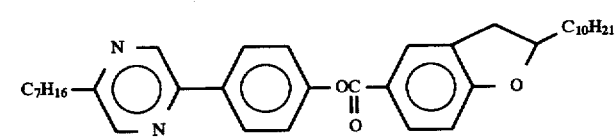 (I-264)
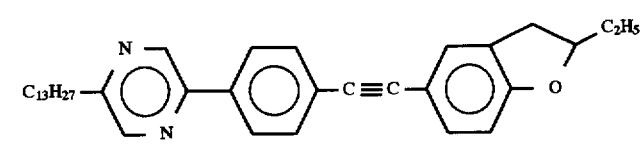 (I-265)
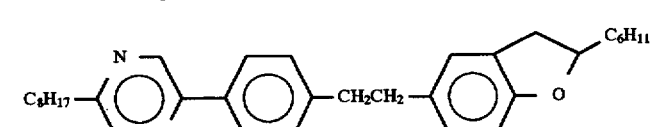 (I-266)

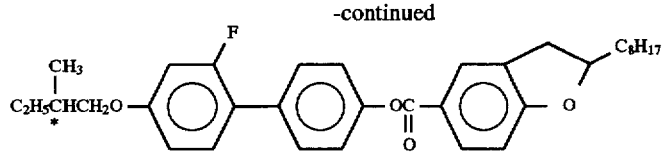
(I-267)
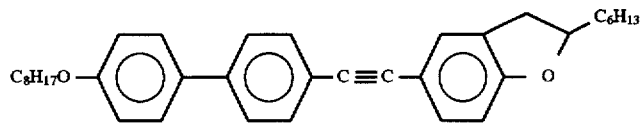
(I-268)
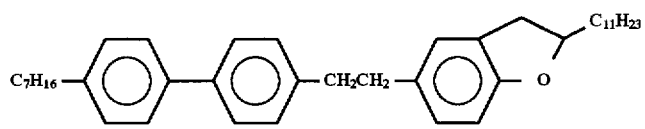
(I-269)
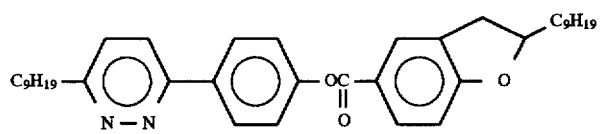
(I-270)
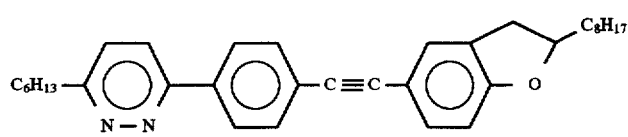
(I-271)
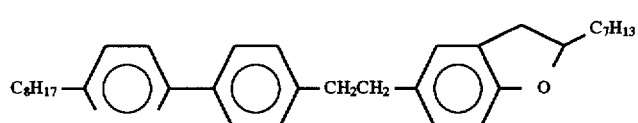
(I-272)
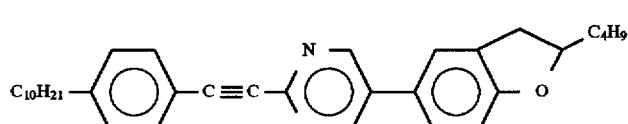
(I-273)
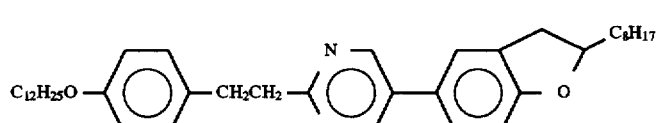
(I-274)
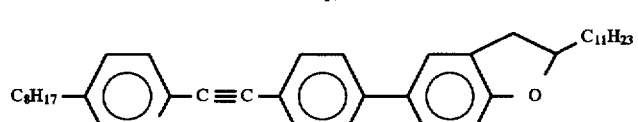
(I-275)
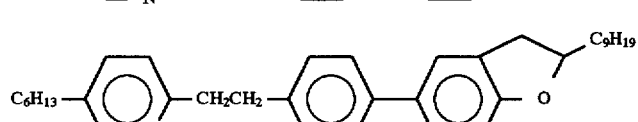
(I-276)
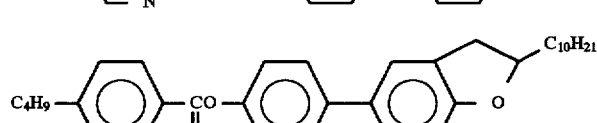
(I-277)
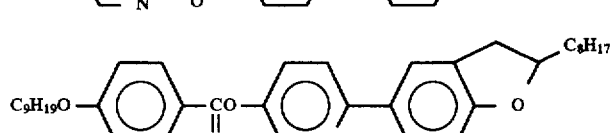
(I-278)

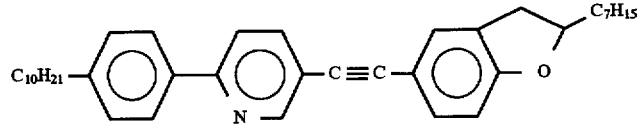 (I-279)
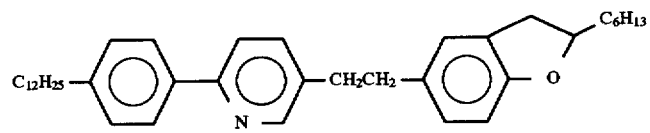 (I-280)
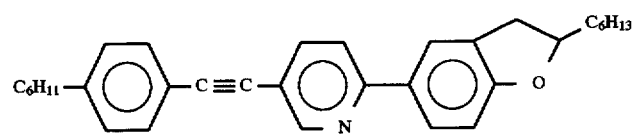 (I-281)
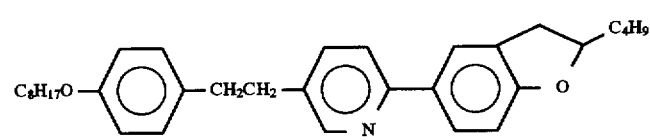 (I-282)
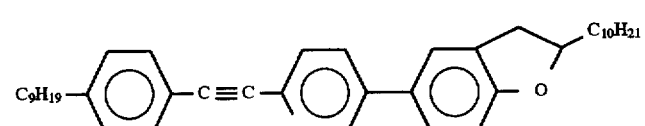 (I-283)
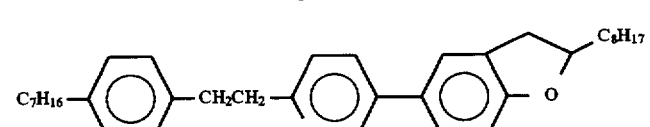 (I-284)
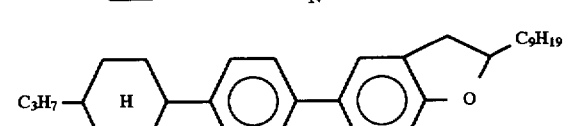 (I-285)
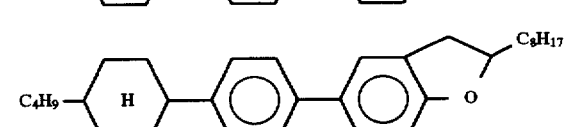 (I-286)
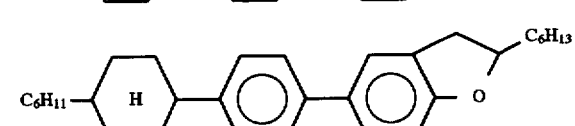 (I-287)
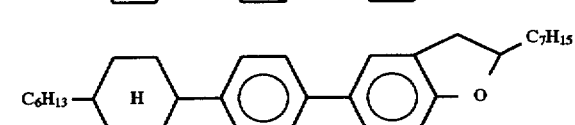 (I-288)
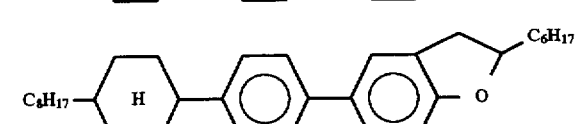 (I-289)
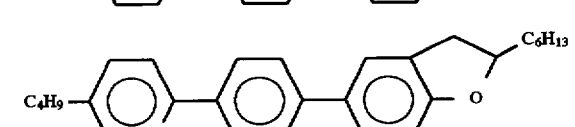 (I-290)

-continued
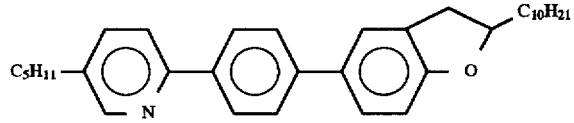 (I-291)
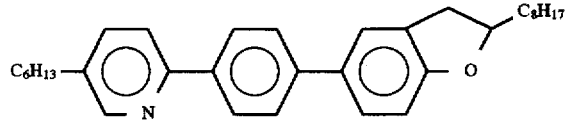 (I-292)
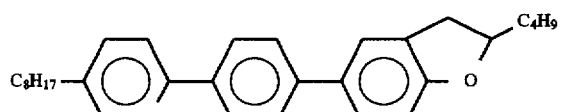 (I-293)
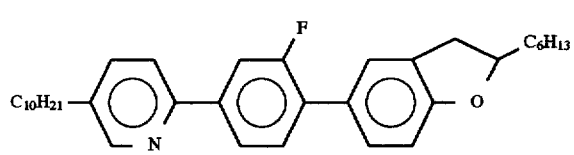 (I-294)
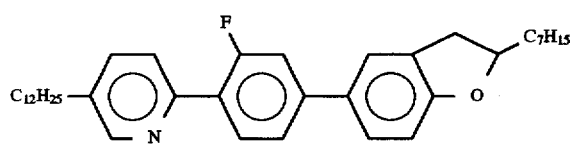 (I-295)
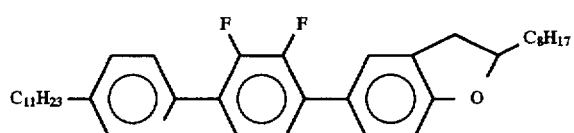 (I-296)
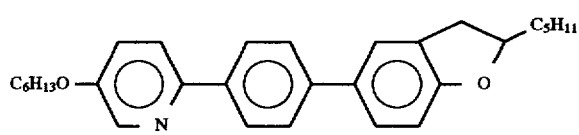 (I-297)
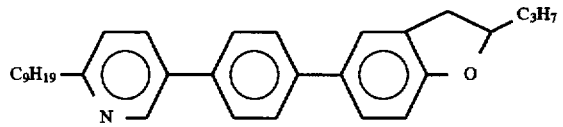 (I-298)
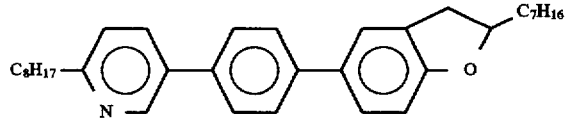 (I-299)
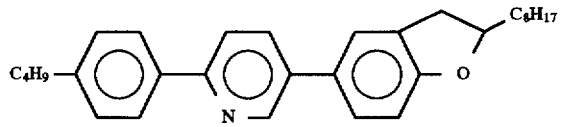 (I-300)
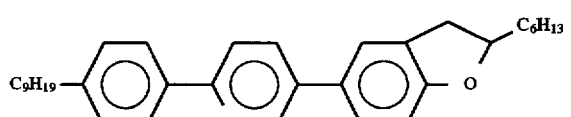 (I-301)
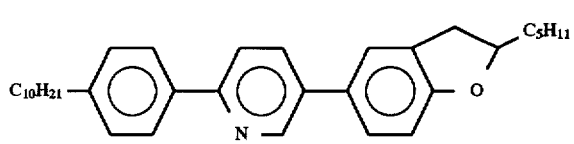 (I-302)

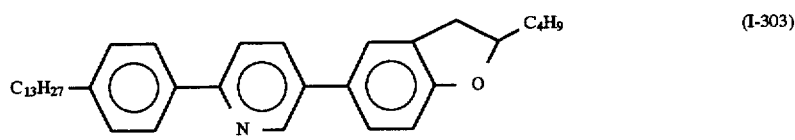 (I-303)
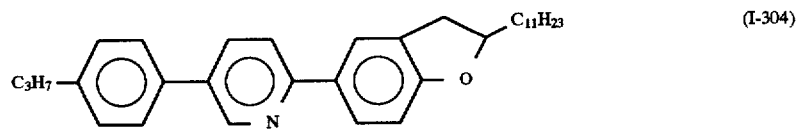 (I-304)
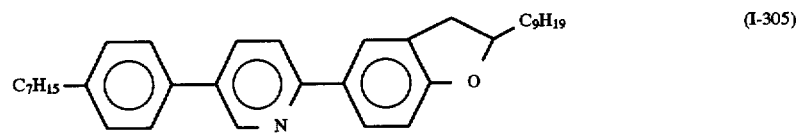 (I-305)
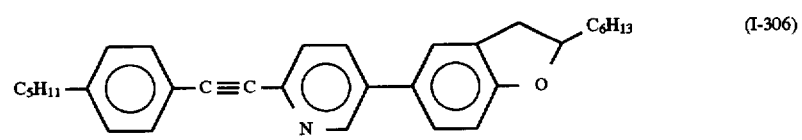 (I-306)
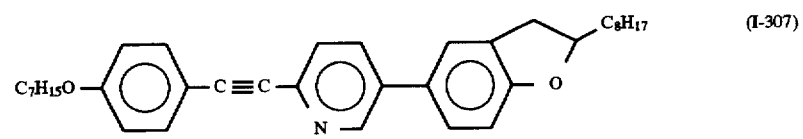 (I-307)
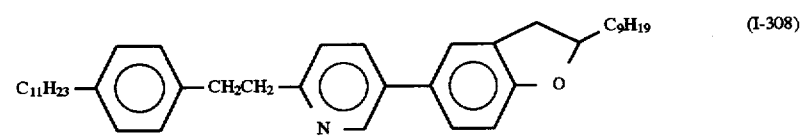 (I-308)
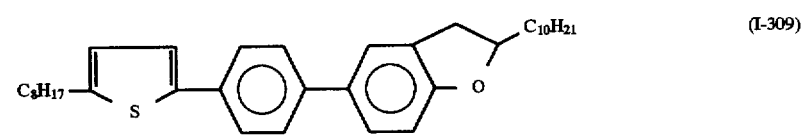 (I-309)
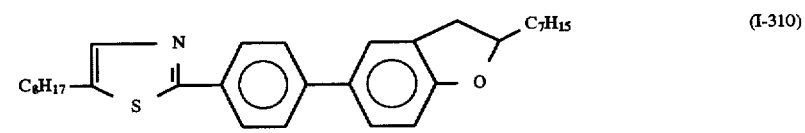 (I-310)
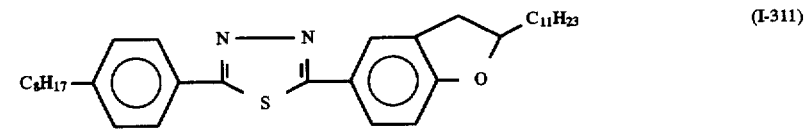 (I-311)
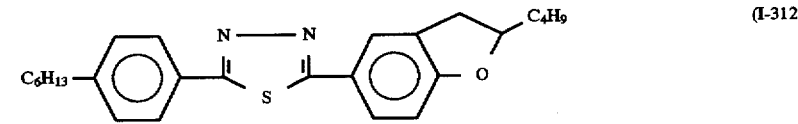 (I-312)
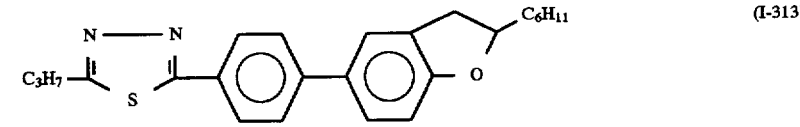 (I-313)
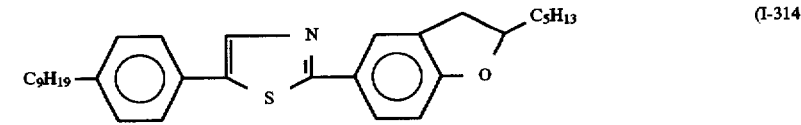 (I-314)

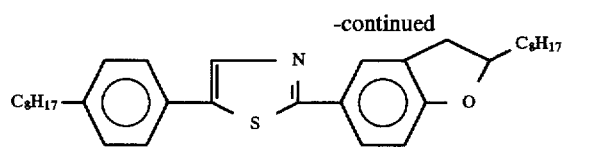 (I-315)
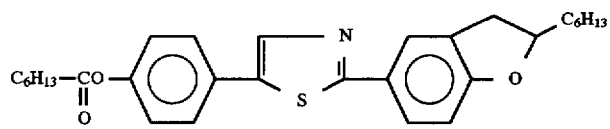 (I-316)
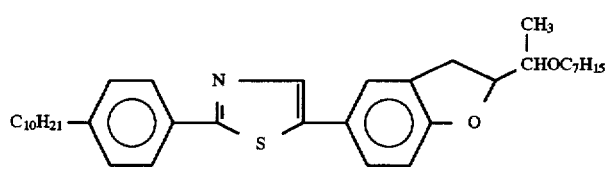 (I-317)
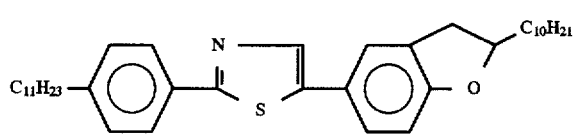 (I-318)
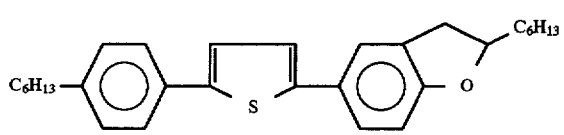 (I-319)
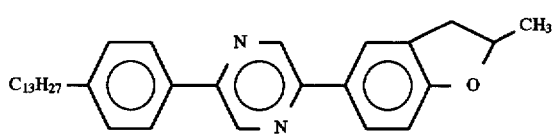 (I-320)
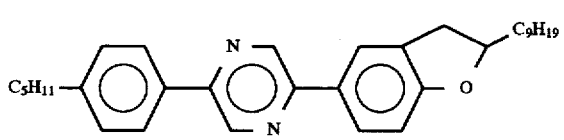 (I-321)
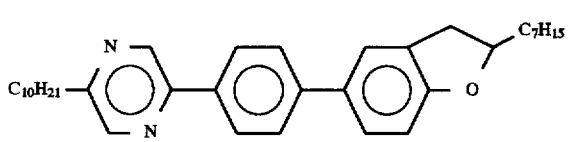 (I-322)
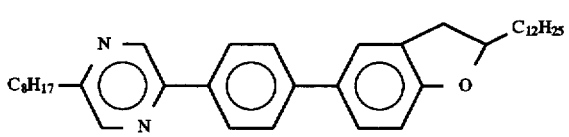 (I-323)
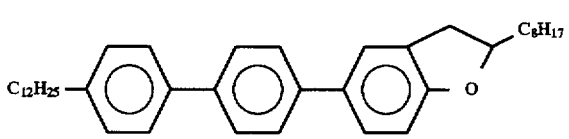 (I-324)
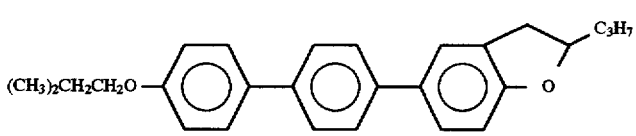 (I-325)
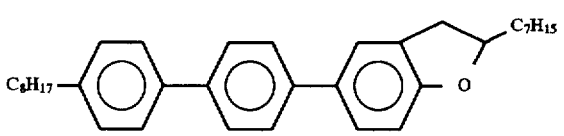 (I-326)

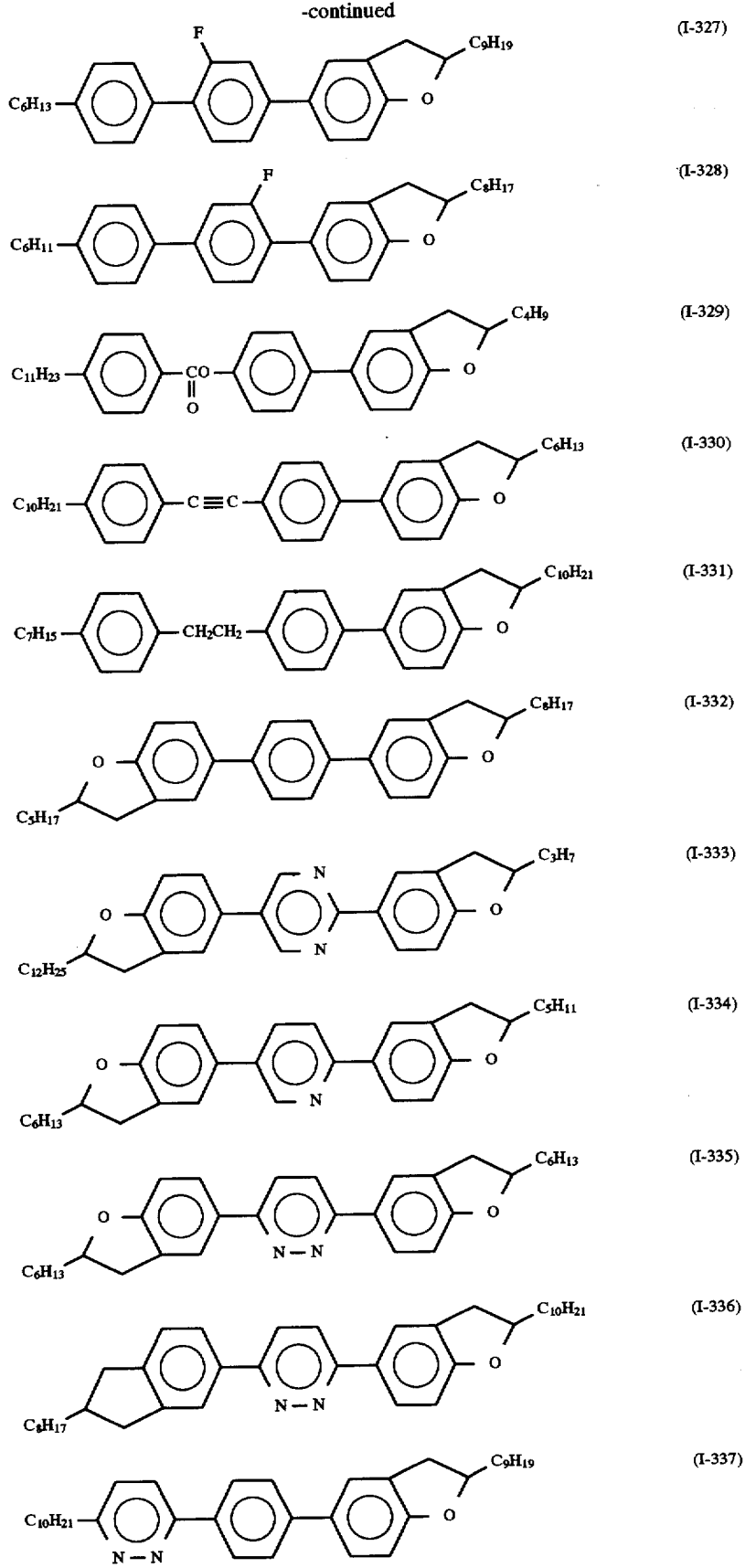

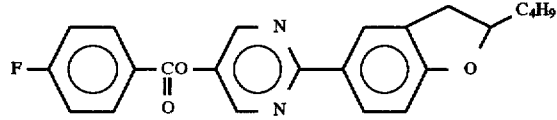
(I-338)
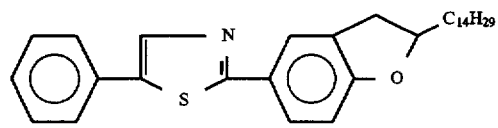
(I-339)
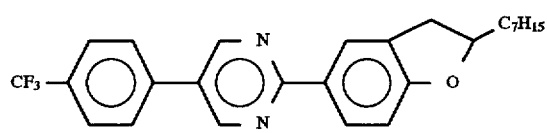
(I-340)
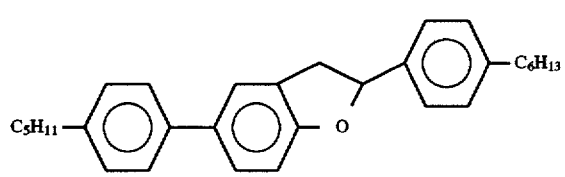
(I-341)
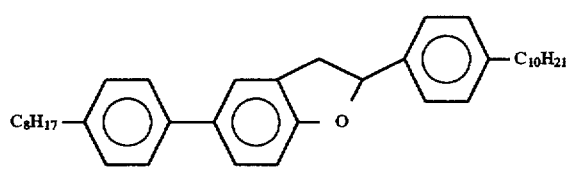
(I-342)
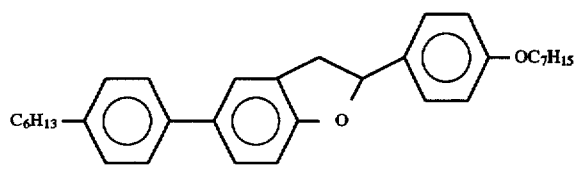
(I-343)
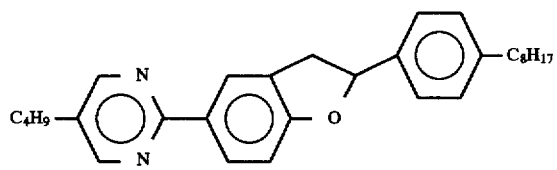
(I-344)
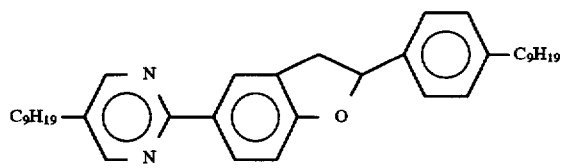
(I-345)
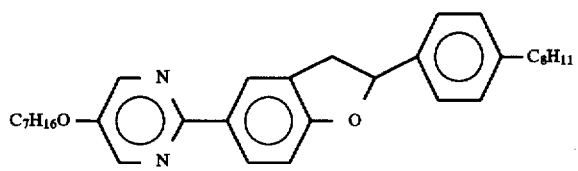
(I-346)
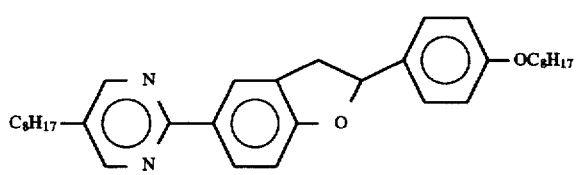
(I-347)

-continued
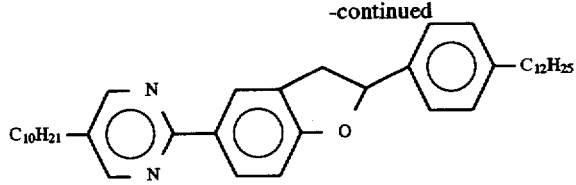 (I-348)
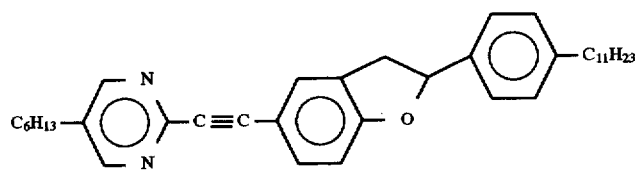 (I-349)
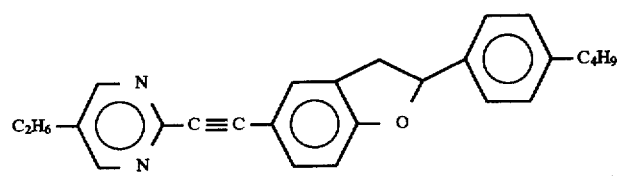 (I-350)
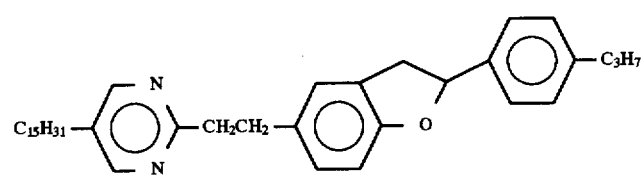 (I-351)
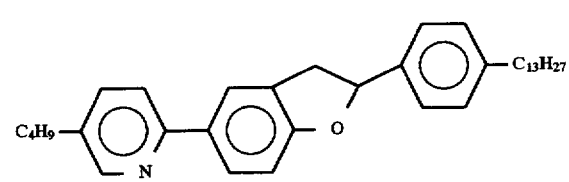 (I-352)
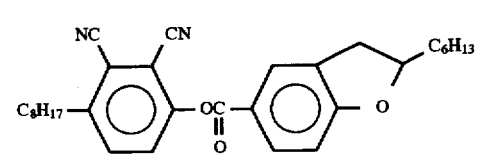 (I-353)
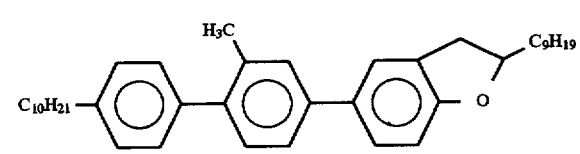 (I-354)
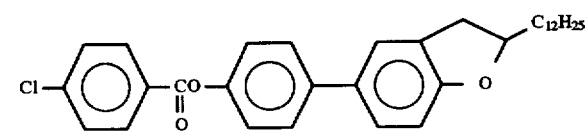 (I-355)
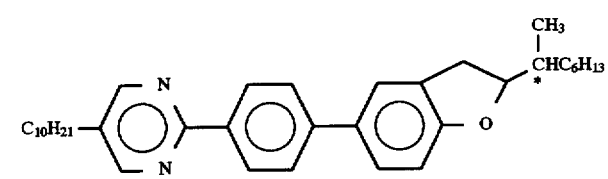 (I-356)
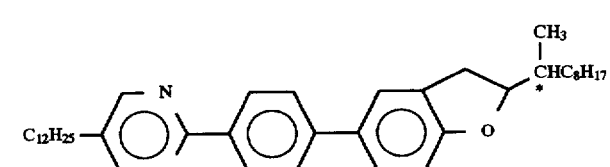 (I-357)

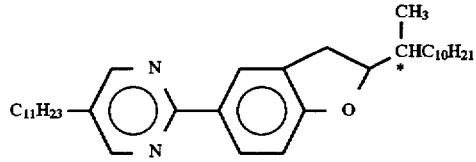 (I-358)
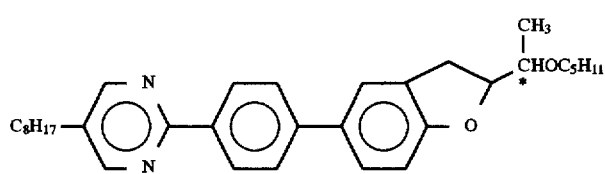 (I-359)
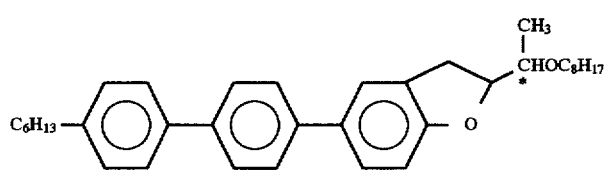 (I-360)
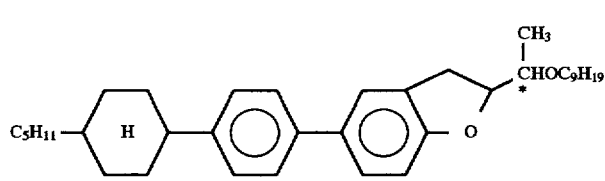 (I-361)
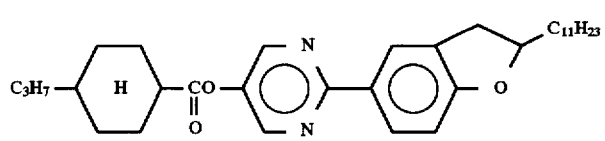 (I-362)
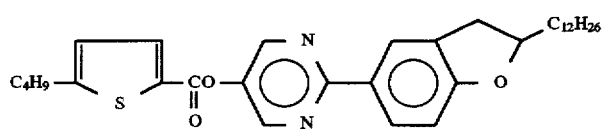 (I-363)
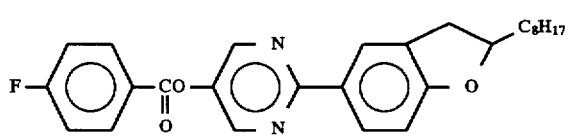 (I-364)
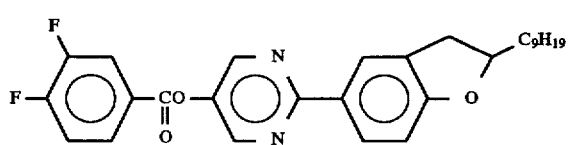 (I-365)
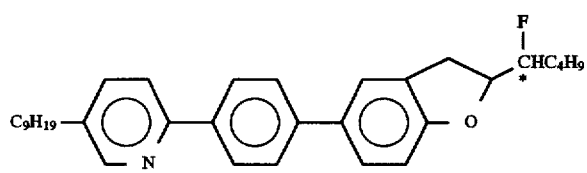 (I-366)
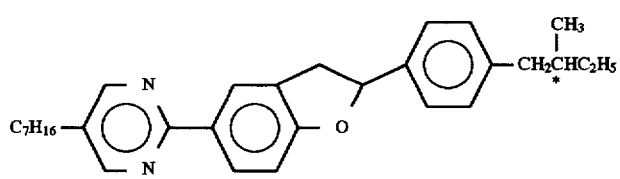 (I-367)

-continued
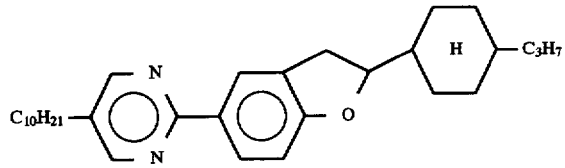 (I-368)
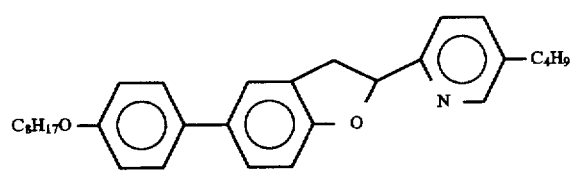 (I-369)
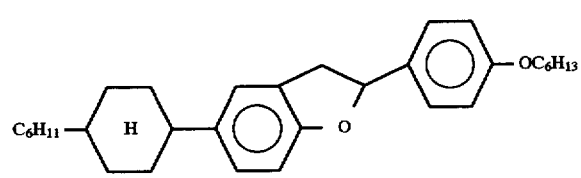 (I-370)
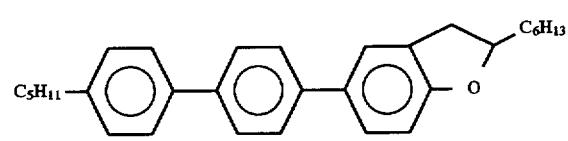 (I-371)
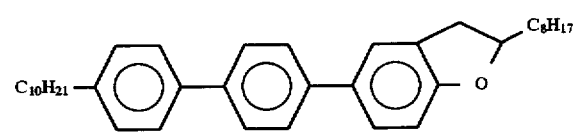 (I-372)
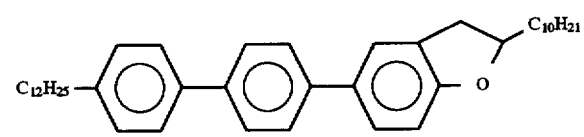 (I-373)
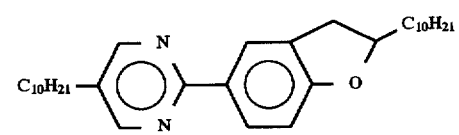 (I-374)
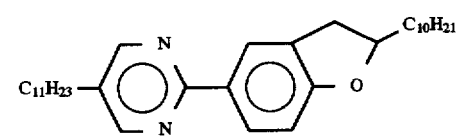 (I-375)
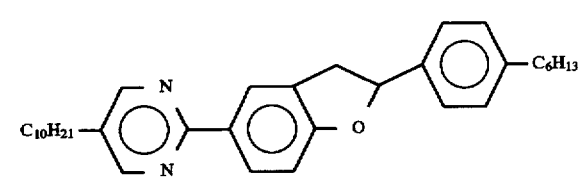 (I-376)
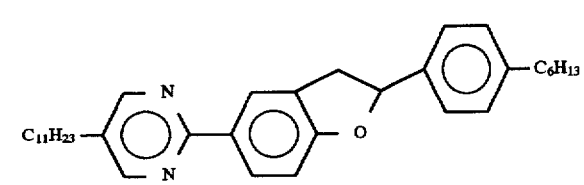 (I-377)

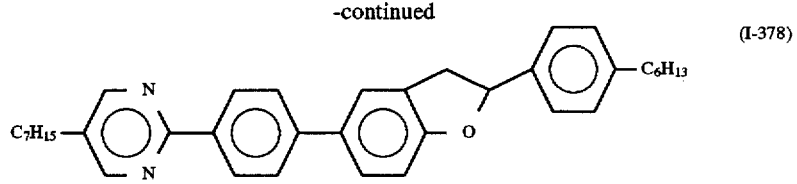 (I-378)
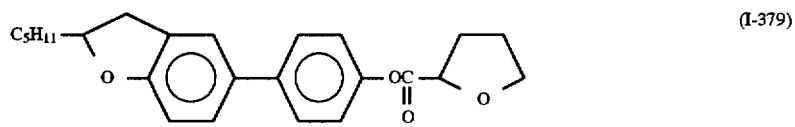 (I-379)
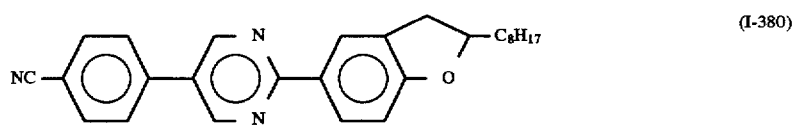 (I-380)
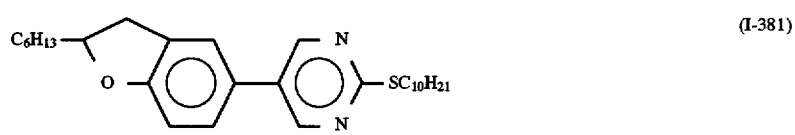 (I-381)
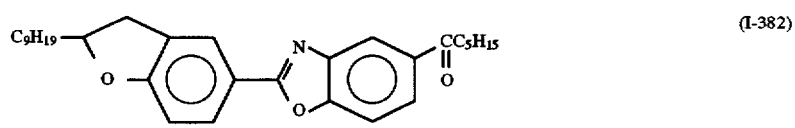 (I-382)
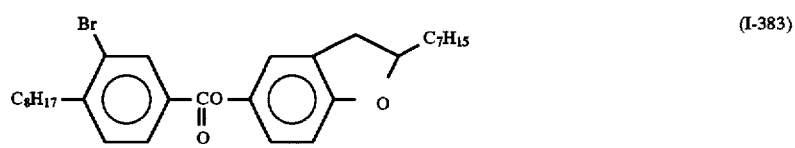 (I-383)
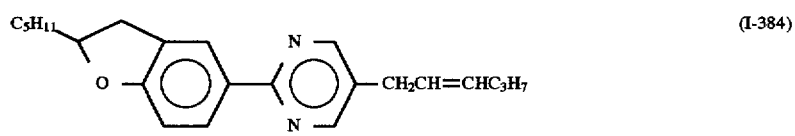 (I-384)
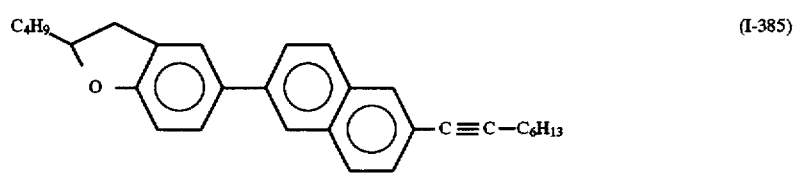 (I-385)
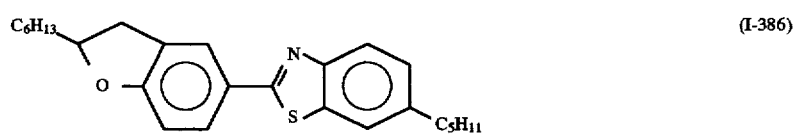 (I-386)
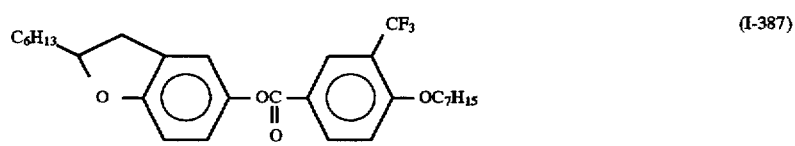 (I-387)
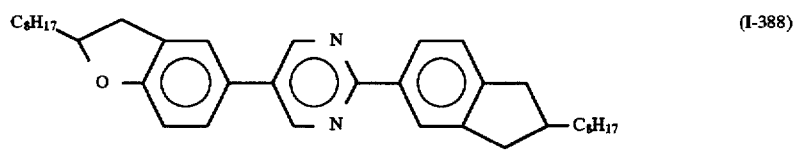 (I-388)

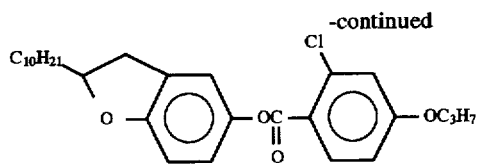

(I-389)

The liquid crystal composition according to the present invention may be obtained by mixing at least one species of the mesomorphic compound represented by the formula (I) and at least one species of another mesomorphic compound in appropriate proportions determined by taking account of the use of a liquid crystal device using the composition, characteristics required therefor, etc.

The liquid crystal composition according to the present invention may preferably be formulated as a liquid crystal composition capable of showing ferroelectricity, particularly a liquid crystal composition showing a chiral smectic phase.

Specific examples of another mesomorphic compound described above may include those denoted by the following formulas (III) to (XIII).

$X_3'$ and $X_4'$ respectively denote a single bond,

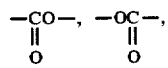

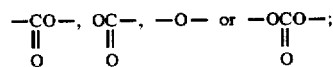 or —$CH_2O$—; and $A_1'$ denotes

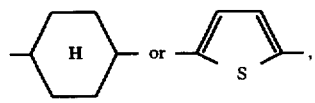

(III)

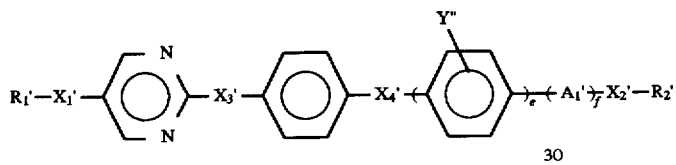

wherein e denotes 0 or 1 and f denotes 0 or 1 with proviso that e+f=0 or 1; Y" denotes H, halogen, $CH_3$ or $CF_3$; $X_1'$ and $X_2'$ respectively denote a single bond, In the formula (III), preferred compounds thereof may include those represented by the following formulas (IIIa) to (IIIe):

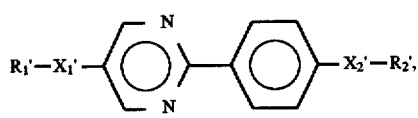 (IIIa)

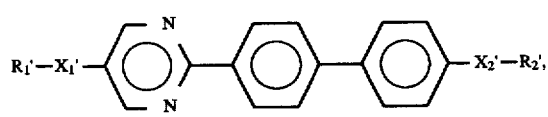 (IIIb)

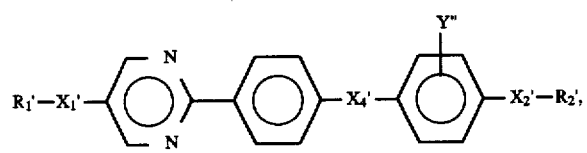 (IIIc)

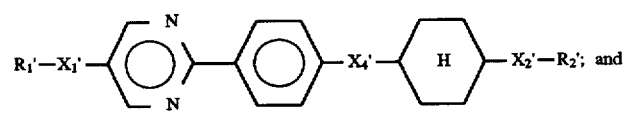 (IIId)

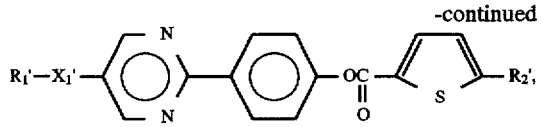
(IIIc)

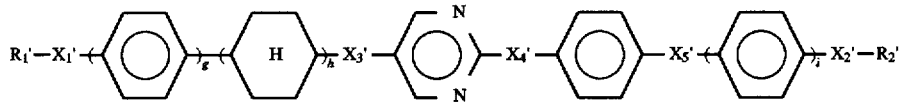
(IV)

wherein g and h respectively denote 0 or 1 with proviso that g+h=0 or 1; i denotes 0 or 1; $X_1'$ and $X_2'$ respectively denote a single bond, $$-\underset{\underset{O}{\parallel}}{C}O-,\ -O\underset{\underset{O}{\parallel}}{C}-,$$

—O— or $$\underset{\underset{O}{\parallel}}{OC}O-;$$

and $X_3'$, $X_4'$ and $X_5'$ respectively denote a single bond, $$-\underset{\underset{O}{\parallel}}{C}O-,\ \underset{\underset{O}{\parallel}}{OC}-,$$

$CH_2O$ or $—OCH_2—$.

In the formula (IV), preferred compounds thereof may include those represented by the following formulas (IVa) to (IVc):

$$-\underset{\underset{O}{\parallel}}{C}O-,\ -O\underset{\underset{O}{\parallel}}{C}-,\ -O-\text{ and }-O\underset{\underset{O}{\parallel}}{C}O-;$$

and $X_3'$ and $X_4'$ respectively denote a single bond, $$-\underset{\underset{O}{\parallel}}{C}O-,\ -O\underset{\underset{O}{\parallel}}{C}-,\ -CH_2O-,\ -OCH_2-,\ CH_2CH_2-,$$

$$-\underset{\underset{O}{\parallel}}{C}S-,\ -S\underset{\underset{O}{\parallel}}{C}-,\ (CH_2)_2\underset{\underset{O}{\parallel}}{C}S-,\ -(CH_2)_i\underset{\underset{O}{\parallel}}{C}O-,$$

$$-CH=CH-\underset{\underset{O}{\parallel}}{C}O-\text{ or }-O-.$$

In the formula (v), preferred compounds thereof may include those represented by the following formulas (Va) and (Vb):

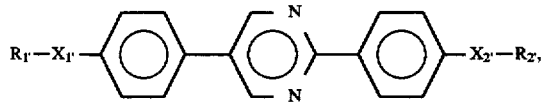
(IVa)

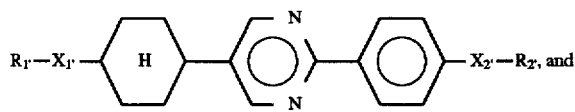
(IVb)

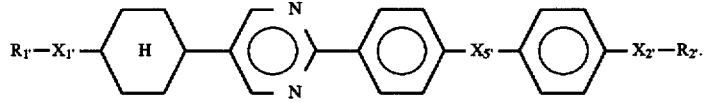
(IVc)

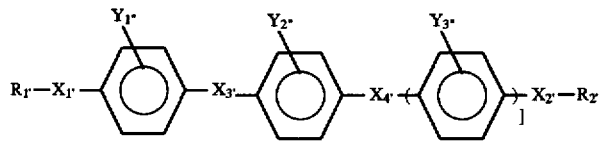
(V)

wherein j denotes 0 or 1; $Y_1''$, $Y_2''$ and $Y_3''$ respectively denote H, halogen, $CH_3$ or $CF_3$; $X_1'$ and $X_2'$ respectively denote a single bond,

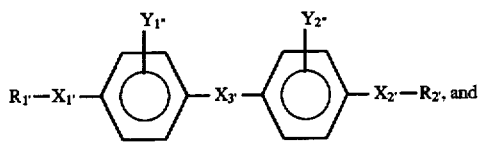  (Va)

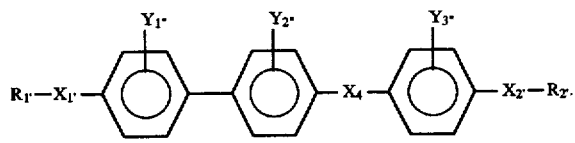  (Vb)

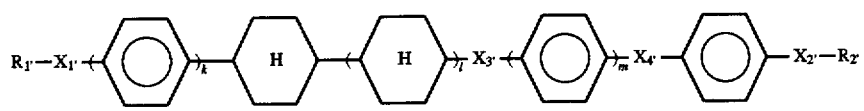  (VI)

wherein k, l and m respectively denote 0 or 1 with proviso that k+l+m=0, 1 or 2; $X_1'$ and $X_2'$ respectively denote a single bond,

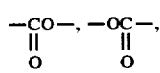

—O— or

and $X_3'$ and $X_4'$ respectively denote a single bond,

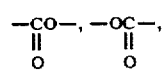

—CH$_2$O or —OCH$_2$—.

In the formula (VI), preferred compounds thereof may include those represented by the following formulas (VIa) to (VIf):

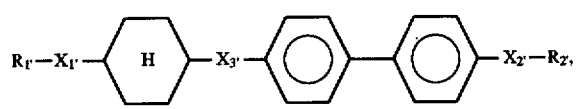  (VIa)

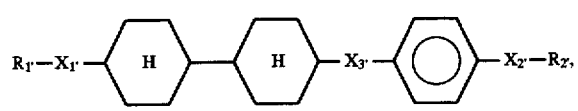  (VIb)

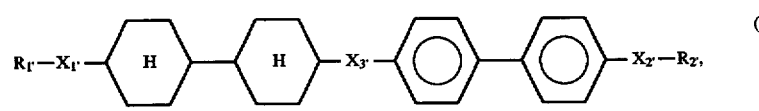  (VIc)

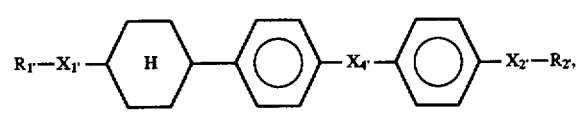  (VId)

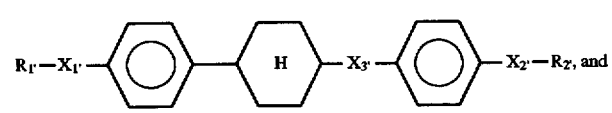  (VIe)

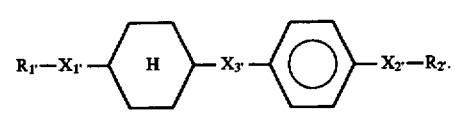  (VIf)

Herein, $R_1'$ and $R_2'$ respectively denote a linear or branched alkyl group having 1-18 carbon atoms capable of including one or non-neighboring two or more methylene groups which can be replaced with —CH halogen- and capable of further including one or two or more non-neighboring methylene groups other than those directly connected to $X_1'$ or $X_2'$ which can be replaced with at least one species of

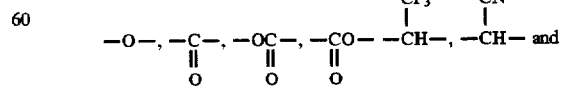

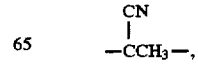

with proviso that $R_1'$ and $R_2'$ respectively do not connect to a ring structure by a single bond when $R_1'$ and $R_2'$ respectively denote a halogenated alkyl group containing one methylene group replaced with —CH halogen- or —CH $(CF_3)$—.

Further, preferred examples of $R_1'$ and $R_2'$ may respectively include those represented by the following groups (i) to (xi):

i) a linear alkyl group having 1-15 carbon atoms;

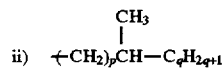

wherein p denotes an integer of 0-5 and q denotes an integer of 2-11 (optically active or inactive);

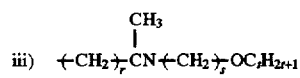

wherein r denotes an integer of 0-6, s denotes 0 or 1, and t denotes an integer of 1-14 (optically active or inactive);

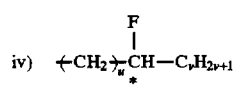

wherein u denotes 0 or 1 and v denotes an integer of 1-16;

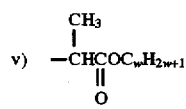

wherein w denotes an integer of 1-15 (optically active or inactive);

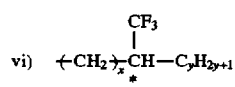

wherein x denotes an integer of 0-2 and y denotes an integer of 1-15;

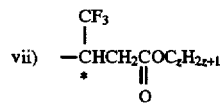

wherein z denotes an integer of 1-15;

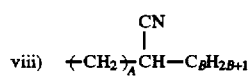

wherein a denotes an integer of 0-2 and B denotes an integer of 1-15 (optically active or inactive);

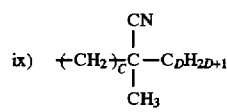

wherein C denotes an integer of 0-2 and D denotes an integer of 1-15 (optically active or inactive).

x) hydrogen (H), and xi) fluorine (F).

In the above-mentioned formulas (IIIa) to (IIId), more preferred compounds thereof may include those represented by the formulas (IIIaa) to (IIIdc):

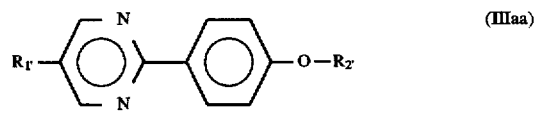 (IIIaa)

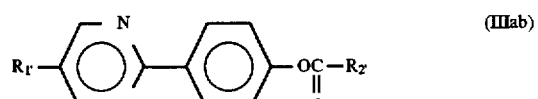 (IIIab)

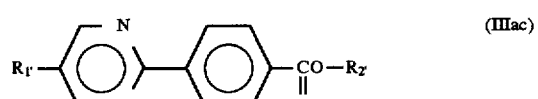 (IIIac)

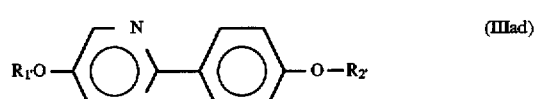 (IIIad)

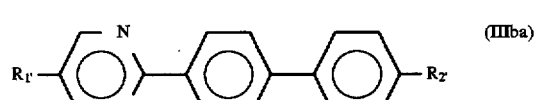 (IIIba)

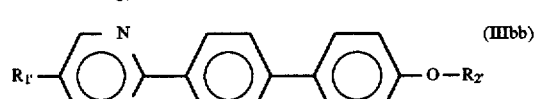 (IIIbb)

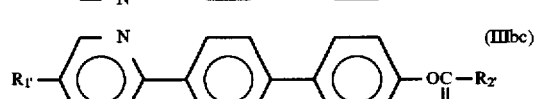 (IIIbc)

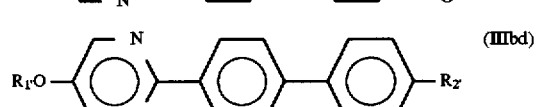 (IIIbd)

 (IIIca)

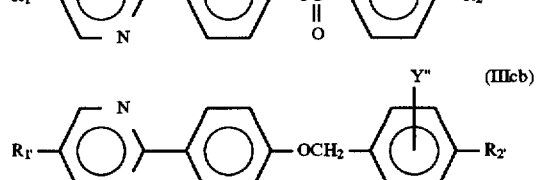 (IIIcb)

-continued
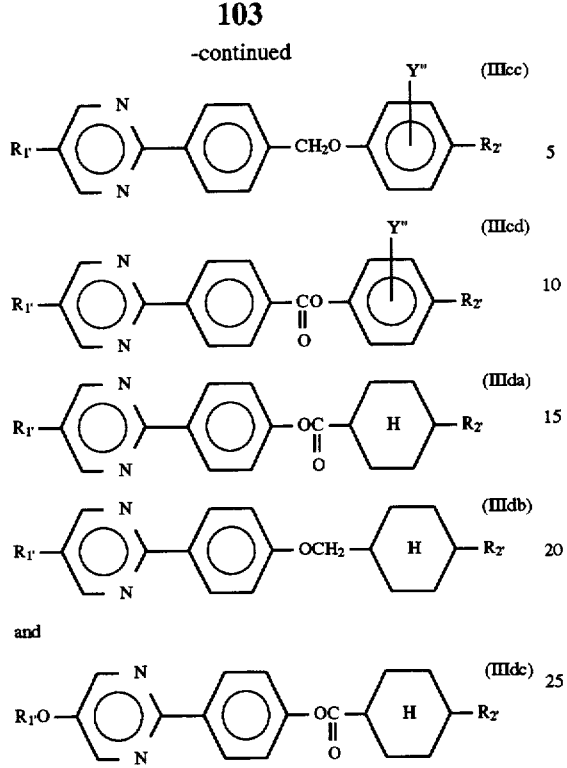
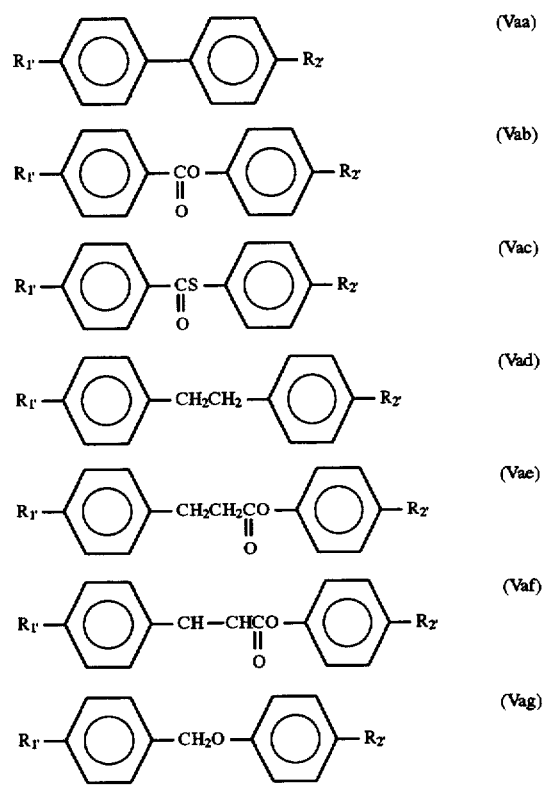
In the above-mentioned formulas (IVa) to (IVc), more preferred compounds thereof may include those represented by the formulas (IVaa) to (IVcb):
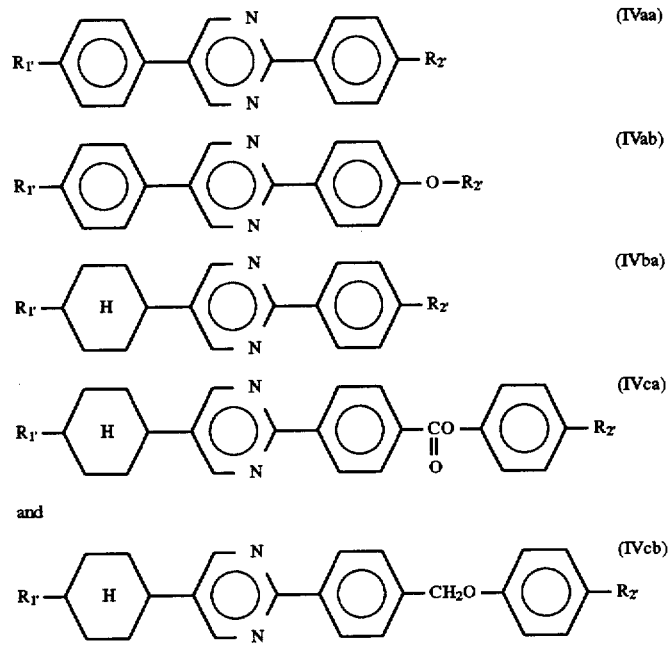
In the above-mentioned formulas (Va) and (Vb), more preferred compounds thereof may include those represented by the formulas (Vaa) to (Vbf):
-continued
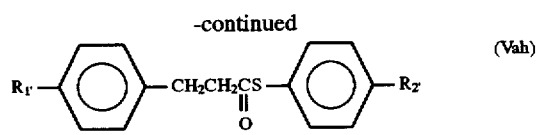

-continued

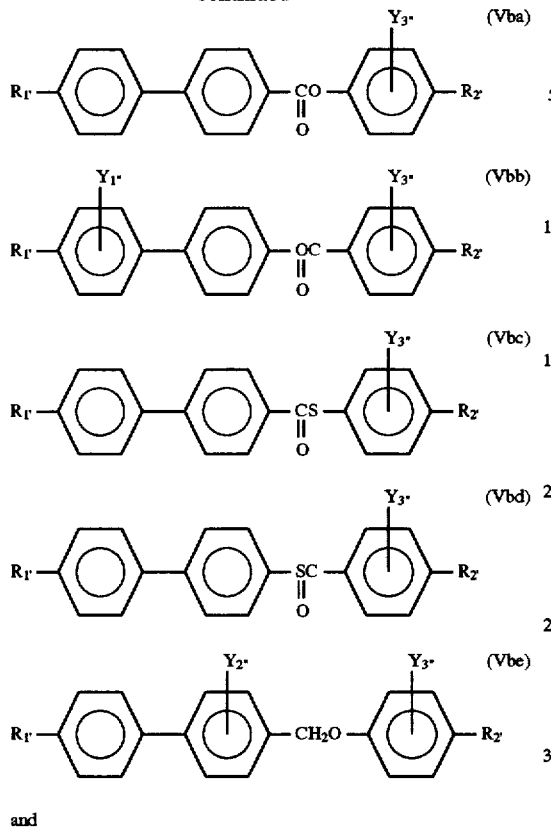

In the above-mentioned formulas (VIa) to (VIf), more preferred compounds thereof may include those represented by the formulas (VIaa) to (VIfa):

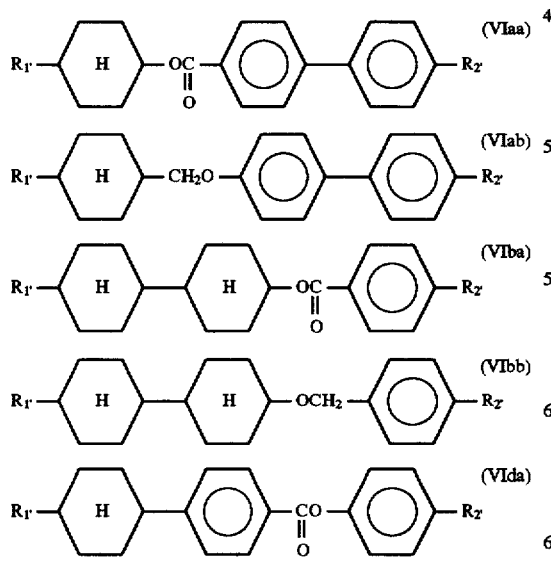

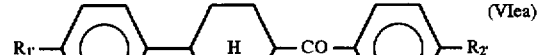

and

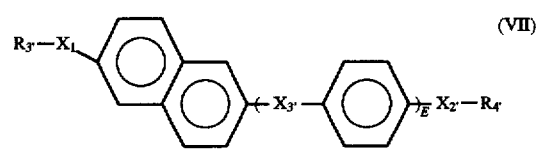

wherein E denotes 0 or 1; $X_1'$ and $X_2'$ respectively denote a single bond,

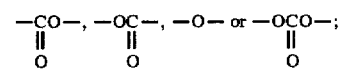

and $X_3'$ denotes a single bond,

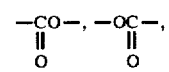

—CH$_2$O— or —OCH$_2$—.

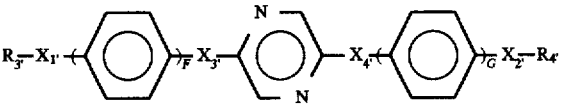

wherein F and G respectively denote 0 or 1; $X_1'$ and $X_2'$ respectively denote a single bond,

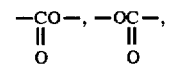

or —O—;

and $X_3'$ and $X_4'$ respectively denote a single bond,

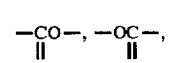

—CH$_2$O— or —OCH$_2$—.

In the above formula (VII), preferred compounds thereof may include those represented by the following formulas (VIIa) and (VIIb):

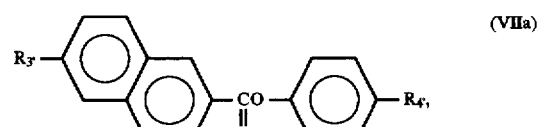

and

-continued

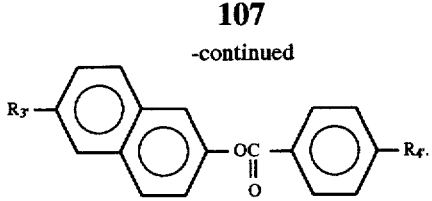  (VIIb)

In the above formula (VIII), preferred compounds thereof may include those represented by the following formulas (VIIIa) and (VIIIb).

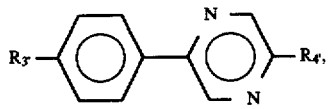  (VIIIa)

and

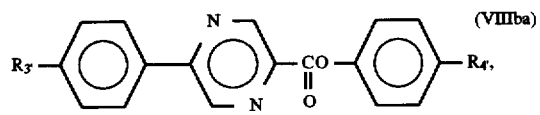  (VIIIb)

More preferred compounds of the formula (VIIIb) may include those represented by the formulas (VIIIba) to (VIIIbb):

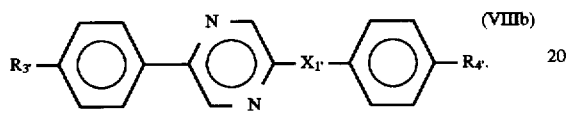  (VIIIba)

and

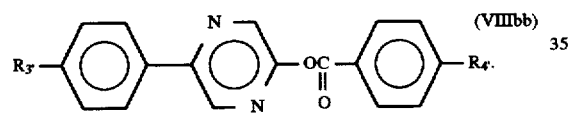  (VIIIbb)

Herein, $R_3{'}$ and $R_4{'}$ respectively denote a linear or branched alkyl group having 1-18 carbon atoms capable of including one or non-neighboring two or more methylene groups which can be replaced with —CH halogen- and capable of further including one or two or more non-neighboring methylene groups other than those directly connected to $X_1{'}$ or $X_2{'}$ which can be replaced with at least one species of —O—,

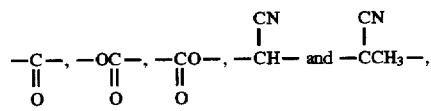

with proviso that $R_3{'}$ and $R_4{'}$ respectively do not connect to a ring structure by a single bond when $R_3{'}$ and $R_4{'}$ respectively denote a halogenated alkyl group containing one methylene group replaced with —CH halogen-.

Further, preferred examples of $R_3{'}$ and $R_4{'}$ may respectively include those represented by the following groups (i) to (vii):

i) a linear alkyl group having 1-15 carbon atoms;

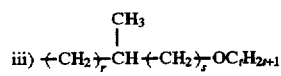

wherein p denotes an integer of 0-5 and q denotes an integer of 2-11 (optically active or inactive);

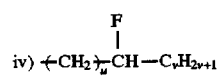

wherein r denotes an integer of 0-6, s denotes 0 or 1, and t denotes an integer of 1-14 (optically active or inactive);

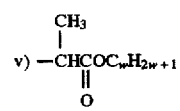

wherein u denotes an integer of 0 or 1 and v denotes an integer of 1-16 (optically active or inactive);

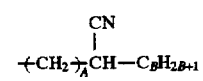

wherein w denotes an integer of 1-15 (optically active or inactive);

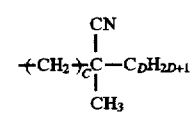

wherein A denotes an integer of 0-2 and B denotes an integer of 1-15 (optically active or inactive); and

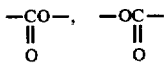

wherein C denotes an integer of 0-2 and D denotes an integer of 1-15 (optically active or inactive).

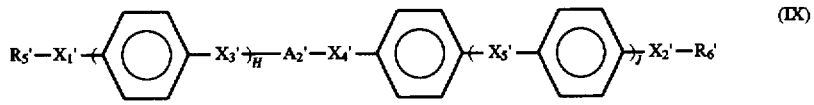  (IX)

wherein H and J respectively denote 0 or 1 with proviso that H+J=0 or 1; $X_1{'}$ and $X_2{'}$ respectively denote a single bond, $$-CO-, \quad -OC-$$
$$\parallel \quad\quad \parallel$$
$$O \quad\quad O$$

or —O—; $A_2{'}$ denotes

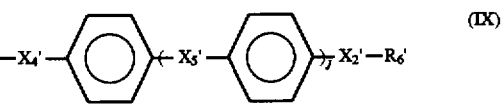

and $X_3'$ and $X_4'$ respectively denote a single bond,

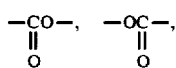

—$CH_2O$— or —$OCH_2$—.

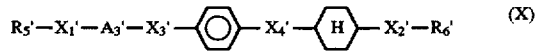 (X)

wherein $X_1'$ and $X_2'$ respectively denote a single bond,

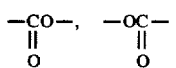

or —O—; $A_3'$ denotes

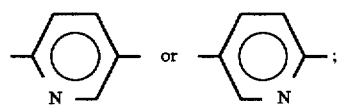

and $X_3'$ and $X_4'$ respectively denote a single bond,

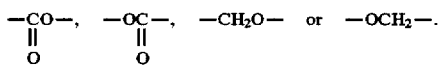

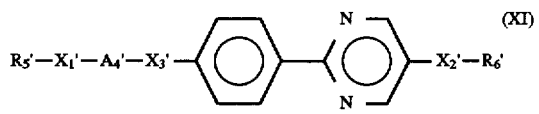 (XI)

wherein $X_1'$ and $X_2'$ respectively denote a single bond,

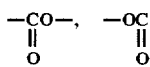

or —O—; $A_4'$ denotes

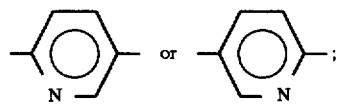

and $X_3'$ respectively denotes a single bond,

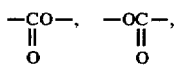

—$CH_2O$— or —$OCH_2$—.

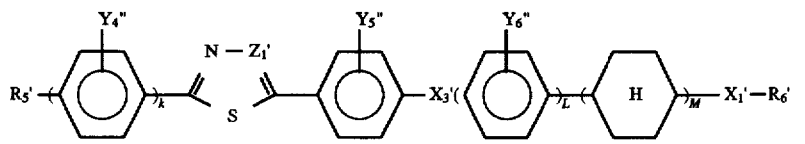 (XII)

wherein K, L and M respectively denote 0 or 1 with the proviso that K+L+M=0 or 1; $X_1'$ denotes a single bond,

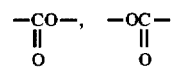

or —O—; $X_3'$ denotes a single bond,

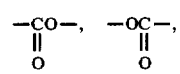

—$CH_2O$— or —$OCH_2$—; $Y_4"$, $Y_5"$ and $Y_6"$ respectively denote H or F; and $Z_1'$ CH or N.

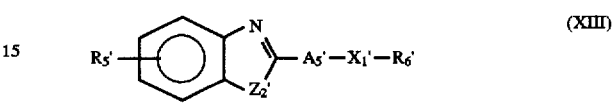 (XIII)

wherein $Z_2'$ denotes —O— or —S—; and $A_5'$ denotes

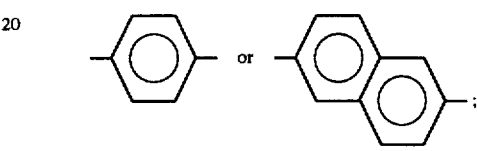

$X_1$ denotes a single bond,

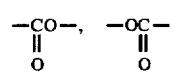

or —O—.

In the above formula (IX), preferred compounds thereof may include those represented by the following formulas (IXa) to (IXc):

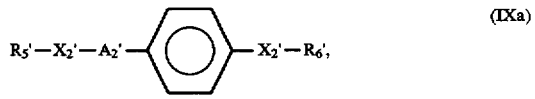 (IXa)

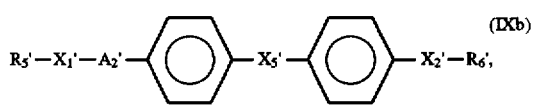 (IXb)

and

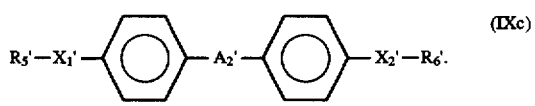 (IXc)

In the above formula (X), preferred compounds thereof may include those represented by the following formulas (Xa) and (Xb):

 (Xa)

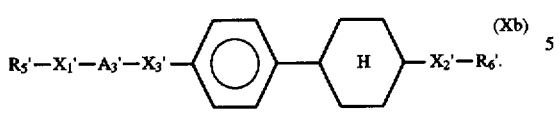
(Xb)

In the above formula (XII), preferred compounds thereof may include those represented by the following formulas (XIIa) and (XIII):

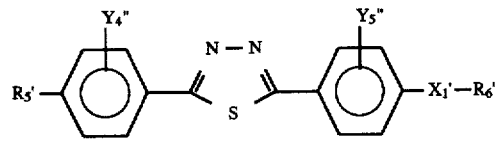
(XIIa)

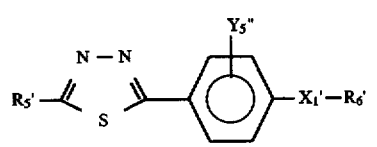
(XIIb)

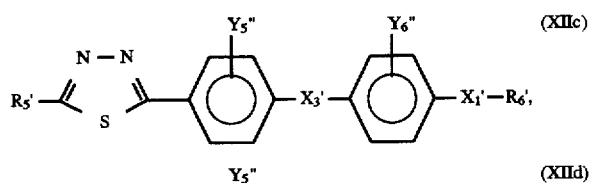
(XIIc)

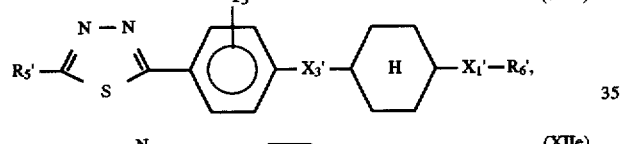
(XIId)

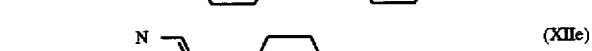
(XIIe)

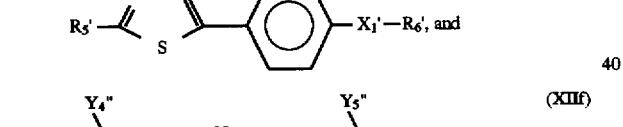
(XIIf)

In the above formula (XIII), preferred compounds thereof may include those represented by the following formulas (XIIIa) to (XIIIe):

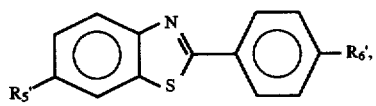
(XIIIa)

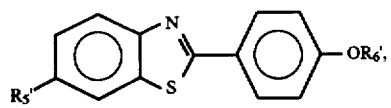
(XIIIb)

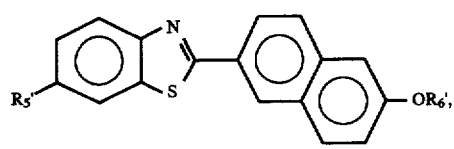
(XIIIc)

(XIIId)

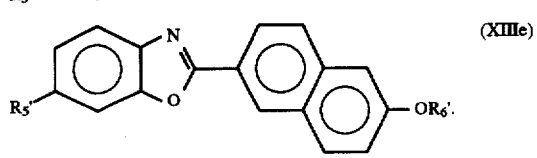
(XIIIe)

In the above-mentioned formulas (IXa) to (IXc), more preferred compounds thereof may include those represented by the formulas (IXaa) to (IXcc):

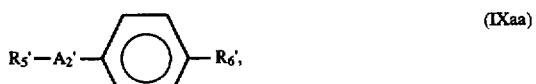
(IXaa)

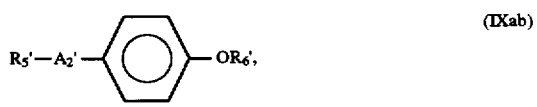
(IXab)

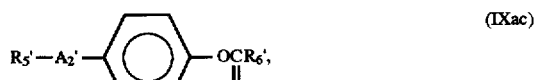
(IXac)

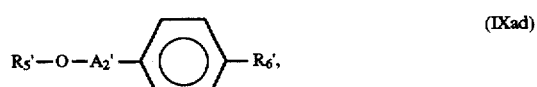
(IXad)

(IXba)

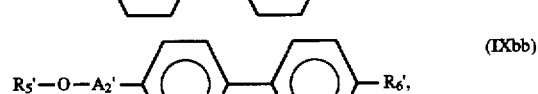
(IXbb)

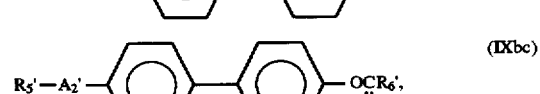
(IXbc)

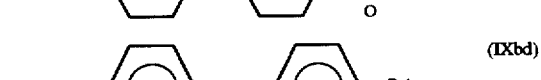
(IXbd)

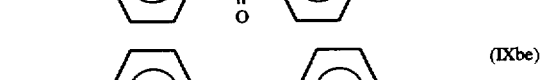
(IXbe)

(IXca)

(IXcb)

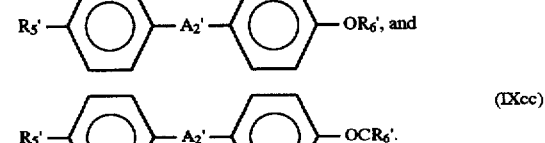
(IXcc)

In the above-mentioned formulas (Xa) to (Xb), more preferred compounds thereof may include those represented by the formulas (Xaa) to (Xbb):

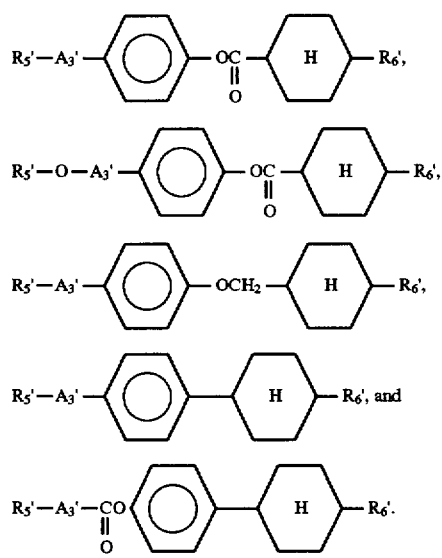

In the above formula (XI), preferred compounds thereof may include those represented by the following formulas (XIa) to (XIg):

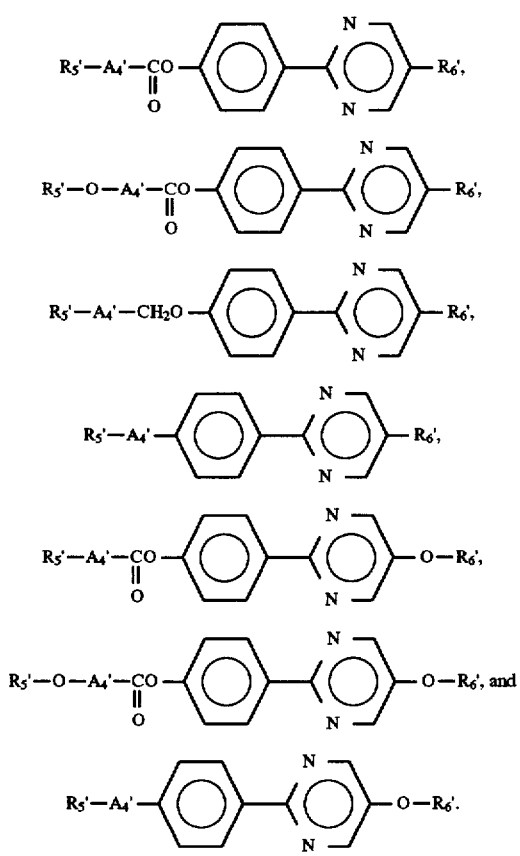

In the above-mentioned formulas (XIIa) to (XIIf), more preferred compounds thereof may include those represented by the formula (XIIaa) to (XIIdb):

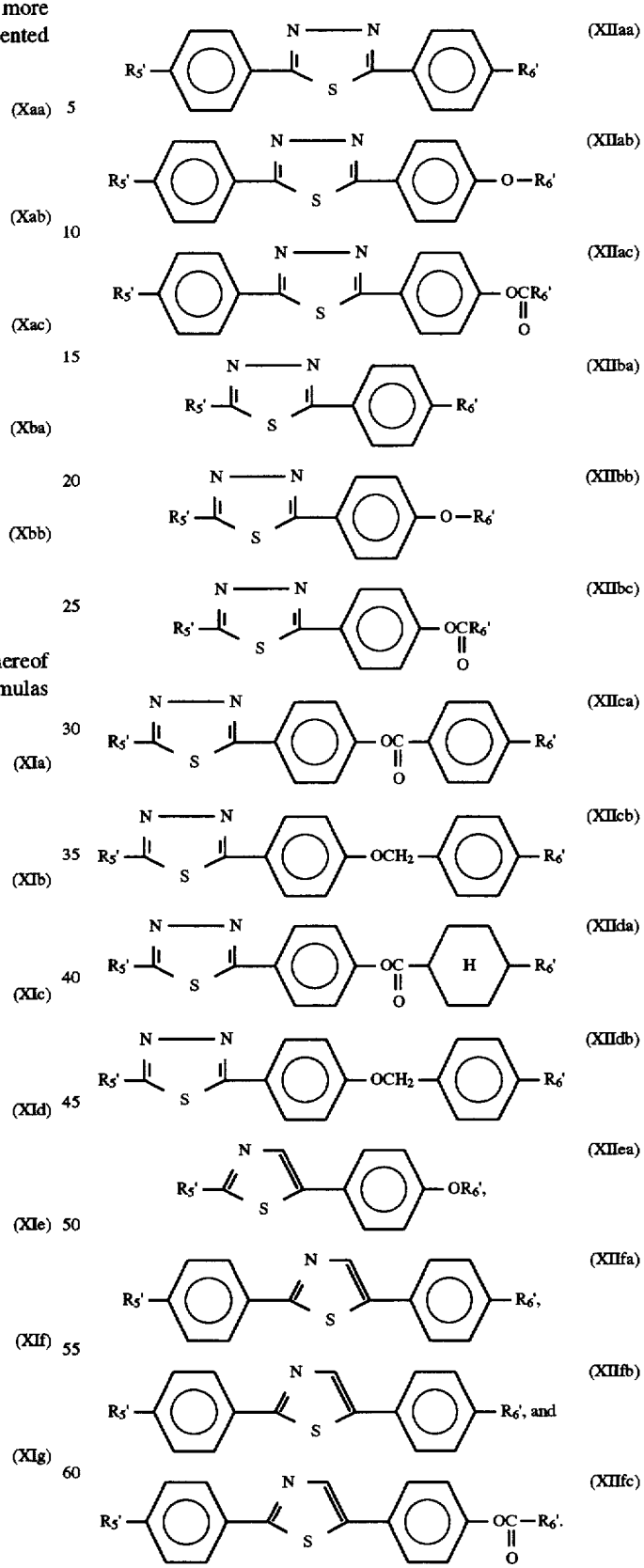

Herein, $R_5'$ and $R_6'$ respectively denote a linear or branched alkyl group having 1–18 carbon atoms capable of including one non-neighboring two or more methylene groups other than those directly connected to $X_1'$ or $X_2'$ which can be replaced with at least one species of —O—,

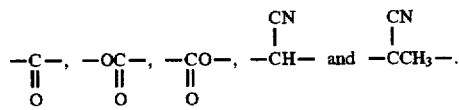

Further, preferred examples of $R_5'$ and $R_6'$ may respectively include those represented by the following groups (i) to (vi):

i) a linear alkyl group having 1–15 carbon atoms:

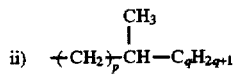

wherein p denotes an integer of 0–5 and q denotes an integer of 2–11 (optically active or inactive);

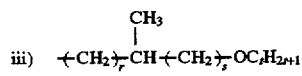

wherein r denotes an integer of 0–6, s denotes 0 or 1, and t denotes an integer of 1–14 (optically active or inactive);

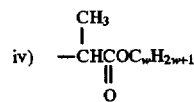

wherein w denotes an integer of 1–15 (optically active or inactive);

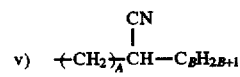

wherein A denotes an integer of 0–2 and B denotes an integer of 1–15 (optically active or inactive); and

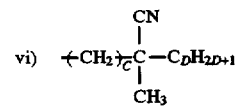

wherein C denotes an integer of 0–2 and D denotes an integer of 1–15 (optically active or inactive).

In formulating the liquid crystal composition according to the present invention, the liquid crystal composition may desirably contain 1–80 wt. %, preferably 1–60 wt. %, more preferably 1–40 wt. % of a mesomorphic compound represented by the formula (I).

Further, when two or more species mesomorphic compounds represented by the formula (I) are used, the liquid crystal composition may desirably contain 1–80 wt. %, preferably 1–60 wt. %, more preferably 1–40 wt. %, of the two or more species of the mesomorphic compounds represented by the formula (I).

The liquid crystal device according to the present invention may preferably be prepared by heating the liquid crystal composition prepared as described above into an isotropic liquid under vacuum, filling a blank cell comprising a pair of oppositely spaced electrode plates with the composition, gradually cooling the cell to form a liquid crystal layer and restoring the normal pressure.

FIG. 1 is a schematic sectional view of an embodiment of the liquid crystal device utilizing ferroelectricity prepared as described above for explanation of the structure thereof.

Referring to FIG. 1, the liquid crystal device includes a liquid crystal layer 1 assuming a chiral smectic phase disposed between a pair of glass substrates 2 each having thereon a transparent electrode 3 and an insulating alignment control layer 4. The glass substrates 2 are placed or arranged opposite each other. Lead wires 6 are connected to the electrodes so as to apply a driving voltage to the liquid crystal layer 1 from a power supply 7. Outside the substrates 2, a pair of polarizers 8 are disposed so as to modulate incident light 10 from a light source 9 in cooperation with the liquid crystal i to provide modulated light I.

Each of two glass substrates 2 is coated with a transparent electrode 3 comprising a film of $In_2O_3$, $SnO_2$ or ITO (indium-tin-oxide) to form an electrode plate. Further thereon, an insulating alignment control layer 4 is formed by rubbing a film of a polymer such as polyimide with gauze or acetate fiber-planted cloth so as to align the liquid crystal molecules in the rubbing direction. Further, it is also possible to compose the alignment control layer of two layers, e.g., by first forming an insulating layer of an inorganic material, such as silicon nitride, silicon carbide containing hydrogen, silicon oxide, boron nitride, boron nitride containing hydrogen, cerium oxide, aluminum oxide, zirconium oxide, titanium oxide, or magnesium fluoride, and forming thereon an alignment control layer of an organic insulating material, such as polyvinyl alcohol, polyimide, polyamide-imide, polyester-imide, polyparaxylyene, polyester, polycarbonate, polyvinyl acetal, polyvinyl chloride, polyvinyl acetate, polyamide, polystyrene, cellulose resin, melamine resin, urea resin, acrylic resin, or photoresist resin. Alternatively, it is also possible to use a single layer of inorganic insulating alignment control layer or organic insulating alignment control layer. An inorganic insulating alignment control layer may be formed by vapor deposition, while an organic insulating alignment control layer may be formed by applying a solution of an organic insulating material or a precursor thereof in a concentration of 0.1 to 20 wt. %, preferably 0.2–10 wt. %, by spinner coating, dip coating, screen printing, spray coating or roller coating, followed by curing or hardening under prescribed hardening condition (e.g., by heating). The insulating alignment control layer 4 may have a thickness of ordinarily 10 Å–1 micron, preferably 10–3000 Å, further preferably 10–1000 Å. The two glass substrates 2 with transparent electrodes 3 (which may be inclusively referred to herein as "electrode plates") and further with insulating alignment control layers 4 thereof are held to have a prescribed (but arbitrary) gap with a spacer 5. For example, such a cell structure with a prescribed gap may be formed by sandwiching spacers of silica beads or alumina beads having a prescribed diameter with two glass plates, and then sealing the periphery thereof with, e.g., an epoxy adhesive. Alternatively, a polymer film or glass fiber may also be used as a spacer. Between the two glass plates, a liquid crystal composition assuming a chiral smectic phase is sealed up to provide a liquid crystal layer 1 in a thickness of generally 0.5 to 20 μm, preferably 1 to 5 μm.

The transparent electrodes 3 are connected to the external power supply 7 through the lead wires 6. Further, outside the glass substrates 2, polarizers 8 are, applied. The device shown in FIG. 1 is of a transmission type and is provided with a light source 9.

FIG. 2 is a schematic illustration of a liquid crystal cell (device) utilizing ferroelectricity for explaining operation thereof. Reference numerals 21a and 21b denote substrates (glass plates) on which a transparent electrode of, e.g., $In_2O_3$, $SnO_2$, ITO (indium-tin-oxide), etc., is disposed, respectively. A liquid crystal of an SmC*-phase (chiral smectic C phase) or SmH*-phase (chiral smectic II phase) in which liquid crystal molecular layers 22 are aligned perpendicular to surfaces of the glass plates is hermetically disposed therebetween. Lines 23 show liquid crystal molecules. Each liquid crystal molecule 23 has a dipole moment (P⊥) 24 in a direction perpendicular to the axis thereof. The liquid crystal molecules 23 continuously form a helical structure in the direction of extension of the substrates. When a voltage higher than a certain threshold level is applied between electrodes formed on the substrates 21a and 21b, a helical structure of the liquid crystal molecule 23 is unwound or released to change the alignment direction of respective liquid crystal molecules 23 so that the dipole moments (P⊥) 24 are all directed in the direction of the electric field. The liquid crystal molecules 23 have an elongated shape and show refractive anisotropy between the long axis and the short axis thereof. Accordingly, it is easily understood that when, for instance, polarizers arranged in a cross nicol relationship, i.e., with their polarizing directions crossing each other, are disposed on the upper and the lower surfaces of the glass plates, the liquid crystal cell thus arranged functions as a liquid crystal optical modulation device of which optical characteristics vary depending upon the polarity of an applied voltage.

Further, when the liquid crystal cell is made sufficiently thin (e.g., less than about 10 microns), the helical structure of the liquid crystal molecules is unwound to provide a non-helical structure even in the absence of an electric field, whereby the dipole moment assumes either of the two states, i.e., Pa in an upper direction 34a or Pb in a lower direction 34b as shown in FIG. 3, thus providing a bistable condition. When an electric field Ea or Eb higher than a certain threshold level and different from each other in polarity as shown in FIG. 3 is applied to a cell having the above-mentioned characteristics by using voltage application means 31a and 31b, the dipole moment is directed either in the upper direction 34a or in the lower direction 34h depending on the vector of the electric field Ea or Eb. In correspondence with this, the liquid crystal molecules are oriented in either of a first stable state 33a and a second stable state 33b.

When the above-mentioned ferroelectric liquid crystal is used as an optical modulation element, it is possible to obtain two advantages. First is that the response speed is quite fast. Second is that the orientation of the liquid crystal shows bistability. The second advantage will be further explained, with reference to FIG. 3. When the electric field Ea is applied to the liquid crystal molecules, they are oriented in the first stable state 33a. This state is stably retained even if the electric field is removed. On the other hand, when the electric field Eb of which direction is opposite to that of the electric field Ea is applied thereto, the liquid crystal molecules are oriented to the second stable state 33b, whereby the directions of molecules are changed. This state is similarly stably retained even if the electric field is removed. Further, as long as the magnitude of the electric field Ea or Eb being applied is not above a certain threshold value, the liquid crystal molecules are placed in the respective orientation states.

Figure 4:
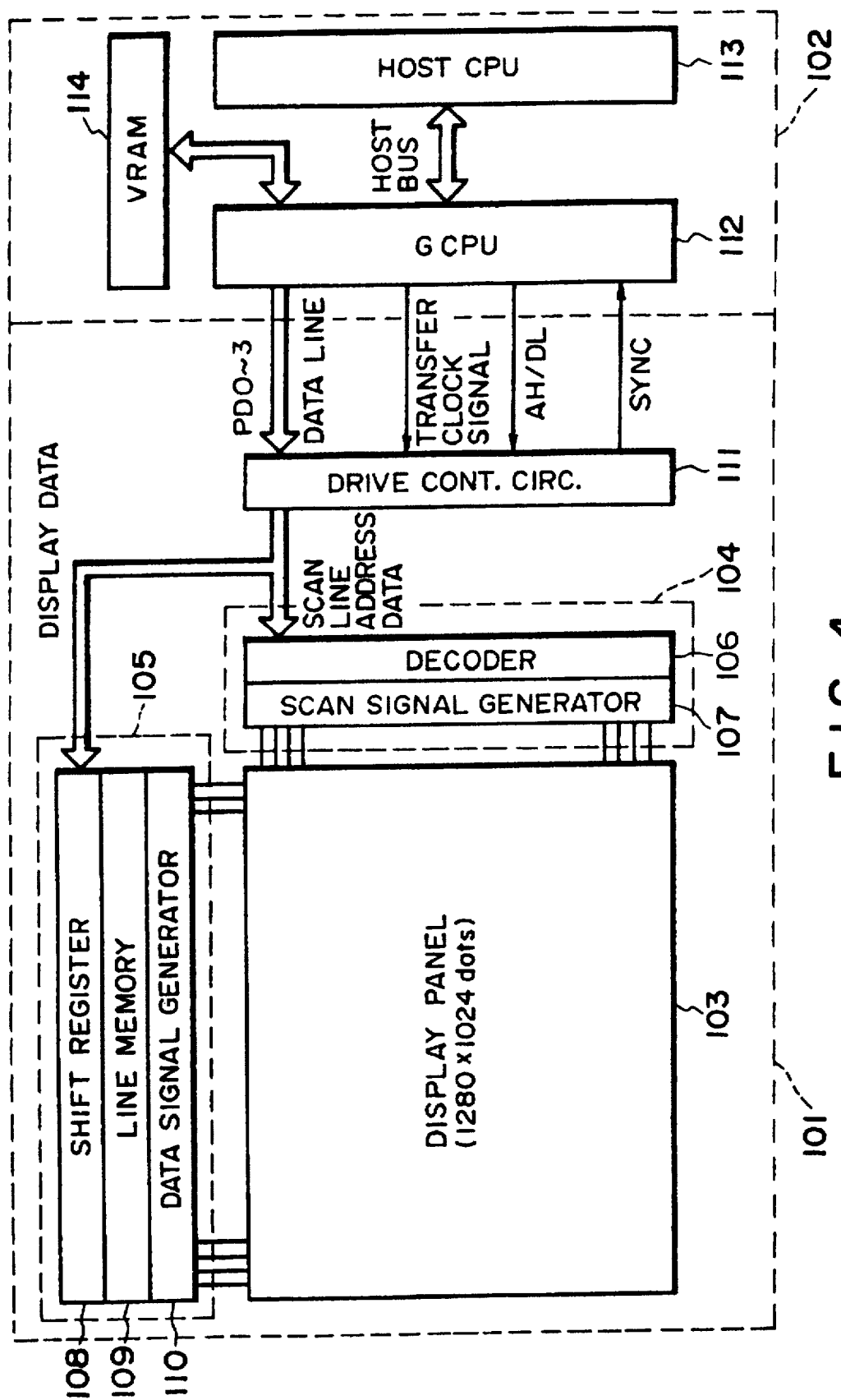
FIG. 4 is a block diagram showing a display apparatus comprising a liquid crystal device utilizing ferroelectricity of a liquid crystal composition and a graphic controller.
Figure 5:
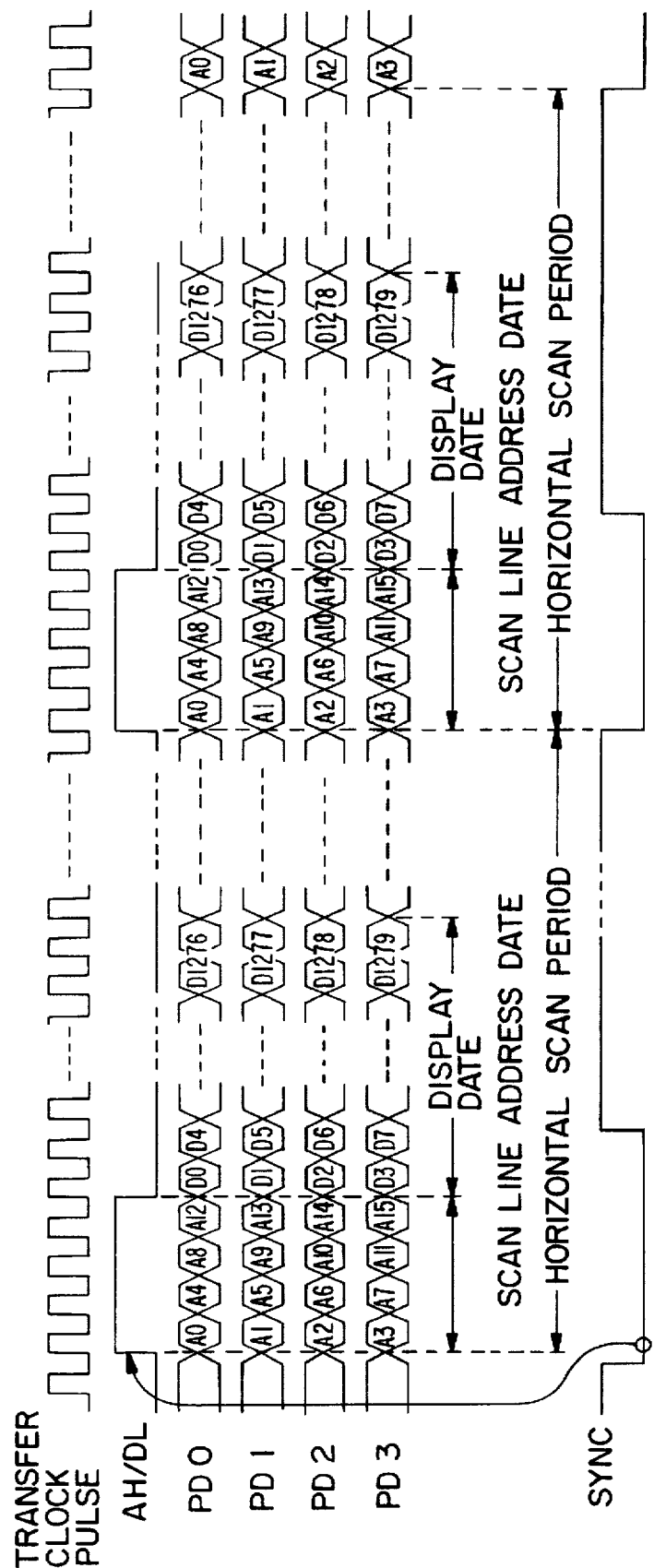
FIG. 5 is a time chart of image data communication showing time correlation between signal transfer and driving with respect to u liquid crystal display apparatus and a graphic controller.

Based on an arrangement appearing hereinbelow and data format comprising image data accompanied with scanning line address data and by adopting communication synchronization using a SYNC signal as shown in FIGS. 4 and 5, there is provided a liquid crystal display apparatus of the present invention which uses the liquid crystal device according to the present invention as a display panel portion.

Referring to FIG. 4, the ferroelectric liquid crystal display apparatus 101 includes a graphic controller 102, a display panel 103, a scanning line drive circuit 104, a data line drive circuit 105, a decoder 106, a scanning signal generator 107, a shift resistor 108, a line memory 109, a data signal generator 110, a drive control circuit 111, a graphic central processing unit (GCPU) 112, a host central processing unit (host CPU) 113, and an image data storage memory (VRAM) 114.

Image data are generated in the graphic controller 102 in an apparatus body and transferred to a display panel 103 by signal transfer means. The graphic controller 102 principally comprises a CPU (central processing unit, hereinafter referred to as "GCPU") 112 and a VRAM (video-RAM, image data storage memory) 114 and is in charge of management and communication of image data between a host CPU 113 and the liquid crystal display apparatus (FLCD) 101. The control of the display apparatus is principally realized in the graphic controller 102. A light source is disposed at the back of the display panel 103.

Hereinbelow, the present invention will be explained more specifically with reference to examples. It is however to be understood that the present invention is not restricted to these examples.

EXAMPLE 1

Production of 5-(5-decylpyrimidine-2-yl)phenyl 2-octylcoumaran Example Compound (Ex. Comp. No. I-15)
Step i)

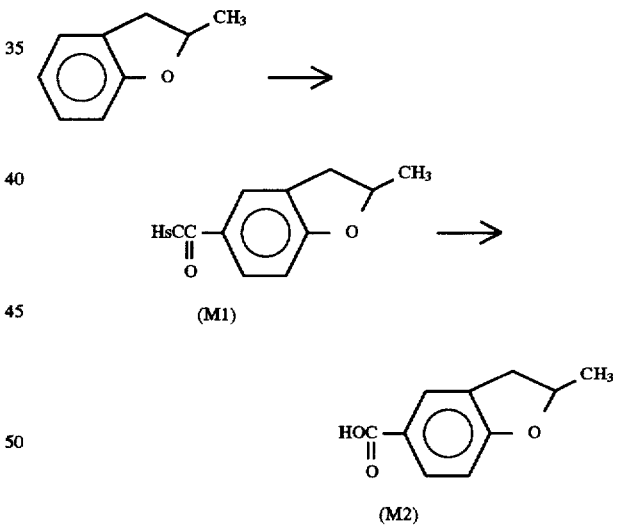

5.00 g (37.3 mM) of 2-methylcoumaran was dissolved in 80 ml of dry carbon disulfide. To the solution, 6.13 g (46.0 mM) of powdered aluminum chloride anhydride was added under cooling on an ice-common salt bath. To the mixture, 2.88 ml (40.5 mM) of acethyl chloride was gradually added dropwise at −3.5° to −1.5° C. under cooling on the bath, followed by stirring for 45 minutes at the same temperature. After the reaction, the reaction mixture was poured into a mixture of 100 g of ice and 30 ml of hydrochloric acid, followed by extraction with ethyl acetate. The organic layer was washed with water and dried with mirabilite, followed by further drying under reduced pressure to obtain 6.70 g of oily 5-acetyl-2-methylcoumaran (M1).

On an ice-common salt bath, 6.25 ml of bromine was added dropwise to a solution of 15.1 g of sodium hydroxide in 100 ml of water under stirring and cooling. To a solution of 6.50 g of 5-acetyl-2-methyl coumaran (M1) in 100 ml of dioxane, the above mixture (i.e., hypobromous acid solution) was added dropwise at 3°–8° C. under cooling on an ice bath. The ice bath was removed after the addition. The resultant mixture was stirred for 3.5 hours at room temperature. After the reaction, the reaction mixture was poured into 500 ml of ice water, followed by addition of 30 ml of hydrochloric acid to precipitate a crystal. The crystal was recovered by filtration and washed with water. The resultant crystal was dried under reduced pressure, followed by washing with hexane and isopropyl ether successively to obtain 3.77 g of 5-carboxy-2-methylcoumaran (M2) (Yield: 57.4%).

Step ii)

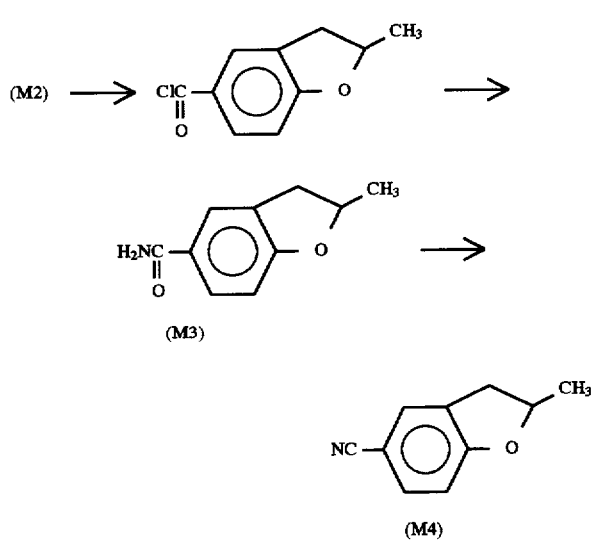

In a 30 ml-round bottomed flask, 3.70 g (20.8 mM) of 5-carboxy-2-methylcoumaran was placed, followed by addition of 8.0 ml of thionyl chloride and one drop of N,N-dimethyl]formamide (DMF). The mixture was stirred for 10 minutes under refluxing. An excessive thionyl chloride was distilled off under reduced pressure to obtain an acid chloride. Under stirring and cooling on an ice bath, a solution of the acid chloride in 30 ml of dioxane was gradually added dropwise to a mixture of 15 ml of 28%-ammonia water and 5 ml of dioxane, followed by stirring for 55 minutes under cooling on the ice bath. After the reaction, 250 ml of water was added to the reaction mixture to precipitate a crystal. The crystal was recovered by filtration and washed with water, followed by recrystallization from methanol to obtain 2.29 g of 5-carbamoyl-2-methylcoumaran (M3) (Yield: 62.2%).

Then, 6.52 g (24.9 mM) of triphenylphosphine, 18 ml of carbon tetrachloride and 10 ml of tetrahydrofuran (THF) were placed in a 100 ml-three-necked flask. To the mixture, 2.20 g (12.4 mM) of the above prepared compound (M3) was added under stirring at room temperature, followed by washing with 8 ml of THF. Thereafter, the resultant mixture was stirred for 5 hours and 25 minutes at an inner temperature of 50.5°–53° C. on an oil bath. After the reaction, the reaction mixture was filtered to remove a precipitated crystal. The filtrate was concentrated under reduced pressure to obtain a residue. The residue was purified by silica gel column chromatography (eluent:toluene/ethyl acetate=100/1) to obtain 1.58 g of 5-cyano-2-methylcoumaran (M4) (Yield: 79.9%).

Step iii)

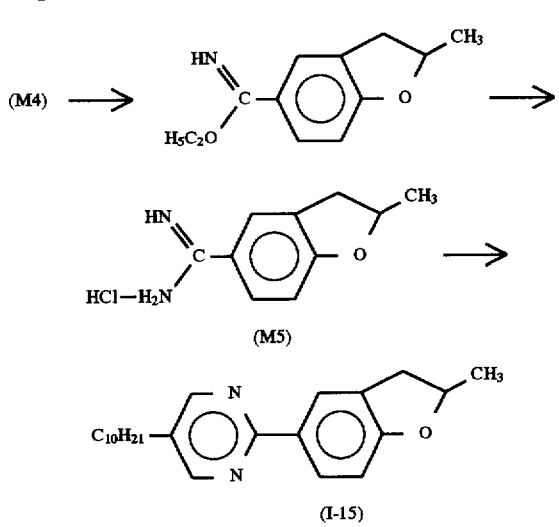

1.50 g (9.42 mM) of 5-cyano-2-methylcoumaran (M4), 1.53 g (33.2 mM) of ethanol and 17 ml of chloroform were placed in a 50 ml-three-necked flask and dissolved. On an ice-common salt bath, a hydrogen chloride gas was blown in the solution for 45 minutes at −4° to 1.5° C. under stirring to saturate the solution and the interior of the flask. The flask containing the mixture was left standing in a refrigerator for 2 days. The resultant mixture was poured into 120 ml of 5N—NaOH aqueous solution which had been iced, followed by extraction with chloroform. The organic layer was washed with water and dried with mirabilite, followed by distilling-off of the solvent to obtain an ethyl imidate. To the ethyl imidate, 0.53 g (9.91 mM) of ammonium chloride and 10 ml of 75% ethanol were added, followed by refluxing for 2 hours under stirring. After the reaction, an appropriate amount of acetone was added to the reaction mixture and was cooled on an ice bath. The precipitated crystal was removed from the reaction mixture by filtration and the filtrate was concentrated under reduced pressure to obtain a residue. To the residue, an appropriate amount of ethyl acetate was and left standing in a freezer to separate an oily matter. The ethyl acetate was removed by decantation, and the oily matter was dried under reduced pressure to obtain 0.81 g of 5-amino-2-methyl coumaran hydrochloride (M5) (Yield: 40.4%).

0.33 g (1.55 mM) of 5-amino-2-methylcoumaran hydrochloride (M5), 0.20 g (3.70 mM) of sodium methylate, 0.39 g (1.63 mM) of α-decyl-β-dimethylaminoacrolein and 5.5 ml of methanol were placed in a 30 ml-round bottomed flask, followed by refluxing for 8 hours and 50 minutes under stirring. After the reaction, the reaction mixture was cooled in a freezer to precipitate a crystal. The crystal was recovered by filtration and washed with water. The resultant crystal was dissolved in toluene and dried with mirabilite, followed by concentration under reduced pressure to obtain a residue. The residue was purified by silica gel column chromatography (eluent:toluene/ethyl acetate=100/1), followed by recrystallization from methanol to obtain 0.06 g of 5-(5-decylpyrimidine-2-yl)-2-octylcoumaran (Ex. Comp. No. I-15) (Yield: 11.0%).

Phase transition temperature (°C.)

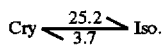

Herein, the respective symbols denote the following phase; Iso: isotropic phase; Ch: cholesteric phase: N: nematin phase; SmA: smectic A phase; SmC: smectic C phase; SmC*: chiral smectic C phase: Sm3. Sm4: smectic phase other than SmA and SmC; and Cry: crystal.

EXAMPLE 2

Production of 2-(2-methylcoumaran-5-yl)-5-(4-octylphenyl)pyrimidine (Ex. Comp. No. I-235)

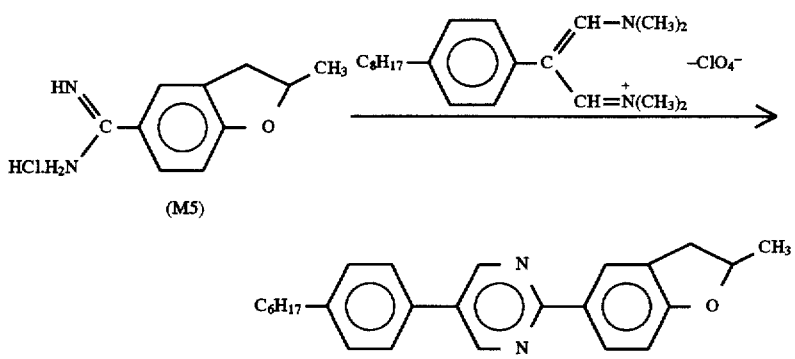

0.40 g (1.88 mM) of 5-amidino-2-methylcoumaran hydrochloride (M5) as an intermediate product prepared in Example 1, 0.79 g (1.90 mM) of 3-dimethylamino-2-(4-octylphenyl)-N,N-dimethylpropene-(2)-ammonium perchlorate 0.41 g (7.59 mM) of sodium methylate and 15 ml of methanol were placed in a 50 ml-round bottomed flask and refluxed for 5 hours and 10 minutes under stirring. After the reaction, the reaction mixture was cooled on an ice-common salt bath to precipitate a crystal. The crystal was recovered by filtration, followed by washing with water. The resultant crystal was dissolved in toluene and dried with mirabilite. After distilling-off of the solvent under reduced pressure, the residue was purified by silica gel column chromatography (eluent:toluene/ethyl acetate=100/1) and recrystallized from a mixture solvent of toluene and methanol to obtain 0.44 of 2 (-2methylcoumaran-5-yl)-5-(4-octylphenyl)pyrimidine (Ex. Comp. No. I-235) (Yield: 58.4%). The product showed the following phase transition temperatures (°C.).

EXAMPLE 3

Production of 5-(5-decylpyrimidine-2-yl)-2-octylcoumaran (Ex. Comp. No. I-17)

Step i)

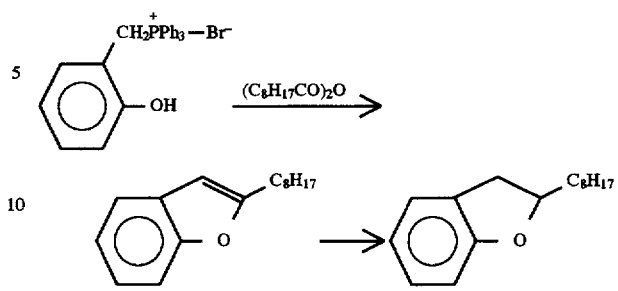

112 g (249 mM) of (2-hydroxybenzyl) triphenylphosphonium bromide, 83 g (278 mM) of nonanoic anhydride, 104 g (1.03 mM) of triethylamine and 800 ml of toluene were placed in a 3 1-three-necked flask, followed by refluxing for 4.5 hours under stirring. After the reaction, the reaction mixture was left standing at room temperature to precipitate a crystal. The crystal was removed by filtration. The filtrate was concentrated and purified by silica gel column chromatography (eluent:toluene/hexane=1/1) to obtain 44 g of liquid 2-octylbenzofuran (Yield: 76.6%).

Then, 44 g of 2-octylbenzofuran was dissolved in 440 ml of ethanol. To the solution 35 g of 10%-palladium-carbon was added to effect catalytic reduction for 3 hours sunder normal pressure. After the reaction, the catalyst was removed by filtration and the filtrate was concentrated under reduced pressure to obtain a residue. The residue was purified by silica gel column chromatography (eluent:hexane) to obtain 42 g of liquid 2-octylcoumaran (Yield: 94.6%).

Step ii)

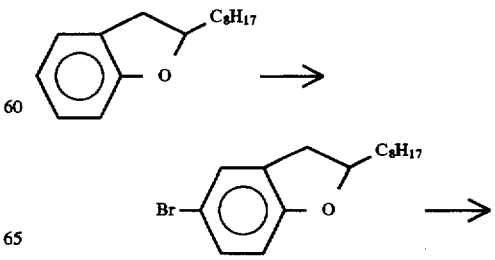

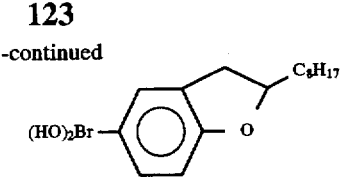

In a 50 ml-three-necked flask, 2.00 g (8.61 mM) of 2-octylcoumaran and 3.2 ml of dichloremethane were placed and mixed to obtain a solution. To the solution, 0.73 (8.69 mM) of NaHCO₃ and 3.2 ml of water were added. To the mixture, a solution of 0.44 ml (0.54 mM) of bromine in 1 ml of dichloromethane were added dropwise in 17 minutes under stirring on an ice bath, followed by stirring for 3 hours and 25 minutes at room temperature. After the reaction, the reaction mixture was poured into ice water and subjected to extraction with dichloromethane, followed by two times washing with a common salt aqueous solution and drying with mirabilite. The resultant mixture was concentrated under reduced pressure to obtain 2.58 g of 5-bromo-2-octylcoumaran (Yield: 96.3%).

Then, 2.00 g (6.43 mM) of b-bromo-2-octylcoumaran and 28 ml of dry THF were placed in a 100 ml-three-necked flask. To the mixture, 4.5 ml (7.20 mM) of a 1.6M solution of butyllithium in hexane was added dropwise under stirring and nitrogen atmosphere on a dry ice-acetone bath at an inner temperature of −70° to −68° C., followed by stirring for 50 minutes at the same temperature. To the resultant mixture a solution of 3.2 ml (13.9 mM) of triisopropylborate in 5.7 ml of dry THF was added dropwise in 10 minutes at an inner temperature of −73° to −68° C., followed by stirring for minutes at the same temperature. Thereafter, the cooling bath was removed and the inner temperature was increased to room temperature, followed by gradual addition of 9.5 ml of 10%-hydrochloric acid. After the reaction, the reaction mixture was poured into water and subjected to extraction with isopropyl ether, followed by washing with water, drying with mirabilite and distilling-off of the solvent to obtain a residue. To the residue, hexane was added and the mixture was left standing in a freezer to precipitate a crystal. The crystal was recovered by filtration to obtain 1.19 g of 2-octylcoumaran-5-boronic acid (Yield: 67.1%).

Step iii)

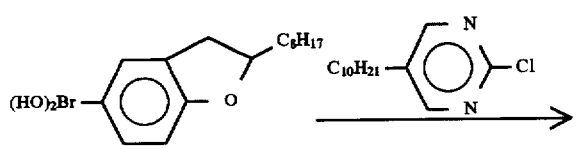

Under nitrogen atmosphere, 0.30 g (1.09 mM) of 2-octylcoumaran-5-boronic acid, 0.26 g (1.02 mM) of 2-chloro-5-decylpyrimidine and 1.5 ml of benzene were placed in a 20 ml-round-bottomed flask. Under stirring, 0.06 g of tetrakis(triphenylphosphine) palladium (0) and 1.5 ml of a 2M-sodium carbonate aqueous solution were added to the mixture, followed by refluxing for 5.5 hours. After the reaction, the reaction mixture was poured into water and subjected to extraction with ethyl acetate. The organic layer was washed with water, dried with mirabilite and concentrated under reduced pressure to obtain a residue. The residue was purified by silica gel column chromatography and recrystallized from a mixture solvent of toluene and methanol to obtain 0.11 g of 5-(5-decylpyrimidine-2-yl)-2-octylcoumaran (Ex. Comp. No-I-17) (Yield: 22.5%). The product showed the following phase transition temperatures (°C.).

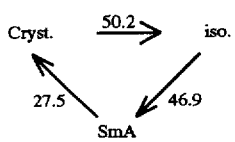

EXAMPLE 4

Production of 5-[4-(5-decylpyrimidine-2-yl)phenyl]-2-octylcoumaran (Ex. Comp. No. I-154)

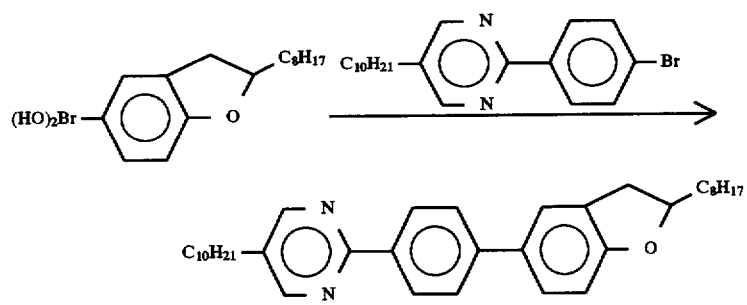

Under nitrogen atmosphere, 0.25 g (0.91 mM) of 2-octylcoumaran-5-boronic acid, 0.7 ml of ethanol, 0.30 g (0.80 mM) of 2-(3-bromophenyl)-5-decylpyrimidine and 1.3 ml of benzene were placed in a 20 ml-round-bottomed flask. Under stirring, 0.05 g of tetrakis(triphenylphosphine) palladium (0) and 1.3 ml of a 2M-sodium carbonate aqueous solution were added successively to the mixture, followed by refluxing for 1 hour and 40 minutes. After the reaction, the reaction mixture was left standing at room temperature to precipitate a crystal. The crystal was washed with water and dissolved in toluene. The solution was dried with mirabilite and the solvent was distilled off under reduced pressure to obtain a residue. The residue was purified by silica gel column chromatography and recrystallized from a mixture solvent of toluene and methanol and further recrystallized from acetone to obtain 0.28 g of 5-[4-(5-decylpyrimidine-2-yl)phenyl]-2-octylcoumaran (Ex. Comp. No. I-154) (Yield: 66.5%). The product showed the following phase transition temperatures (°C.).

EXAMPLE 5

Production of 5-[4-(5-dodecylpyrimidine-2-yl)phenyl]-2-octylcoumaran (Ex. Comp. No. I-156)

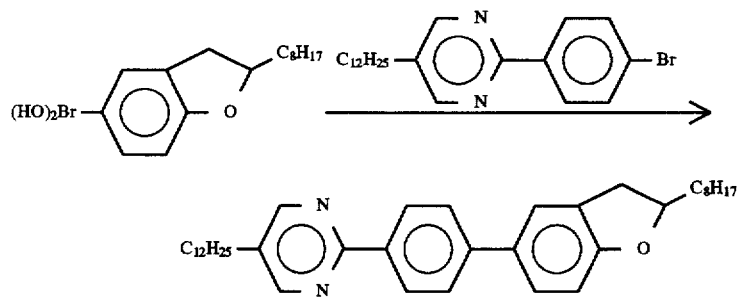

5-[4-(5-dodecylpyrimidine-2-yl)phenyl]-2-octylcoumaran (Ex. Comp. No. I-156) was prepared in the same manner as in Example 4 except that 2-(3-bromophenyl)-5-dodecylpyrimidine was used instead of 2-(3-bromophenyl)-5-decylpyrimidine (Yield: 72.7%). The product was showed the following phase transition temperatures (°C.).

EXAMPLE 6

Production of 5-[4-(5-ocrylpyrimidine-2-yl)phenyl]-2-octylcoumaran (Ex. Comp. No. I-152)

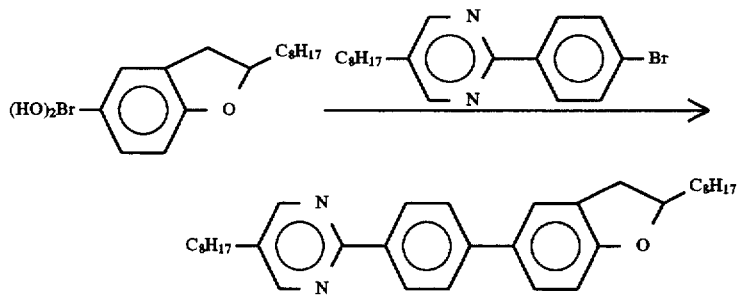

5-[4-(5-ocrylpyrimidine-2-yl)phenyl]-2-octylcoumaran (Ex. Comp. No. I-156) was prepared in the same manner as in Example 4 except that 2-(3 bromophenyl)-5-octylpyrimidine was used instead of 2-(3-bromophenyl)-5-decylpyrimidine (Yield: 52.2%). The product was showed the following phase transition temperatures (°C.).

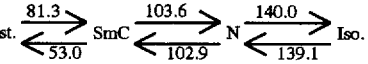

EXAMPLE 7

Production of 5-[4-(5-decylpyrimidine-2-yl)phenyl]-2-methylcoumaran (Ex. Comp. No. I-88)

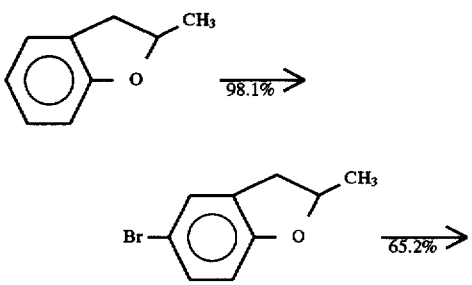

-continued

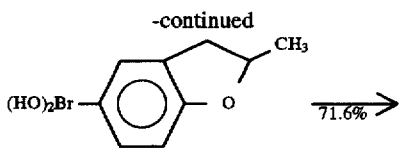

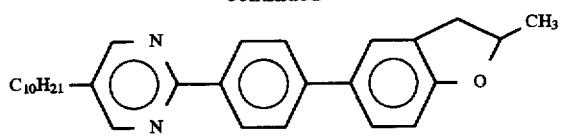

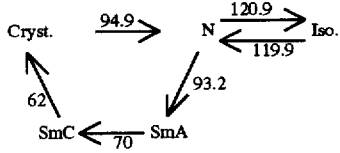

5-[4-(5-decylpyrimidine-2-yl)phenyl]-2-methylcoumaran (Ex. Comp. No. I-88) was prepared with the above indicated yields (%) in the same manner as in Example 3 except that 2-(3-bromophenyl)-5-decylpyrimidine was used instead of 2-chloro-5-decylpyrimidine. The product was showed the following phase transition temperatures (°C.).

EXAMPLE 8

A liquid crystal composition A was prepared by mixing the following compounds including the compound (Ex. Comp. No. I-154) prepared in Example 4 in the respectively indicated proportions.

| Structural formula | wt. parts |
|---|---|
| $C_6H_{13}$–pyrimidine–phenyl–$OC_{12}H_{25}$ | 2.3 |
| $C_8H_{17}$–pyrimidine–phenyl–$OC_9H_{19}$ | 4.7 |
| $C_8H_{17}$–pyrimidine–phenyl–$OC_{10}H_{21}$ | 4.7 |
| $C_9H_{19}$–pyrimidine–phenyl–$OC_8H_{17}$ | 2.3 |
| $C_{10}H_{21}O$–phenyl–COO–phenyl–$OCH_2CH(CH_3)C_2H_5$ | 26.0 |
| $C_6H_{13}$–benzothiazole–phenyl–$OC_8H_{17}$ | 20.0 |
| $C_5H_{11}$–phenyl–thiadiazole–phenyl–$C_5H_{11}$ | 5.0 |
| $C_6H_{13}$–phenyl–thiadiazole–phenyl–$C_4H_9$ | 5.0 |
| $C_{11}H_{23}$–pyrimidine–phenyl–OCO–thiophene–$C_4H_9$ | 6.7 |

| Structural formula | wt. parts |
|---|---|
| (structure with $C_{11}H_{23}$, pyrimidine, F-phenyl, ester, thiophene, $C_4H_9$) | 3.3 |
| (structure with $C_{10}H_{21}$, pyrimidine, phenyl, $OCH_2CHC_6H_{13}$ with F) | 10.0 |
| I-151 (structure with $C_{10}H_{21}$, pyrimidine, biphenyl, tetrahydrofuran-$C_8H_{17}$) | 10.0 |

The liquid crystal composition A showed the following phase transition series.
Phase transition temperature (°C.)

$$\text{Cry.} \xrightarrow{-13.7} \text{SmC}^* \xrightarrow{56} \text{SmA} \xrightarrow{75.3} \text{Ch.} \xrightarrow{83.3} \text{Iso.}$$

EXAMPLE 9

Two 0.7 mm-thick glass plates were provided and respectively coated with an ITO film to form an electrode for voltage application, which was further coated with an insulating layer of vapor-deposited $SiO_2$. On the insulating layer, a 0.2%-solution of silane coupling agent (KBM-602, available from Shinetsu Kagaku K. K.) in isopropyl alcohol was applied by spinner coating at a speed of 2000 rpm for 15 second and subjected to hot curing treatment at 120° C. for 20 min.

Further, each glass plate provided with an ITO film and treated in the above described manner was coated with a 1.5%-solution of polyimide resin precursor (SP-510, available from Toray K. K.) in dimethylacetoamide by a spinner coater rotating at 2000 rpm for 15 seconds. Thereafter, the coating film was subjected to heat curing at 300° C. for 60 min. to obtain about 250 Å-thick film. The coating film was rubbed with acetate fiber-planted cloth. The thus treated two glass plates were washed with isopropyl alcohol. After silica beads with an average particle size of 2.0 microns were dispersed on one of the glass plates, the two glass plates were applied to each other with a bonding sealing agent (Lixon Bond, available from Chisso K. K.) so that their rubbed directions were parallel to each other and heated at 100° C. for 60 min. to form a blank cell. The cell gap was found to be about 2 microns as measured by a Berek compensator.

Then, the liquid crystal composition A prepared in Example 8 was heated into an isotropic liquid, and injected into the above prepared cell under vacuum and, after sealing, was gradually to 25° C. at a rate of 20° C./hour to prepare a ferroelectric liquid crystal device.

The ferroelectric liquid crystal device was subjected to measurement of the magnitude of spontaneous polarization Ps and an optical response time (time from voltage application until the transmittance change reaches 90% of the maximum under the application of a peak-to-peak voltage Vpp of 20 V in combination with right-angle cross-nicol polarizers).

The results are shown below.

|  | 10° C. | 20° C. | 40° C. |
|---|---|---|---|
| Response time (μsec) | 334 | 167 | 69 |
| Ps (nC/cm$^2$) | 10.6 | 9.2 | 5.4 |

EXAMPLE 10

A liquid crystal composition B was prepared by mixing the following compounds including the compound (Ex. Comp. No. I-152) prepared in Example 6 in the respectively indicated proportions.

| Structural formula | wt. parts |
|---|---|
| (structure with $C_6H_{13}$, pyrimidine, phenyl, $OC_{12}H_{25}$) | 4.0 |
| (structure with $C_8H_{17}$, pyrimidine, phenyl, $OC_9H_{19}$) | 8.0 |

-continued

| Structural formula | wt. parts |
|---|---|
| $C_8H_{17}$—[pyrazine]—[phenyl]—$OC_{10}H_{21}$ | 8.0 |
| $C_9H_{19}$—[pyrazine]—[phenyl]—$OC_8H_{17}$ | 4.0 |
| $C_{10}H_{21}O$—[phenyl]—CO-O—[phenyl]—$OCH_2CH(CH_3)C_2H_5$ | 26.0 |
| $C_6H_{13}$—[benzothiazole]—[phenyl]—$OC_8H_{17}$ | 20.0 |
| $C_5H_{11}$—[phenyl]—CH=N-N=CH—S—[phenyl]—$C_5H_{11}$ | 2.5 |
| $C_6H_{13}$—[phenyl]—CH=N-N=CH—S—[phenyl]—$C_4H_9$ | 2.5 |
| $C_{11}H_{23}$—[pyrazine]—[phenyl]—OC(O)—[thiophene]—$C_4H_9$ | 3.3 |
| $C_{11}H_{23}$—[pyrazine]—[fluorophenyl]—OC(O)—[thiophene]—$C_4H_9$ | 1.7 |
| $C_{10}H_{21}$—[pyrazine]—[phenyl]—$OCH_2CH(F)C_6H_{13}$* | 10.0 |
| I-152  $C_8H_{17}$—[pyrazine]—[phenyl]—[dihydrobenzofuran]—$C_8H_{17}$ | 10.0 |

The liquid crystal composition B showed the following phase transition series.

Phase transition temperature (°C.)

$$\text{Cry.} \xrightarrow{-15.6} \text{SmC*} \xrightarrow{57} \text{SmA} \xrightarrow{73.7} \text{Ch.} \xrightarrow{78.5} \text{Iso.}$$

A ferroelectric liquid crystal device was prepared in the same manner as in Example 9 except for injecting the composition B into blank cell. The ferroelectric liquid crystal device was subjected to measurement of Ps and response time in the same manner as in Example 9, whereby the following results were obtained.

|  | 10° C. | 20° C. | 40° C. |
|---|---|---|---|
| Response time (μsec) | 322 | 173 | 72 |
| Ps (nC/cm$^2$) | 10.8 | 9.1 | 5.7 |

EXAMPLE 11

A liquid crystal composition C was prepared by mixing the following compounds in the respectively indicated proportions.

| Structural formula | wt. parts |
|---|---|
| C$_7$H$_{15}$—[pyrimidine]—[phenyl]—OC$_9$H$_{19}$ | 12 |
| C$_{11}$H$_{23}$—[pyrimidine]—[phenyl]—OC$_6$H$_{13}$ | 10 |
| C$_8$H$_{17}$—[pyrimidine]—[phenyl]—O—(CH$_2$)$_3$—*CHCH$_3$—C$_2$H$_5$ | 10 |
| C$_{10}$H$_{21}$—[pyrimidine]—[phenyl]—O—(CH$_2$)$_4$—*CHCH$_3$—OCH$_3$ | 3 |
| C$_8$H$_{17}$—[pyrimidine]—[phenyl]—[phenyl]—C$_6$H$_{13}$ | 8 |
| C$_6$H$_{13}$O—[phenyl]—OC(O)—[naphthyl]—OC$_8$H$_{17}$ | 4 |
| C$_3$H$_7$—[H]—C(O)O—[phenyl]—[pyrimidine]—C$_{11}$H$_{23}$ | 6 |
| C$_8$H$_{17}$—[H]—C(O)O—[phenyl]—[pyrimidine]—C$_{11}$H$_{23}$ | 2 |
| C$_5$H$_{11}$—[H]—C(O)O—[phenyl]—[pyridine]—C$_{11}$H$_{23}$ | 8 |
| C$_{10}$H$_{21}$O—[phenyl]—C(O)O—[phenyl]—OCH$_2$*CHCH$_3$—C$_2$H$_5$ | 15 |
| C$_4$H$_9$—[H]—CH$_2$O—[phenyl]—[pyridine]—C$_6$H$_{13}$ | 7 |
| C$_6$H$_{11}$—[H]—CH$_2$O—[phenyl]—[pyridine]—C$_6$H$_{13}$ | 7 |
| C$_9$H$_{19}$O—[phenyl]—OCH$_2$—[phenyl]—[phenyl]—C$_6$H$_{13}$ | 4 |

| Structural formula | wt. parts |
|---|---|
| 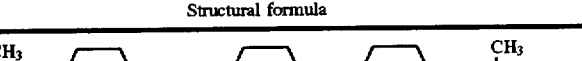 | 2 |
| 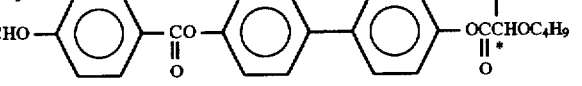 | 2 |

The liquid crystal composition C was further mixed with the following compounds in the proportions indicated below to provide a liquid crystal composition D.

| Ex. Comp. No. | Structural Formula | wt. parts |
|---|---|---|
| I-18 | | 4 |
| I-55 | | 3 |
| I-310 | | 2 |
| Composition C | | 91 |

A ferroelectric liquid crystal device was prepared in the same manner as in Example 9 except for injecting the composition D into blank cell. The ferroelectric liquid crystal device was subjected to measurement of response time in the same manner as in Example 9, whereby the following results were obtained.

|  | 10° C. | 25° C. | 40° C. |
|---|---|---|---|
| Response time (μsec) | 609 | 305 | 172 |

Comparative Example 1

A ferroelectric liquid crystal device was prepared and subjected to measurement of response time in the same manner as in Example 11 except for injecting the composition C alone into the blank cell, whereby the following results were obtained.

|  | 10° C. | 25° C. | 40° C. |
|---|---|---|---|
| Response time (μsec) | 784 | 373 | 197 |

EXAMPLE 12

A liquid crystal composition E was prepared by mixing the following Example Compounds instead of those of (I-8), (I-55) and (I-310) used in Example 11 in the indicated proportions with the liquid crystal composition C.

| Ex. Comp. No. | Structural formula | wt. parts |
|---|---|---|
| I-8 | 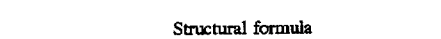 | 3 |

| Ex. Comp. No. | Structural formula | wt. parts |
|---|---|---|
| I-137 | 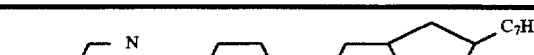 | 2 |
| I-366 |  | 2 |
| | Composition C | 93 |

A ferroelectric liquid crystal device was prepared in the same manner as in Example 9 except that the above liquid crystal composition E was used, and the device was subjected to measurement of optical response time. The results of the measurement are shown below.

| | 10° C. | 25° C. | 40° C. |
|---|---|---|---|
| Response time (μsec) | 551 | 269 | 150 |

EXAMPLE 13

A liquid crystal composition F was prepared by mixing the following Example Compounds instead of those of (I-8), (I-137) and (I-366) used in Example 12 in the indicated proportions with the liquid crystal composition C.

| Ex. Comp. No. | Structural formula | wt. parts |
|---|---|---|
| I-49 | | 3 |
| I-75 | | 2 |
| I-201 | | 3 |
| | Composition C | 92 |

A ferroelectric liquid crystal device was prepared in the same manner as in Example 9 except that the above liquid crystal composition F was used, and the device was subjected to measurement of optical response time. The results of the measurement are shown below.

| | 10° C. | 25° C. | 40° C. |
|---|---|---|---|
| Response time (μsec) | 632 | 313 | 176 |

EXAMPLE 14

A liquid crystal composition G was prepared by mixing the following compounds in the indicated proportions.

| Structural formula | wt. parts |
|---|---|
| 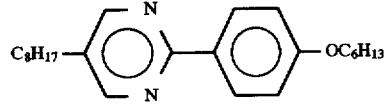 | 10 |
| 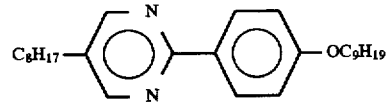 | 5 |
| 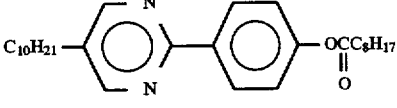 | 7 |
| 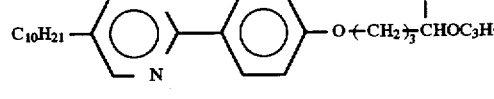 | 7 |
| 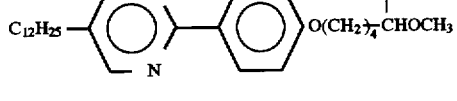 | 6 |
| 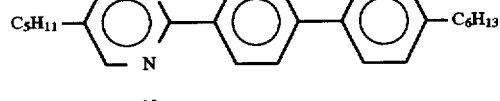 | 5 |
| 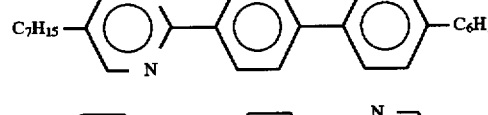 | 5 |
| 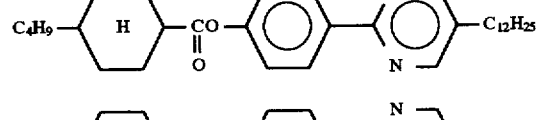 | 8 |
|  | 8 |
| 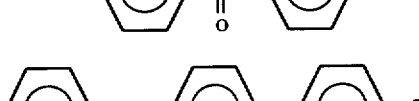 | 20 |
| 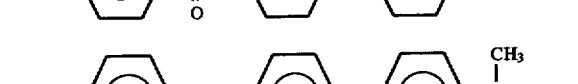 | 5 |
| 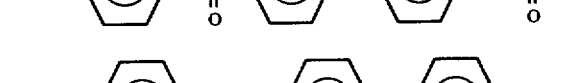 | 5 |
|  | 6 |

-continued

| Structural formula | wt. parts |
|---|---|
|  | 3 |

The liquid crystal composition G was further mixed with the following compounds in the proportions indicated below to provide a liquid crystal composition H.

| Ex. Comp. No. | Structural Formula | wt. parts |
|---|---|---|
| I-46 |  | 3 |
| I-62 | 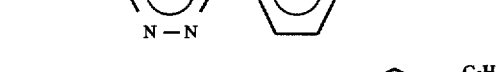 | 3 |
| I-117 | 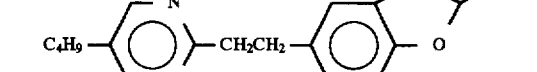 | 2 |
| | Composition G | 92 |

A ferroelectric liquid crystal device was prepared in the same manner as in Example 9 except that the above liquid crystal composition H was used, and the device was subjected to measurement of optical response time and observation of switching states. In the device, a monodomain with a good and uniform alignment characteristic was observed. The results of the measurement are shown below.

| | 10° C. | 25° C. | 40° C. |
|---|---|---|---|
| Response time (μsec) | 512 | 257 | 135 |

Further, when the device was driven, a clear switching action was observed, and good bistability was shown after the termination of the voltage application.

Comparative Example 2

A ferroelectric liquid crystal device was prepared and subjected to measurement of response time in the same manner as in Example 14 except for injecting the composition G alone into a blank cell, whereby the following results were obtained.

| | 10° C. | 25° C. | 40° C. |
|---|---|---|---|
| Response time (μsec) | 653 | 317 | 159 |

EXAMPLE 15

A liquid crystal composition J was prepared by mixing the following Example Compounds instead of those of (I-46), (I-62) and (I-117) used in Example 14 in the indicated proportions with the liquid crystal composition G.

| Ex. Comp. No. | Structural formula | wt. parts |
|---|---|---|
| I-208 |  | 2 |

-continued

| Ex. Comp. No. | Structural formula | wt. parts |
|---|---|---|
| I-264 | 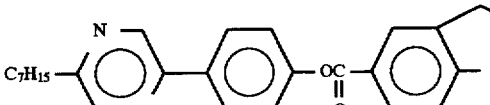 | 2 |
| I-358 | 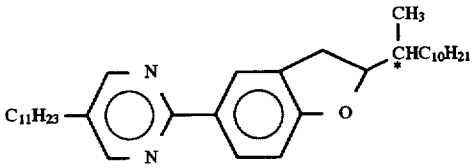 | 3 |
| Composition G | | 93 |

A ferroelectric liquid crystal device was prepared in the same manner as in Example 9 except that the above liquid crystal composition J was used, and the device was subjected to measurement of optical response time and observation of switching states. In the device, a monodomain with a good and uniform alignment characteristic was observed. The results of the measurement are shown below.

|  | 10° C. | 25° C. | 40° C. |
|---|---|---|---|
| Response time (μsec) | 456 | 232 | 128 |

EXAMPLE 16

A liquid crystal composition K was prepared by mixing the following Example Compounds instead of those of (I-208), (I-264) and (I-358) used in Example 15 in the indicated proportions with the liquid crystal composition G.

of the measurement are shown below.

|  | 10° C. | 25° C. | 40° C. |
|---|---|---|---|
| Response time (μsec) | 538 | 270 | 146 |

EXAMPLE 17

A liquid crystal composition L was prepared by mixing the following compounds in the indicated proportions.

| Ex. Comp. No. | Structural formula | wt. parts |
|---|---|---|
| I-1 | 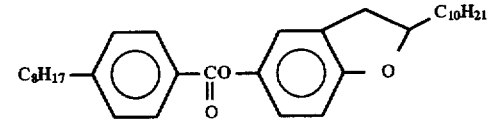 | 3 |
| I-78 | 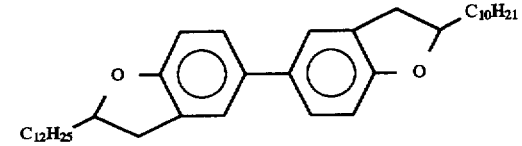 | 3 |
| I-318 | 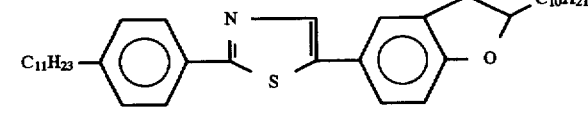 | 2 |
| Composition G | | 92 |

A ferroelectric liquid crystal device was prepared in the same manner as in Example 9 except for using the composition K was used, and the device was subjected to measurement of optical response time and observation of switching states. In the device, a monodomain with a good and uniform alignment characteristic was observed. The results

| Structural formula | wt. parts |
|---|---|
| 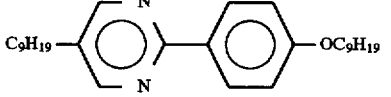 | 6 |
| 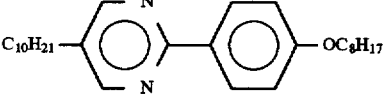 | 6 |
| 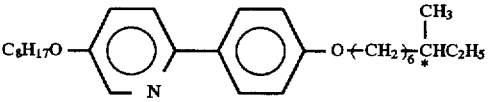 | 7 |
| 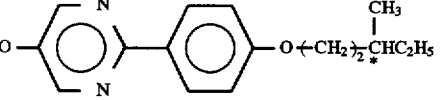 | 14 |
| 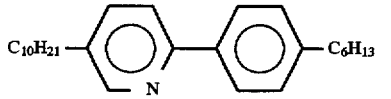 | 8 |
| 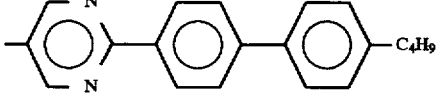 | 4 |
| 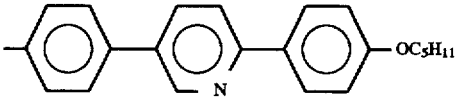 | 2 |
| 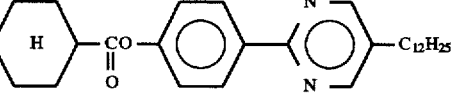 | 10 |
| 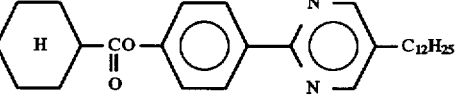 | 5 |
| 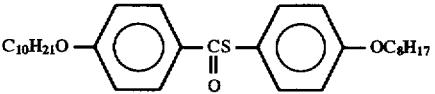 | 10 |
| 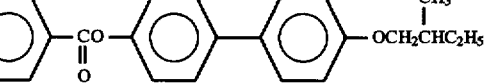 | 7 |
| 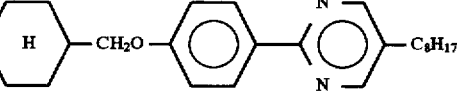 | 7 |
| 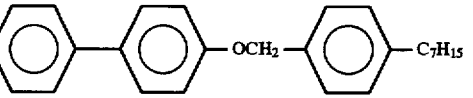 | 5 |

| Structural formula | wt. parts |
|---|---|
| 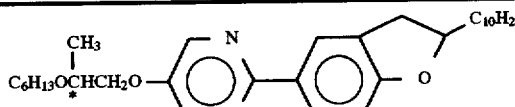 $C_{12}H_{25}$—[pyridazine]—[phenyl]—$OCH_2\overset{*}{C}H(F)C_5H_{11}$ | 2 |
| $C_5H_{11}$—[cyclohexyl H]—CO—O—[phenyl]—$OCH_2\overset{*}{C}H(F)C_6H_{13}$ | 2 |
| $C_{12}H_{25}O$—[phenyl]—[pyrimidine]—$CO\text{-}O\text{-}(CH_2)_3\overset{*}{C}H(CH_3)C_2H_5$ | 2 |
| $C_{12}H_{25}O$—[phenyl]—[pyrimidine]—$O\text{-}(CH_2)_3\overset{*}{C}H(CH_3)OC_3H_7$ | 3 |

The liquid crystal composition L was further mixed with the following compounds in the proportions indicated below to provide a liquid crystal composition M.

| Ex. Comp. No. | Structural formula | wt. parts |
|---|---|---|
| I-25 | 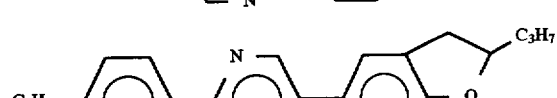 $C_6H_{13}O\overset{*}{C}H(CH_3)CH_2O$—[pyrimidine]—[phenyl]—[furan]—$C_{10}H_{21}$ | 4 |
| I-242 | $C_5H_{11}$—[pyrimidine]—[phenyl]—[furan]—$C_3H_7$ | 3 |
| I-261 | $C_6H_{13}$—[thiadiazole]—[phenyl]—$OC(=O)$—[phenyl]—[furan]—$C_7H_{15}$ | 2 |
| Composition L | | 91 |

A ferroelectric liquid crystal device was prepared in the same manner as in Example 9 except that the above liquid crystal composition M was used, and the device was subjected to measurement of optical response time and observation of switching states. In the device, a monodomain with a good and uniform alignment characteristic was observed. The results of the measurement are shown below.

|  | 10° C. | 25° C. | 40° C. |
|---|---|---|---|
| Response time (μsec) | 523 | 271 | 152 |

Comparative Example 3

A ferroelectric liquid crystal device was prepared and subjected to measurement of response time in the same manner as in Example 17 except for injecting the composition L alone into the cell, whereby the following results were obtained.

|  | 10° C. | 25° C. | 40° C. |
|---|---|---|---|
| Response time (μsec) | 668 | 340 | 182 |

EXAMPLE 18

A liquid crystal composition N was prepared by mixing the following Example Compounds instead of those of (I-25), (I-242) and (I-261) used in Example 17 in the indicated proportions with the liquid crystal composition L.

| Ex. Comp. No. | Structural formula | wt. parts |
|---|---|---|
| I-51 | ![structure with C11H22, benzoxazole, C8H17, coumaran] | 2 |
| I-288 | ![structure with C6H13, cyclohexane H, two phenyls, coumaran, C7H15] | 2 |
| I-344 | ![structure with C4H9, pyrimidine, phenyl, coumaran, phenyl, C8H17] | 3 |
| Composition L | | 93 |

A ferroelectric liquid crystal device was prepared in the same manner as in Example 9 except that the above liquid crystal composition N was used, and the device was subjected to measurement of optical response time and observation of switching states, in the device, a monodomain with a good and uniform alignment characteristic was observed. The results of the measurement are shown below.

| | 10° C. | 25° C. | 40° C. |
|---|---|---|---|
| Response time (μsec) | 581 | 302 | 167 |

As apparent from the above Examples 11 to 18, the ferroelectric liquid crystal device including the liquid crystal compositions D, E, F, H, J, K, M and N, i.e., compositions containing a mesomorphic compound having a coumaran skeleton, according to the present invention provided improved operation characteristic at a lower temperature, high speed responsiveness and a decreased temperature dependence of response speed.

EXAMPLE 19

A blank cell was prepared in the same manner as in Example 9 by using a 2% aqueous solution of polyvinyl alcohol resin (PVA-117, available from Kuraray K. K.) instead of the 1.5%-solution of polyimide resin precursor in dimethylacetoamide on each electrode plate. A ferroelectric liquid crystal device was prepared by filling the blank cell with the liquid crystal composition E used in Example 12. The liquid crystal device was subjected to measurement response time in the same manner as in Example 9. The results are shown below.

| | 10° C. | 25° C. | 40° C. |
|---|---|---|---|
| Response time (μsec) | 542 | 269 | 152 |

EXAMPLE 20

A blank cell was prepared in the same manner as in Example 9 except for omitting the SiO₂ layer to form an alignment control layer composed of the polyimide resin layer alone on each electrode plate. A ferroelectric liquid crystal devices were prepared by filling such a blank cell with liquid crystal composition E used in Example 12. The liquid crystal device was subjected to measurement of response time in the same manner as in Example 9. The results are shown below.

| | 10° C. | 25° C. | 40° C. |
|---|---|---|---|
| Response time (μsec) | 528 | 260 | 147 |

As is apparent from the above Examples 19 and 20, also in the case of a different device structure, the device containing the ferroelectric liquid crystal composition E according to the present invention provided an improved low-temperature operation characteristic and a decreased temperature dependence of response speed similarly as in Example 12.

EXAMPLE 21

Production of 5-(4'-decylbiphenyl-4-yl)-2-octylcoumaran (Ex. Comp. No. I-372)

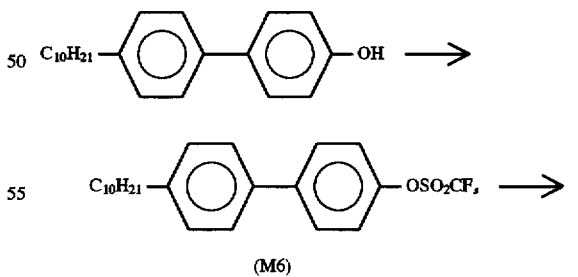

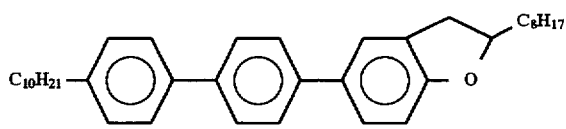

To a solution of 1.00 g (3.22 mM) of 4'-decyl-4-hydroxybiphenyl in 1.6 ml of pyridine, 0.60 ml (3.57 mM)

of trifluoromethanesulfonic acid anhydride was gradually added dropwise under stirring acid cooling on an ice-common salt bath, followed by stirring for 20 minutes at the same temperature and further stirring for 1 hour and 10 minutes at room temperature. After the reaction, the reaction mixture was poured into water and subjected to extraction with isopropyl ether. The organic layer was successively washed once with a common salt aqueous solution, once with 12%-hydrochloric acid aqueous solution and twice with a common salt aqueous solution, followed by drying with mirabilite and distilling-off of solvent to obtain 1.41 g of a crystalline trifluoromethanesulfonate (M6) (Yield: 98.9%).

Then, under nitrogen atmosphere, 0.35 g (0.79 mM) of the sulfonate (M6), 0.24 g (0.87 mM) of 2-octylcoumaran-5-boronic acid, 1.3 ml of toluene and 0.7 ml of ethanol were placed and mixed in a 20 ml-round-bottomed flask to obtain a solution. Under stirring, 0.04 g of tetrakis (triphenylphosphine) palladium (0) and 1.3 ml of a 2M-sodium carbonate aqueous solution were added successively to the solution, followed by refluxing for 4.5 hours. After the reaction, the reaction mixture was cooled to room temperature. To the mixture, toluene and water were added, followed by stirring at room temperature. The insoluble matter was removed by filtration. The organic layer was dried with mirabilite and the solvent was distilled off under reduced pressure to obtain a residue. The residue was purified by silica gel column chromatography and recrystallized from a mixture solvent of toluene and methanol to obtain 0.35 of 5-(4'-decylbiphenyl-4-yl)-2-octylcoumaran (Ex. Comp. No. I-372) (Yield: 84.3%). The product showed the following phase transition temperatures (°C.).

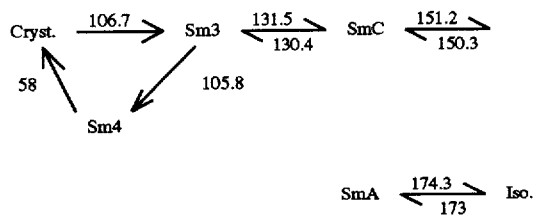

EXAMPLE 22

Production of 5-[3-fluoro-4-(5-decylpyrimidine-2-yl) phenyl]-2-octylcoumaran (Ex. Comp. No. I-207)

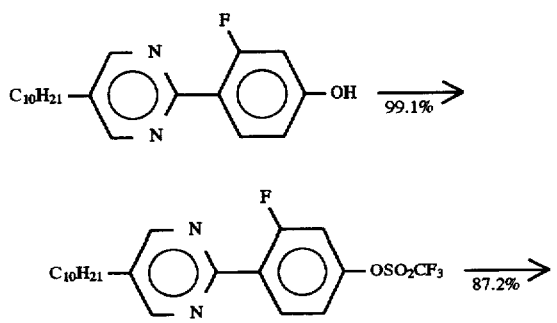

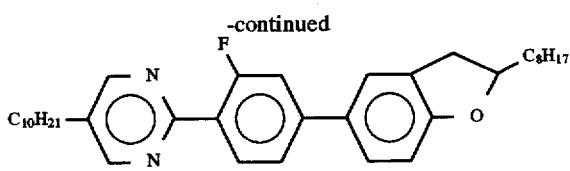

5-[3-fluoro-4-(5-decylpyrimidine-2-yl)phenyl]-2-octylcoumaran (Ex. Comp. No. I-207) was prepared with the above indicated yields in the same manner as in Example 21 except that 3-fluoro-4-(5-decylpyrimidine-2-yl)phenol was used instead of 4'-decyl-4-hydroxybiphenyl. The product showed the following phase transition temperatures (°C.).

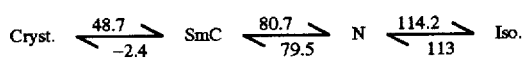

EXAMPLE 23

Production of 5-(5-undecylpyrimidine-2-yl)-2-decylcoumaran (Ex. Comp. No. I-375)

5-(5-undecylpyrimidine-2-yl)-2-decylcoumaran was prepared in the same manner as in Example 3 except that undecylic anhydride was used instead of nonanoic anhydride through the following reaction schemes accompanied by the respective yields (%).

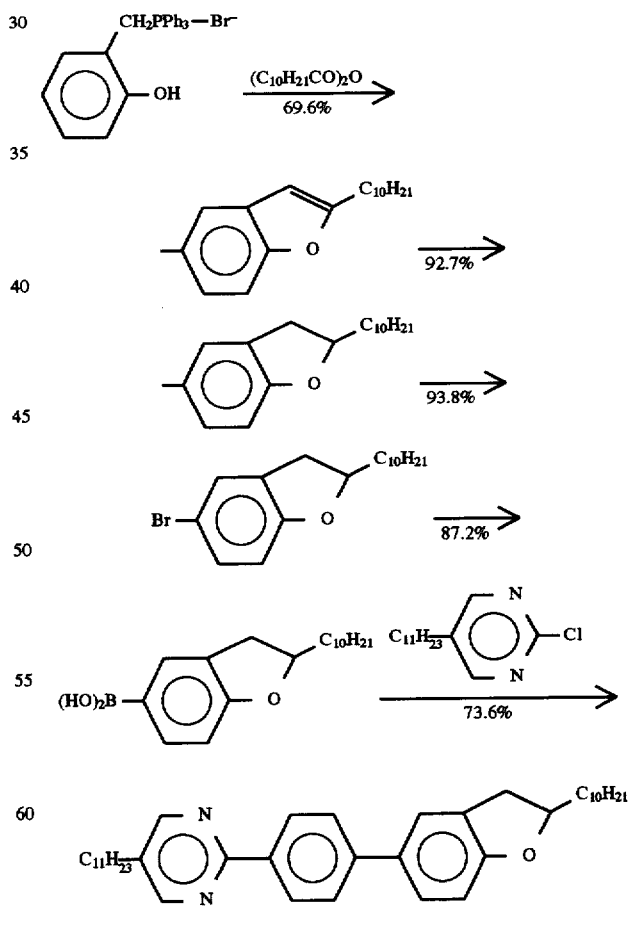

The product showed the following phase transition temperature (°C.).

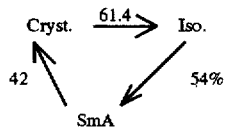

As described hereinabove, according to the present invention, there is provided a mesomorphic compound which can effectively be applied to a liquid crystal device utilizing ferroelectricity when the compound per se assumes a chiral smectic phase. Further, there is also provided a liquid crystal composition containing the compound and assuming a chiral smectic phase, whereby a liquid crystal device comprising the composition can be operated by utilizing ferroelectricity of the composition. The present invention provides a liquid crystal device using such a composition which shows a good switching characteristic, an improved low-temperature operation characteristic and a decreased temperature-dependence of response speed. The present invention further provides a display apparatus and a display method which employ such a device as a display unit, whereby good display characteristics can be obtained in combination with a light source, a drive circuit, etc.

What is claimed is:

1. A mesomorpic compound represented by the following formula (I):

$$R_1—A_1—X_1—A_2—X_2—A_3—R_2 \quad (I)$$

wherein $R_1$ and $R_2$ independently denote

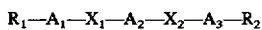

or a linear or branched alkyl group having 1-18 carbon atoms capable of including one or non-neighboring two or more —CH$_2$— groups which can be replaced with —O—, —S—,

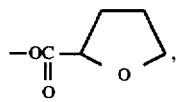

—CH=CH— or —C≡C—; said linear or branched alkyl group being capable of including hydrogen which can be replaced with fluorine;

$X_1$ and $X_2$ independently denote a single bond,

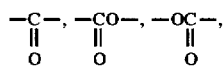

—CH$_2$O—, —OCH$_2$—, —CH$_2$CH$_2$— or —C≡C—;

$A_1$, $A_2$ and $A_3$ independently denote a single bond,

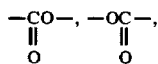

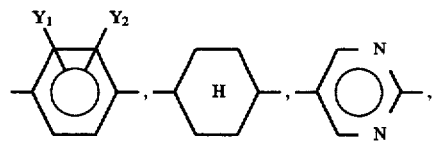

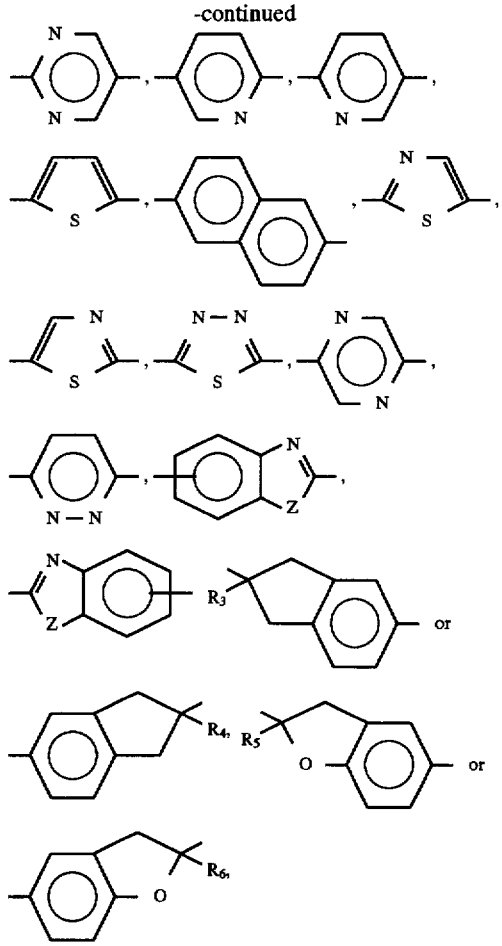

wherein $R_3$, $R_4$, $R_5$ and $R_6$ independently denote hydrogen, halogen or a linear or branched alkyl group having 1-18 carbon atoms; $Y_1$ and $Y_2$ independently denote H, F, Cl, Br, —CH$_3$, —CF$_3$ or —CN; Z denotes O or S; wherein at least one of $A_1$, $A_2$ and $A_3$ is

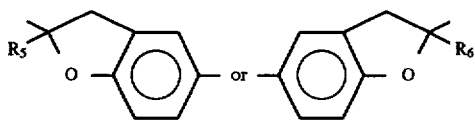

and the remaining groups of $A_1$, $A_2$ and $A_3$ cannot be a single bond simultaneously.

2. A mesomorphic compound according to claim 1, which is represented by any one of the following formula (Ia) to (It):

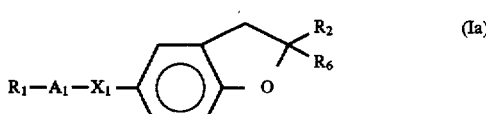

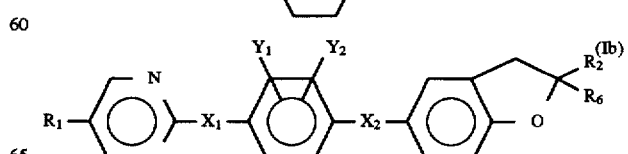

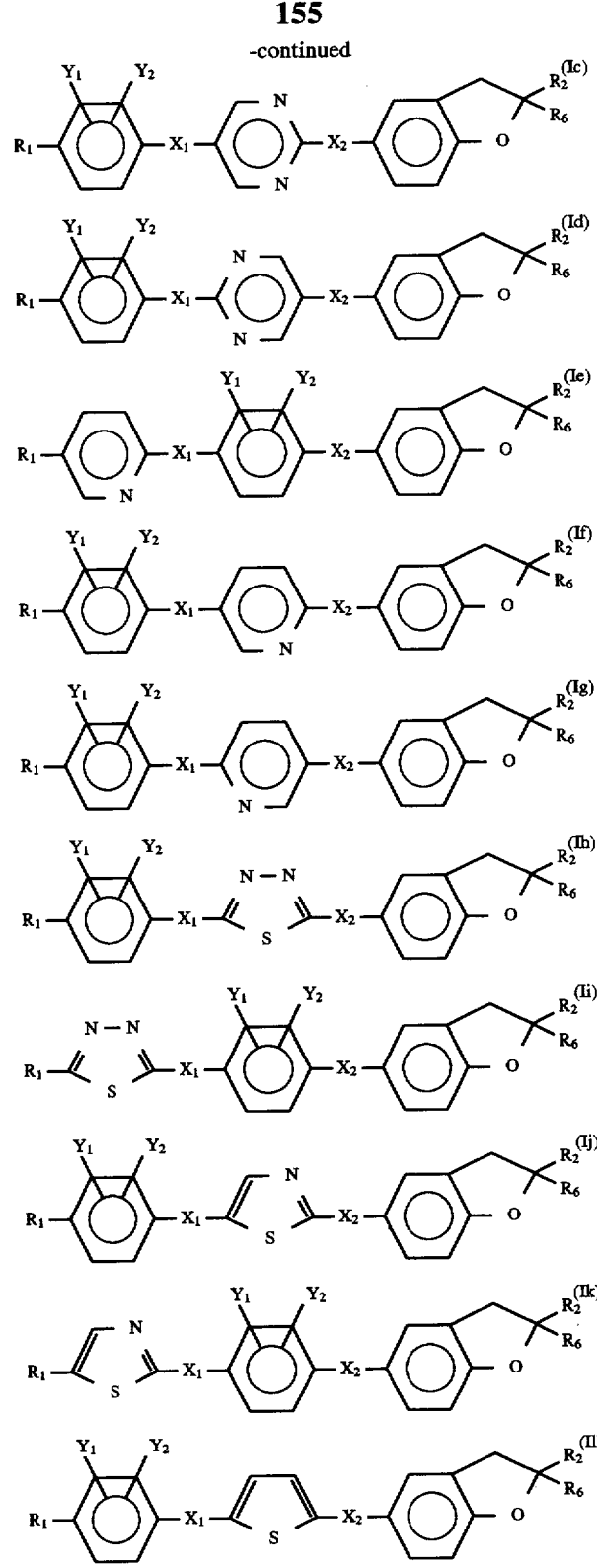
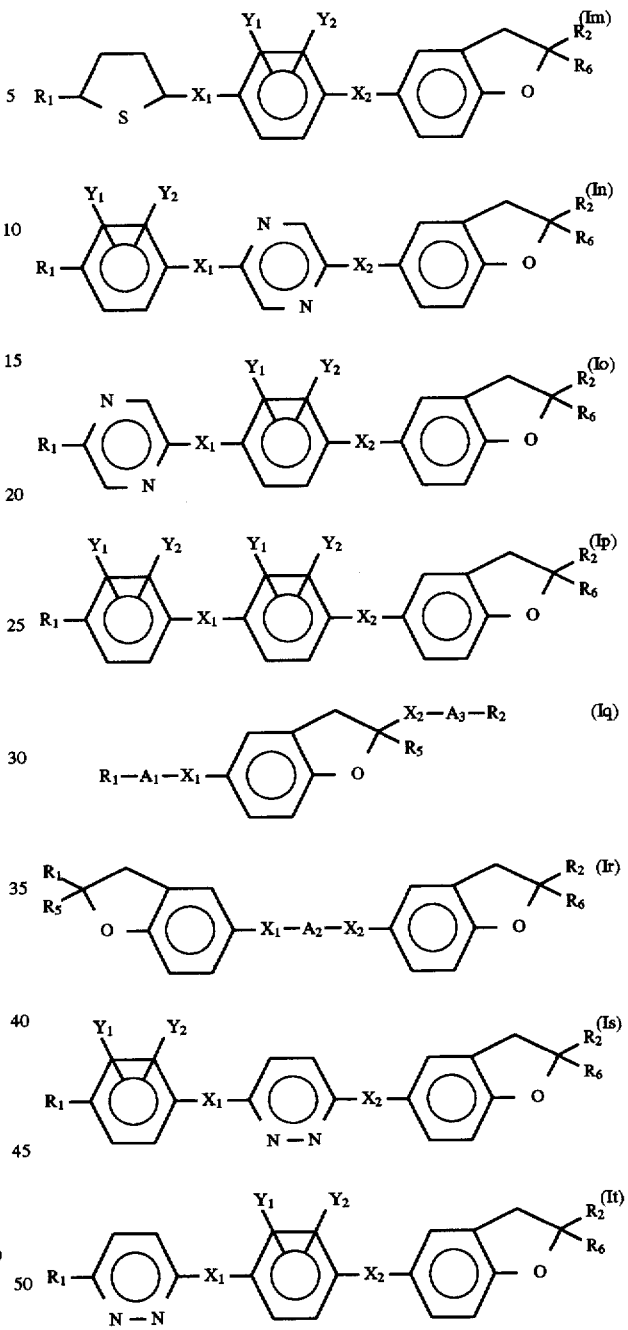
wherein $R_1$, $R_2$, $X_1$, $X_2$, $A_1$, $A_2$, $A_3$, $R_3$, $R_4$, $R_5$, $R_6$, $Y_1$, $Y_2$, and Z have the same meanings as defined in claim 1.
3. A mesomorphic compound according to claim 1, which is represented by any one of the following formulas (Iaa) to (Itd):

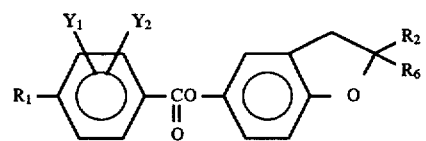 (Iaa)
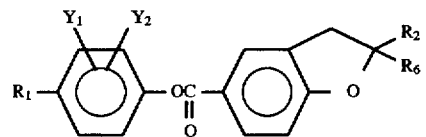 (Iab)
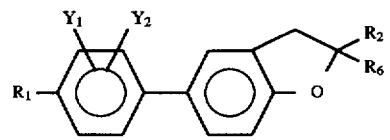 (Iac)
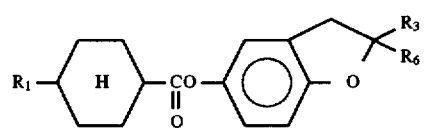 (Iad)
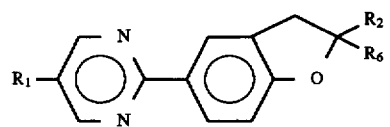 (Iae)
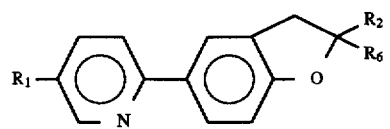 (Iaf)
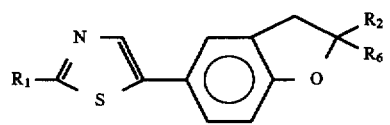 (Iag)
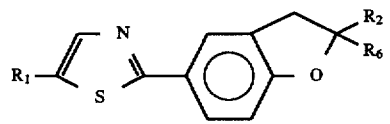 (Iah)
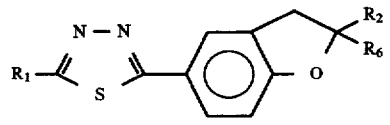 (Iai)
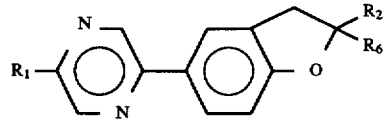 (Iaj)
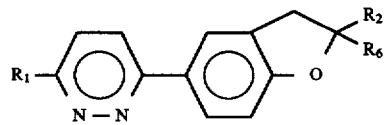 (Iak)
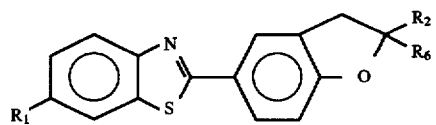 (Ial)

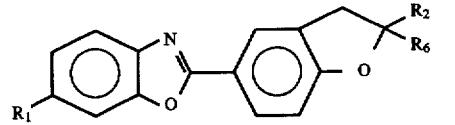 (Iam)
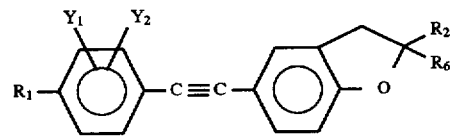 (Ian)
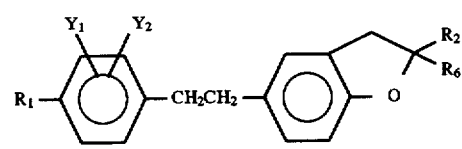 (Iao)
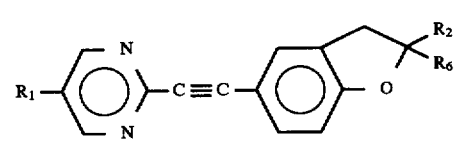 (Iap)
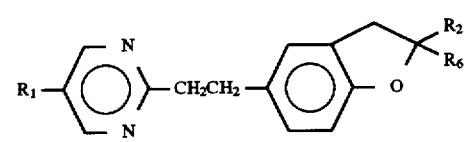 (Iaq)
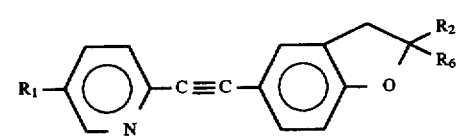 (Iar)
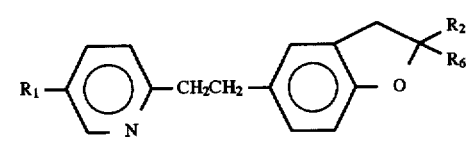 (Ias)
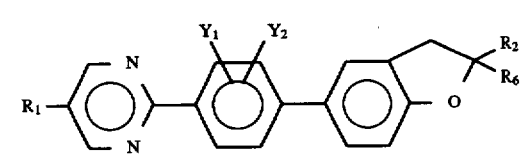 (Iba)
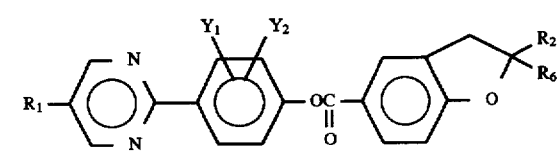 (Ibb)
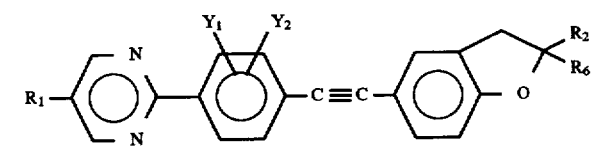 (Ibc)
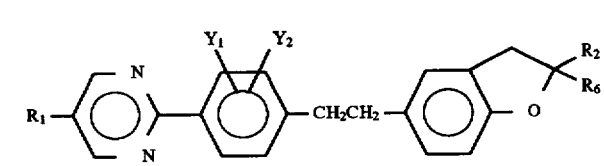 (Ibd)

-continued
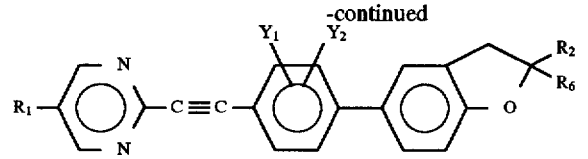 (Ibe)
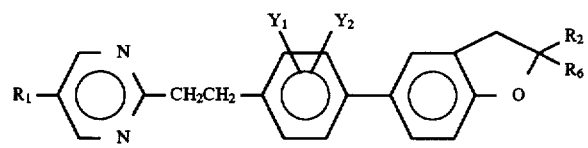 (Ibf)
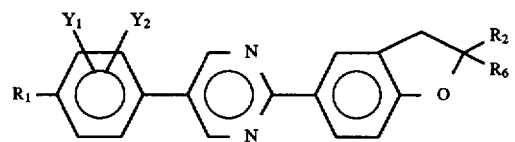 (Ica)
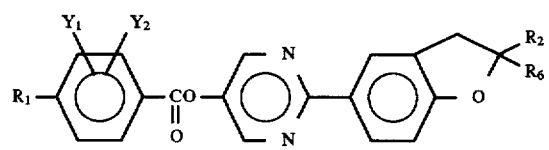 (Icb)
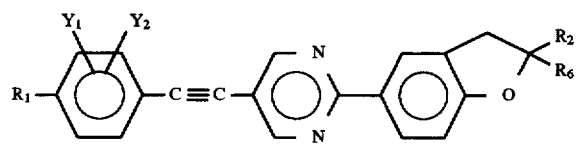 (Icc)
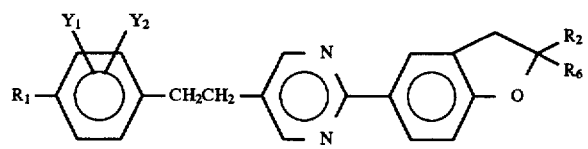 (Icd)
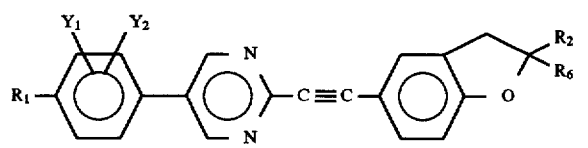 (Ice)
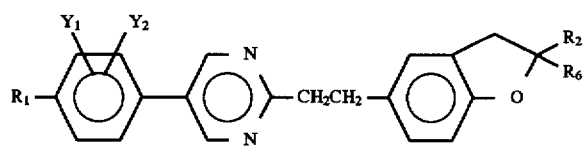 (Icf)
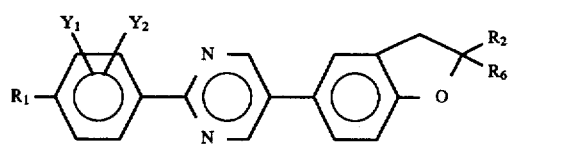 (Ida)
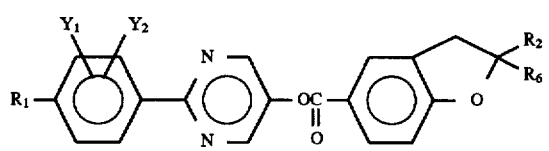 (Idb)
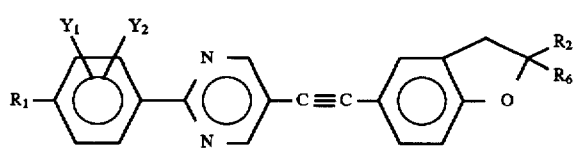 (Idc)

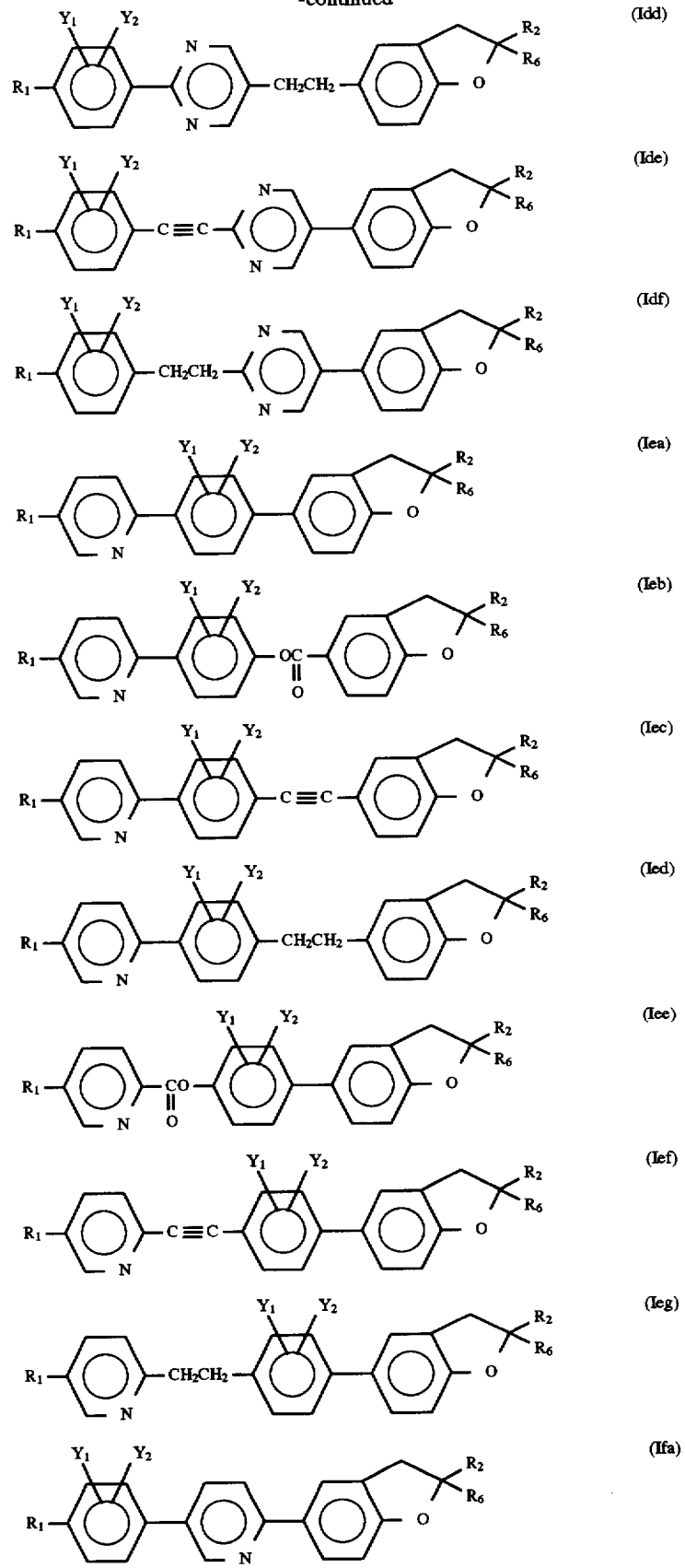

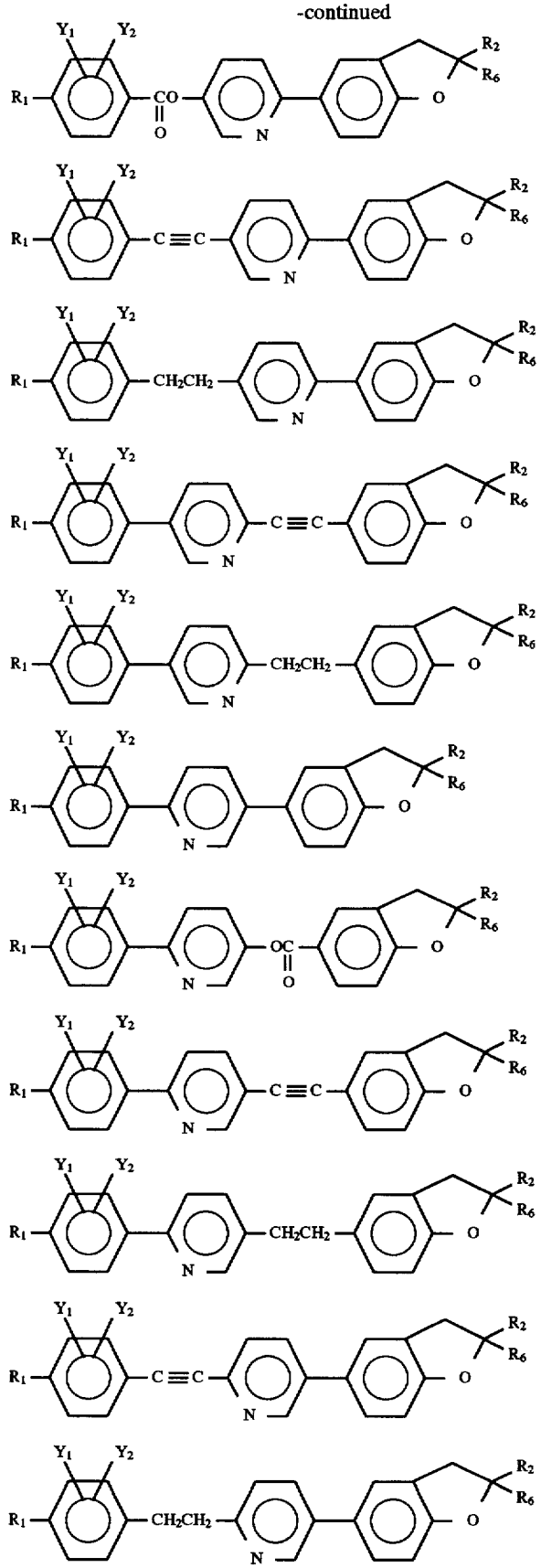

-continued
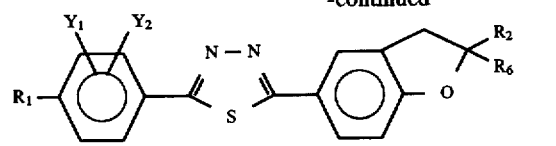 (Iha)
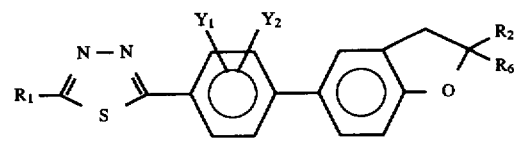 (Iia)
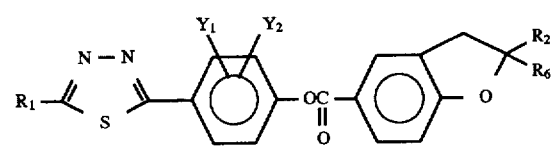 (Iib)
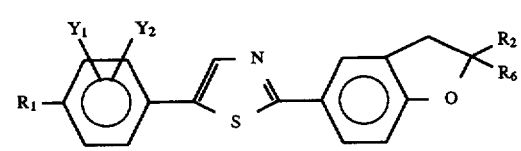 (Ija)
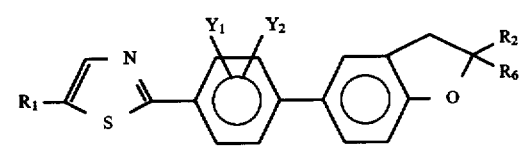 (Ika)
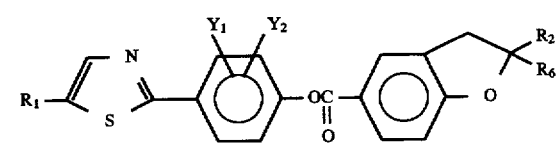 (Ikb)
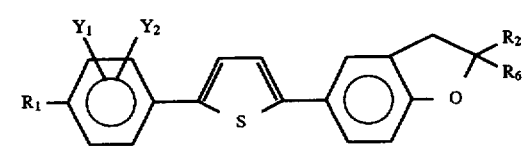 (Ila)
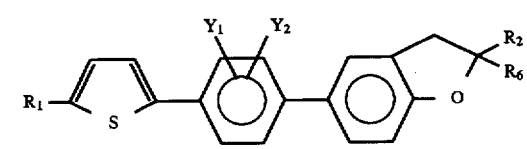 (Ima)
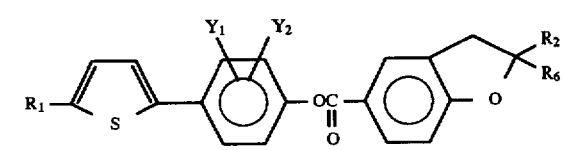 (Imb)
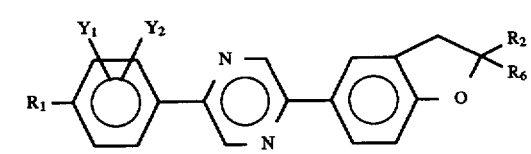 (Ina)
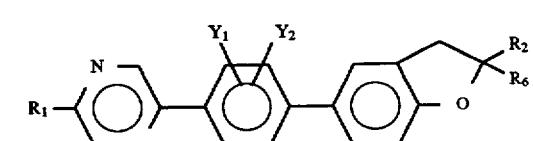 (Ioa)

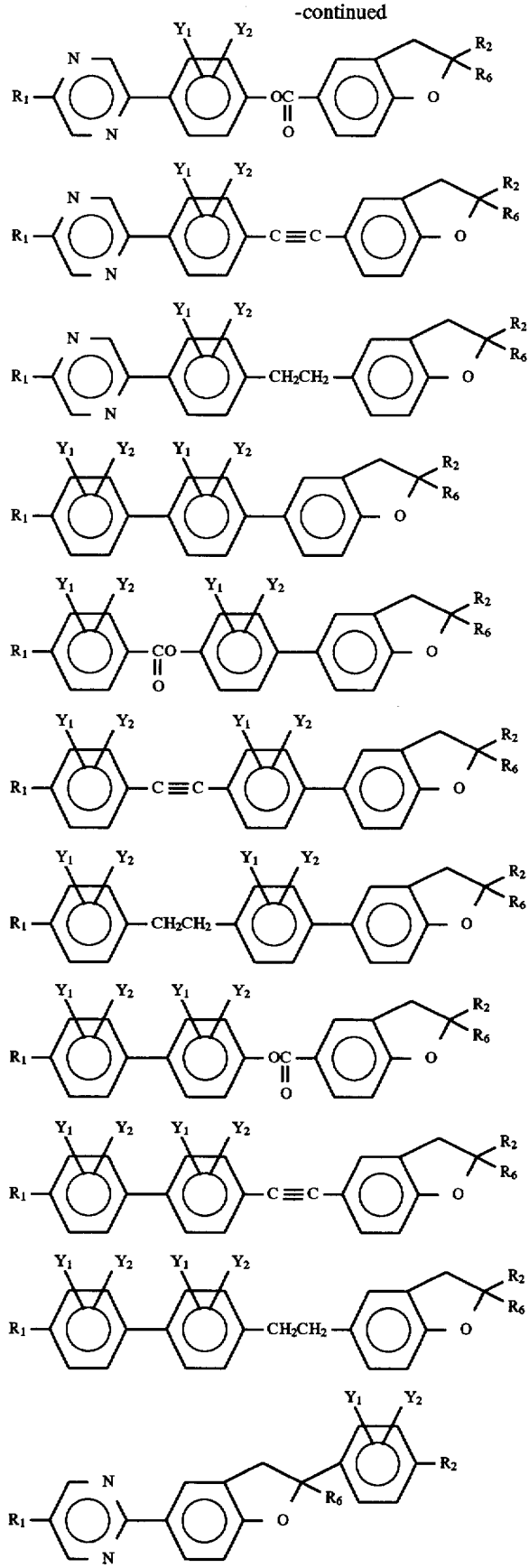

-continued
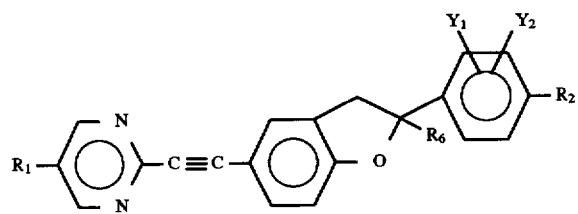 (Iqb)
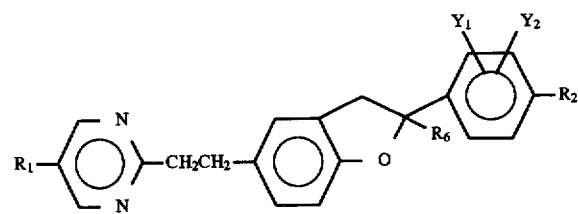 (Iqc)
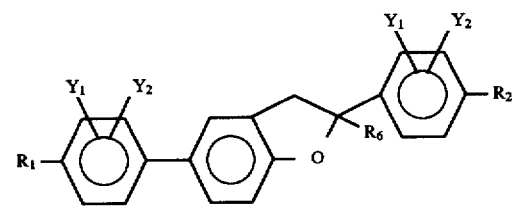 (Iqd)
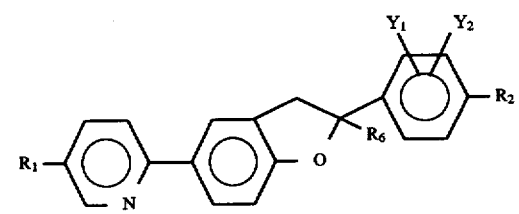 (Iqe)
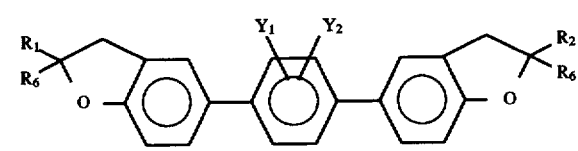 (Ira)
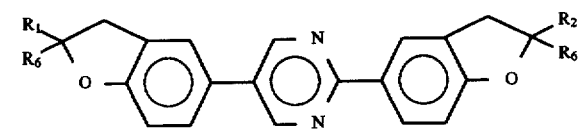 (Irb)
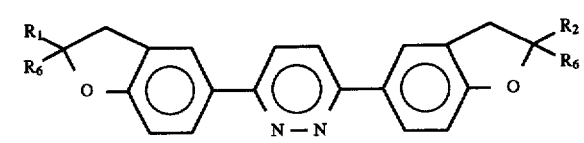 (Irc)
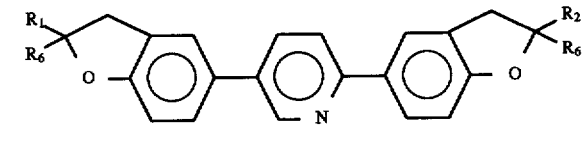 (Ird)
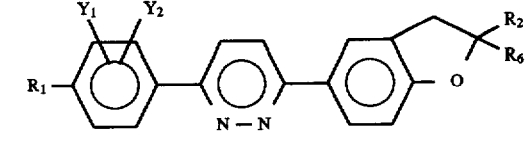 (Isa)

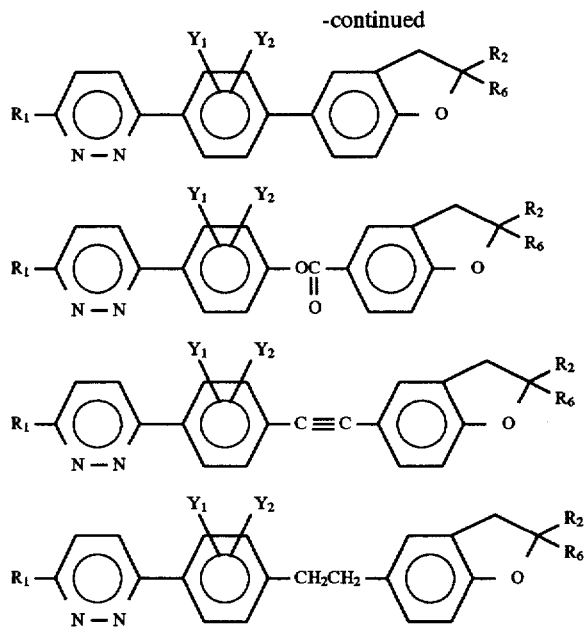

wherein $R_1$, $R_2$, $R_5$, $R_6$, $Y_1$ and $Y_2$ have the same meanings as defined in claim 1.

4. A mesomorphic compound according to claim 1, wherein $Y_1$ and $Y_2$ independently denote H, F, Cl, Br or —$CF_3$.

5. A mesomorphic compound according to claim 1, wherein $R_1$ and $R_2$ in the formula (I) are independently represented by any one of the following groups (i) to (vii):

(i) $n-C_aH_{2a+1}-X_3-$, (ii) $C_bH_{2b+1}CH(CH_3)(CH_2)_dX_3-$, (iii) $C_eH_{2e+1}O(CH_2)_fCH(CH_3)(CH_2)_gX_3-$, (iv) $C_hF_{2h+1}(CH_2)_iX_3-$, (v) $C_jH_{2j+1}CH(F)(CH_2)_kX_3-$, wherein a is an integer of 1–17; d, g and i are an integer of 0–7; b, e and h are an integer of 1–8, f and k are 0 or 1, j is an integer of 1–15; and $X_3$ denotes a single bond, —O—, $$-\underset{O}{\underset{\|}{OC}}- \text{ or } -\underset{O}{\underset{\|}{CO}}-.$$

6. A mesomorphic compound according to claim 1, wherein $R_5$ and $R_6$ in the formula (I) are hydrogen.

7. A mesomorphic compound according to claim 1, which is an optically active compound.

8. A mesomorphic compound according to claim 1, which is an optically inactive compound.

9. A compound according to claim 1, which is represented by the following formula (I-15):

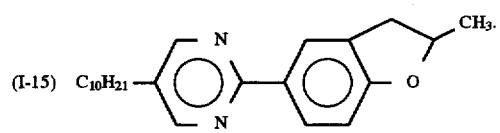

10. A compound according to claim 1, which is represented by the following formula (I-235):

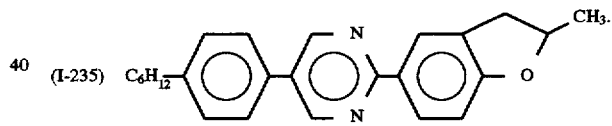

11. A compound according to claim 1, which is represented by the following formula (I-17):

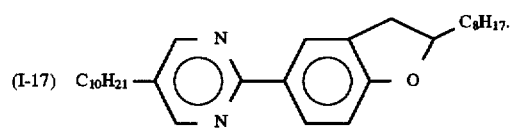

12. A compound according to claim 1, which is represented by the following formula (I-154):

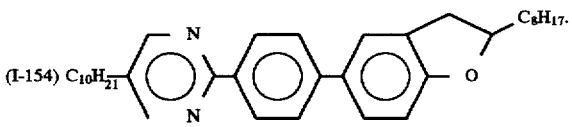

13. A compound according to claim 1, which is represented by the following formula (I-156):

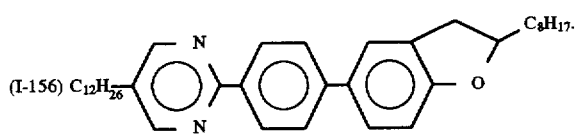

14. A compound according to claim 1, which is represented by the following formula (I-152):

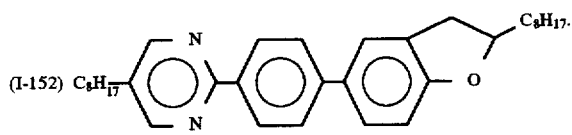

15. A compound according to claim 1, which is represented by the following formula (I-88):

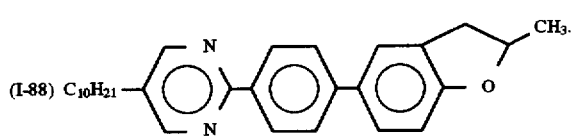

16. A compound according to claim 1, which is represented by the following formula (I-372):

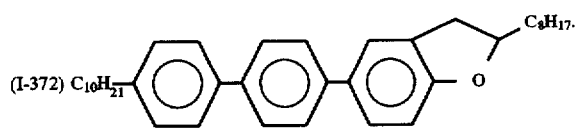

17. A compound according to claim 1, which is represented by the following formula (I-207):

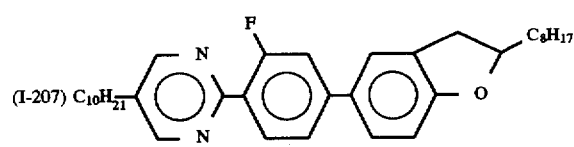

18. A compound according to claim 1, which is represented by the following formula (I-375):

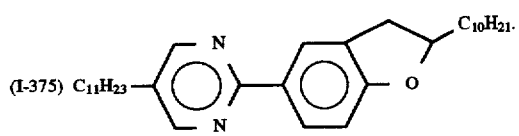

19. A liquid crystal composition comprising at least two compounds, at least one of which is a mesomorphic compound of the formula (I) according to claim 1.

20. A liquid crystal composition according to claim 19, which comprises 1–80 wt. % of a mesomorphic compound of the formula (I).

21. A liquid crystal composition according to claim 19, which comprises 1–60 wt. % of a mesomorphic compound of the formula (I).

22. A liquid crystal composition according to claim 19, which comprises 1–40 wt. % of a mesomorphic compound of the formula (I).

23. A liquid crystal composition according to claim 19, which has a chiral smectic phase.

24. A composition according to claim 19, which comprises a mesomorphic compound of the following formula (I-154):

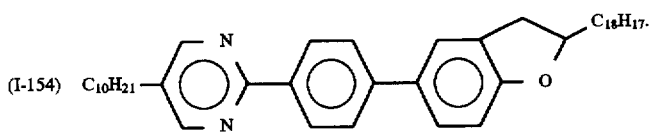

25. A composition according to claim 19, which comprises a mesomorphic compound of the following formula (I-152):

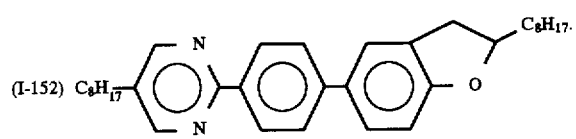

26. A composition according to claim 19, which comprises three mesomorphic compounds of the following formulae (I-18), (I-55) and (I-310):

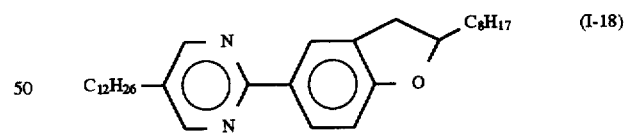

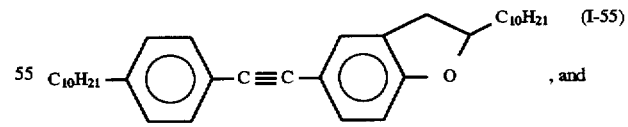

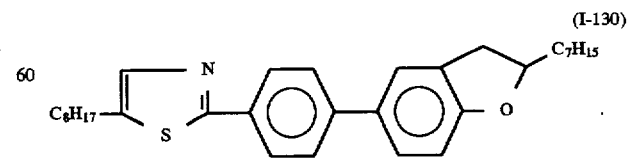

27. A composition according to claim 19, which comprises three mesomorphic compounds of the following formulae (I-8), (I-137) and (I-366):

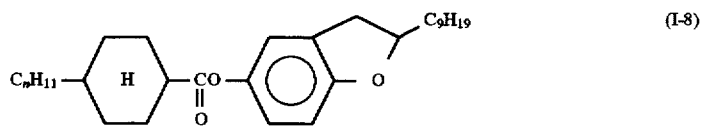
(I-8)

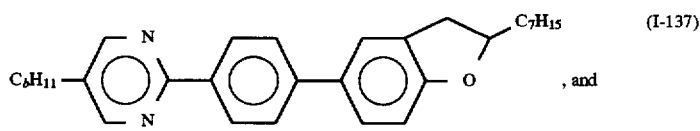
(I-137), and

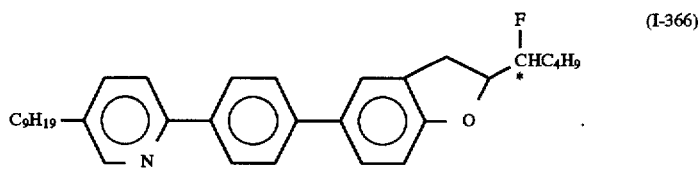
(I-366)

28. A composition according to claim 19, which comprises three mesomorphic compounds of the following formulae (I-49), (I-75) and (I-201):

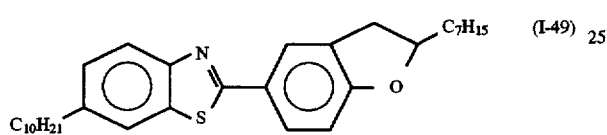
(I-49)

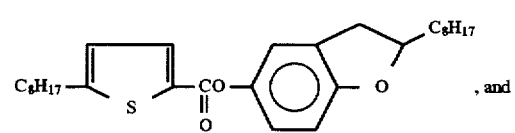
(I-75), and

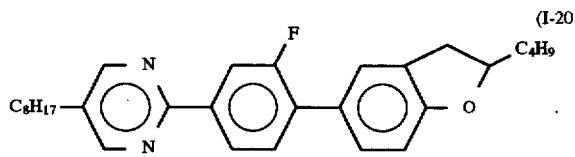
(I-201)

29. A composition according to claim 19, which comprises three mesomorphic compounds of the following formulae (I-46), (I-62) and (I-117):

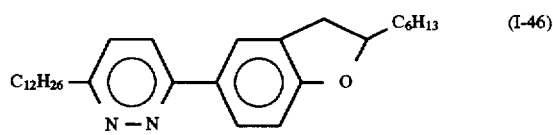
(I-46)

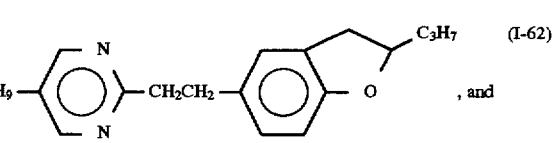
(I-62), and

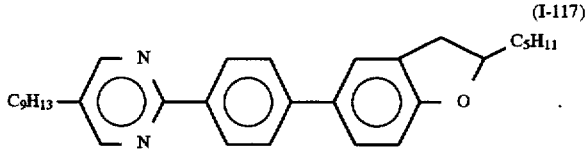
(I-117)

30. A composition according to claim 19, which comprises three mesomorphic compounds of the following formulae (I-208), (I-264) and (I-358):

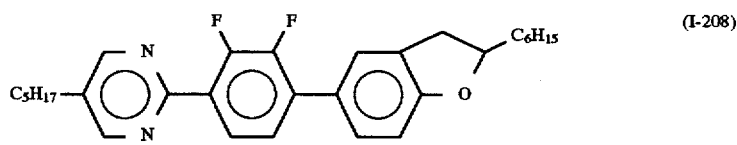
(I-208)

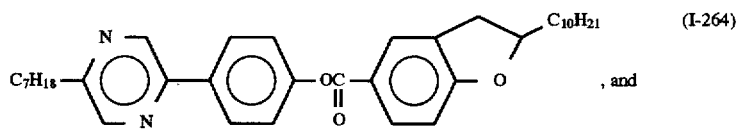
(I-264), and

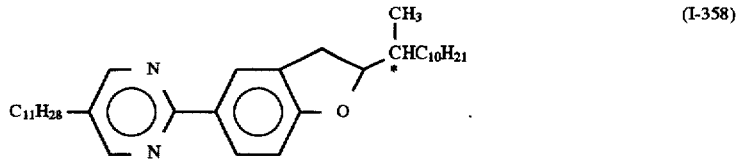
(I-358)

31. A composition according to claim 19, which comprises three mesomorphic compounds of the following formulae (I-1), (I-78) and (I-318):

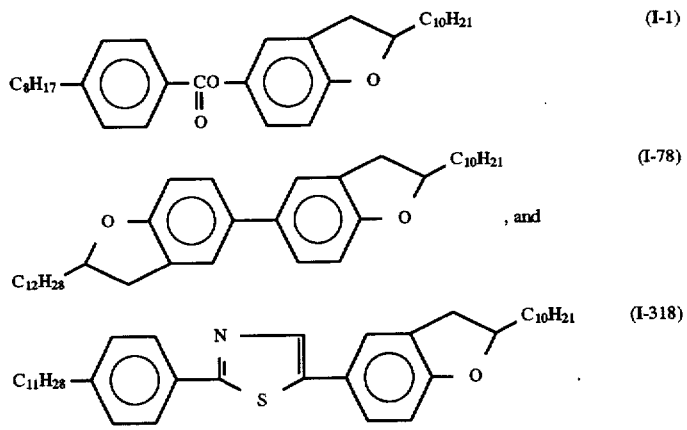

32. A composition according to claim 19, which comprises three mesomorphic compounds of the following formulae (I-25), (I-242) and (I-261):

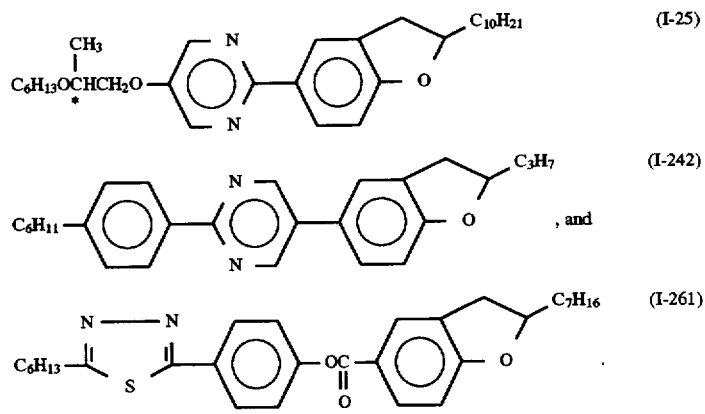

33. A composition according to claim 19, which comprises three mesomorphic compounds of the following formulae (I-51), (I-288) and (I-344):

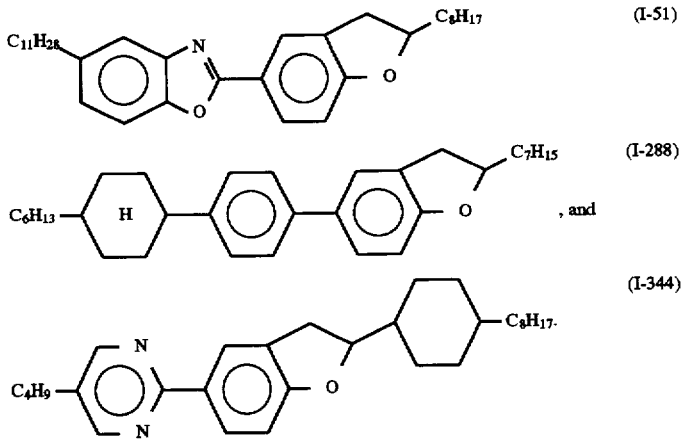

34. A liquid crystal device comprising a pair of electrode plates and a liquid crystal composition according to claim 19 disposed between the electrode plates.

35. A liquid crystal device according to claim 34, which further comprises an alignment control layer.

36. A liquid crystal device according to claim 35, wherein the alignment control layer has been subjected to rubbing.

37. A liquid crystal device according to claim 34, wherein the liquid crystal composition is disposed in a thickness suppressing formation of a helical structure of liquid crystal molecules between the electrode plates.

38. A display apparatus comprising a liquid crystal device according to claim 34, and voltage application means for driving the liquid crystal device.

39. A display apparatus according to claim 38, which further comprises a drive circuit.

40. A display apparatus according to claim 38, which further comprises a light source.

41. A display method, comprising:
providing a liquid crystal composition comprising at least two compounds, at least one of which is a mesomorphic compound of the formula (I) according to claim 1; and
switching the alignment direction of liquid crystal molecules by applying voltages to the liquid crystal composition to effect display.

42. A display method, comprising:
providing a liquid crystal composition comprising at least two compounds, at least one of which is a mesomorphic compound of the formula (I) according to claim 2; and
switching the alignment direction of liquid crystal molecules by applying voltages to the liquid crystal composition to effect display.

43. A display method, comprising:
providing a liquid crystal composition comprising at least two compounds, at least one of which is a mesomorphic compound of the formula (I) according to claim 3; and
switching the alignment direction of liquid crystal molecules by applying voltages to the liquid crystal composition to effect display.

44. A display method, comprising:
providing a liquid crystal composition comprising at least two compounds, at least one of which is a mesomorphic compound of the formula (I) according to claim 5; and
switching the alignment direction of liquid crystal molecules by applying voltages to the liquid crystal composition to effect display.

45. A display method according to claim 41, wherein $Y_1$ and $Y_2$ in the formula (I) are H, F, Cl, Br or —$CF_3$.

46. A display method according to claim 41, wherein $R_5$ and $R_6$ in the formula (I) are hydrogen.

47. A display method according to claim 41, wherein the mesomorphic compound of the formula (I) is an optically active compound.

48. A display method according to claim 41, wherein the mesomorphic compound of the formula (I) is an optically inactive compound.

49. A display method according to claim 41, wherein the liquid crystal composition comprises 1–80 wt. % of a mesomorphic compound of the formula (I).

50. A display method according to claim 41, wherein the liquid crystal composition comprises 1–60 wt. % of a mesomorphic compound of the formula (I).

51. A display method according to claim 41, wherein the liquid crystal composition comprises 1–40 wt. % of a mesomorphic compound of the formula (I).

52. A display method according to claim 41, wherein the liquid crystal composition has a chiral smectic phase.

53. A display method, comprising:
providing a liquid crystal composition according to claim 24; and
switching the alignment direction of liquid crystal molecules by applying voltages to the liquid crystal composition to effect display.

54. A display method, comprising:
providing a liquid crystal composition according to claim 25; and
switching the alignment direction of liquid crystal molecules by applying voltages to the liquid crystal composition to effect display.

55. A display method, comprising:
providing a liquid crystal composition according to claim 26; and
switching the alignment direction of liquid crystal molecules by applying voltages to the liquid crystal composition to effect display.

56. A display method, comprising:
providing a liquid crystal composition according to claim 27; and
switching the alignment direction of liquid crystal molecules by applying voltages to the liquid crystal composition to effect display.

57. A display method, comprising:
providing a liquid crystal composition according to claim 28; and
switching the alignment direction of liquid crystal molecules by applying voltages to the liquid crystal composition to effect display.

58. A display method, comprising:
providing a liquid crystal composition according to claim 29; and
switching the alignment direction of liquid crystal molecules by applying voltages to the liquid crystal composition to effect display.

59. A display method, comprising:
providing a liquid crystal composition according to claim 30; and
switching the alignment direction of liquid crystal molecules by applying voltages to the liquid crystal composition to effect display.

60. A display method, comprising:
providing a liquid crystal composition according to claim 31; and
switching the alignment direction of liquid crystal molecules by applying voltages to the liquid crystal composition to effect display.

61. A display method, comprising:
providing a liquid crystal composition according to claim 32; and
switching the alignment direction of liquid crystal molecules by applying voltages to the liquid crystal composition to effect display.

62. A display method, comprising:
providing a liquid crystal composition according to claim 33; and
switching the alignment direction of liquid crystal molecules by applying voltages to the liquid crystal composition to effect display.

63. A display method, comprising:
providing a liquid crystal device comprising a pair of electrode plates and a liquid crystal composition disposed therebetween comprising at least two compounds, at least one of which is a mesomorphic compound of the formula (I) according to claim 1; and
switching the alignment direction of liquid crystal molecules by applying voltages to the liquid crystal composition disposed between the electrode plates to effect display.

* * * * *

UNITED STATES PATENT AND TRADEMARK OFFICE
CERTIFICATE OF CORRECTION

PATENT NO. : 5,733,476
DATED : March 31, 1998
INVENTOR(S) : TAKAO TAKIGUCHI ET AL.

It is certified that error appears in the above-identified patent and that said Letters Patent is hereby corrected as shown below:

COLUMN 1

Line 30, "molecular:" should read --molecular--.

COLUMN 2

Line 47, "end" should read --and--.

COLUMN 3

Line 37, "Good" should read --good--.

COLUMN 5

Line 51, "u" should read --a--.

COLUMN 8

Line 62, "$R_3$" should read --$R_2$--; and
Line 63, "$R_0$" should read --$R_6$--.

COLUMN 9

Line 46, " 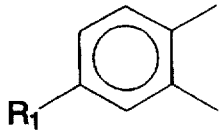 " should read -- 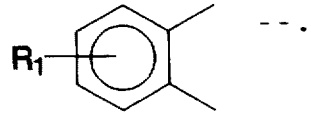 --.

COLUMN 26

Line 14, "1 and 8," should read --1-8,--; and
Line 22, "group" should read --group (i).--.

UNITED STATES PATENT AND TRADEMARK OFFICE
CERTIFICATE OF CORRECTION

PATENT NO. : 5,733,476

DATED : March 31, 1998

INVENTOR(S) : TAKAO TAKIGUCHI ET AL.

It is certified that error appears in the above-identified patent and that said Letters Patent is hereby corrected as shown below:

COLUMN 33

Line 17, "$C_0H_{13}$" should read --$C_6H_{13}$--.

COLUMN 35

Line 13, "$C_7H_{16}$" should read --$C_7H_{15}$--;
Line 24, "$C_0H_{13}$" should read --$C_6H_{13}$--;
Line 28, "$C_6H_{12}$" should read --$C_6H_{13}$--;
Line 32, "$C_{12}H_{26}$" should read --$C_{12}H_{25}$--;
Line 42, "$C_{10}H_{33}O$" should read --$C_{16}H_{33}$--; and
Line 46, "$C_7H_{16}$" should read --$C_7H_{15}$--.

COLUMN 37

Line 18, "$C_0H_{13}$" should read --$C_6H_{13}$--;
Line 21, "$C_6H_{11}$" should read --$C_5H_{11}$--; and
Line 45, "$C_7H_{16}$" should read --$C_7H_{15}$--.

COLUMN 39

Line 13, "$C_2H_6$" should read --$C_2H_5$--; and
Line 28, "$C_6H_{11}$" should read --$C_5H_{11}$--.

COLUMN 41

Line 33, "$C_8H_7$" should read --$C_3H_7$--;
Line 43, "$C_8H_{13}$" should read --$C_6H_{13}$--; and
Line 65, "$C_{10}H_{31}$" should read --$C_{10}H_{21}$--.

UNITED STATES PATENT AND TRADEMARK OFFICE
CERTIFICATE OF CORRECTION

PATENT NO. : 5,733,476
DATED : March 31, 1998
INVENTOR(S) : TAKAO TAKIGUCHI ET AL.

It is certified that error appears in the above-identified patent and that said Letters Patent is hereby corrected as shown below:

COLUMN 43

Line 10, "$C_{12}H_{20}$" should read --$C_{12}H_{25}$--;
Line 26, "$C_{16}H_{31}$" should read --$C_{15}H_{31}$--;
Line 42, "$C_{12}H_{26}$" should read --$C_{12}H_{25}$--; and
Line 58, "$C_{18}H_{27}$" should read --$C_{13}H_{27}$--.

COLUMN 45

Line 36, "$C_{12}H_{26}$" should read --$C_{12}H_{25}$--; and
Line 53, "$C_{16}H_{31}$" should read --$C_{15}H_{31}$--.

COLUMN 47

Line 9, "$C_8H_{13}$" should read --$C_6H_{13}$--;
Line 38, "$C_6H_{11}$" should read --$C_5H_{11}$--;
Line 41, "$C_{12}H_{26}$" should read --$C_{12}H_{25}$--;
Line 45, "$C_6H_{11}$" should read --$C_5H_{11}$--;
Line 51, "$C_6H_{11}$" should read --$C_5H_{11}$--; and
Line 56, "$C_5H_{13}$" should read --$C_5H_{11}$--.

COLUMN 49

Line 4, "$C_{16}H_{31}$" should read --$C_{15}H_{31}$--;
Line 15, "$C_6H_{11}$" should read --$C_5H_{11}$--;
Line 23, "$C_8H_{13}$" should read --$C_6H_{13}$--;
Line 26, "$C_7H_{16}$" should read --$C_7H_{15}$--;
Line 50, "$C_0H_{13}$" should read --$C_6H_{13}$--; and
Line 61, "$C_7H_{16}$" should read --$C_7H_{15}$--.

UNITED STATES PATENT AND TRADEMARK OFFICE
CERTIFICATE OF CORRECTION

PATENT NO. : 5,733,476
DATED : March 31, 1998
INVENTOR(S) : TAKAO TAKIGUCHI ET AL.

It is certified that error appears in the above-identified patent and that said Letters Patent is hereby corrected as shown below:

COLUMN 51

Line 1, "$C_7H_{16}$" should read --$C_7H_{15}$--;
Line 6, "$C_7H_{16}$" should read --$C_7H_{15}$--;
Line 8, "$C_8H_{13}$" should read --$C_6H_{13}$--;
Line 12, "$C_7H_{16}$" should read --$C_7H_{15}$--;
Line 17, "$C_7H_{16}$" should read --$C_7H_{15}$--;
Line 22, "$C_7H_{16}$" should read --$C_7H_{15}$--;
Line 28, "$C_7H_{16}$" should read --$C_7H_{15}$--;
Line 38, "$C_7H_{16}$" should read --$C_7H_{15}$--;
Line 43, "$C_7H_{16}$" should read --$C_7H_{15}$--; and
Line 55, "$C_7H_{16}$" should read --$C_7H_{15}$--.

COLUMN 53

Line 46, "$C_{18}H_{27}$" should read --$C_{13}H_{27}$--; and
Line 59, "$C_{16}H_{31}$" should read --$C_{15}H_{31}$--.

COLUMN 55

Line 4, "$C_6H_{11}$" should read --$C_5H_{11}$--; and
Line 35, "$C_{10}H_{31}$" should read --$C_{15}H_{31}$--.

COLUMN 57

Line 46, "$C_6H_{11}$" should read --$C_5H_{11}$--.

UNITED STATES PATENT AND TRADEMARK OFFICE
CERTIFICATE OF CORRECTION

PATENT NO. : 5,733,476
DATED : March 31, 1998
INVENTOR(S) : TAKAO TAKIGUCHI ET AL.

It is certified that error appears in the above-identified patent and that said Letters Patent is hereby corrected as shown below:

COLUMN 59

Line 6, "$C_{12}H_{26}$" should read --$C_{12}H_{25}$--;
Line 8, "$C_6H_{11}$" should read --$C_5H_{11}$--;
Line 23, "$C_{12}H_{26}$" should read --$C_{12}H_{25}$--;
Line 29, "$C_{12}H_{26}$" should read --$C_{12}H_{25}$--;
Line 34, "$C_{12}H_{26}$" should read --$C_{12}H_{25}$--; and
Line 46, "$C_7H_{16}$" should read --$C_7H_{15}$--.

COLUMN 61

Line 4, "$C_0H_{13}$" should read --$C_6H_{13}$--; and
Line 15, "$C_6H_{11}$" should read --$C_5H_{11}$--.

COLUMN 63

Line 19, "$C_8H_{13}$" should read --$C_6H_{13}$--;
Line 38, "$C_5H_{13}CHO$" should read --$C_6H_{13}CHO$--; and
Line 43, "$C_5F_{13}CHO$" should read --$C_6H_{13}CHO$--.

COLUMN 65

Line 1, "$C_2H_6$" should read --$C_2H_5$--;
Line 4, "$C_8H_{13}$" should read --$C_6H_{13}$--;
Line 12, "$C_7H_{16}$" should read --$C_7H_{15}$--;
Line 34, "$C_8H_{19}$" should read --$C_9H_{19}$--; and
Line 47, "$C_{12}H_{26}$" should read --$C_{12}H_{25}$--.

UNITED STATES PATENT AND TRADEMARK OFFICE
CERTIFICATE OF CORRECTION

PATENT NO. : 5,733,476

DATED : March 31, 1998

INVENTOR(S) : TAKAO TAKIGUCHI ET AL.

It is certified that error appears in the above-identified patent and that said Letters Patent is hereby corrected as shown below:

COLUMN 67

Line 7, "$C_7H_{16}$" should read --$C_7H_{15}$--;
Line 9, "$C_{11}H_{28}$" should read --$C_{11}H_{23}$--;
Line 44, "$C_{12}H_{26}$" should read --$C_{12}H_{25}$--; and
Line 63, "$C_6H_{11}$" should read --$C_5H_{11}$--.

COLUMN 69

Line 7, "$C_5H_{13}$" should read --$C_6H_{13}$--;
Line 55, "$C_7H_{16}$" should read --$C_7H_{15}$--; and
Line 64, "$C_7H_{16}$" should read --$C_7H_{15}$--.

COLUMN 71

Line 1, "$C_6H_{11}$" should read --$C_5H_{11}$--;
Line 12, "$C_5H_{13}$" should read --$C_6H_{13}$--;
Line 51, "$C_7H_{16}$" should read --$C_7H_{15}$--; and
Line 62, "$C_6H_{11}$" should read --$C_5H_{11}$--.

COLUMN 73

Line 15, "$C_7H_{16}$" should read --$C_7H_{15}$--; and
Line 28, "$C_7H_{13}$" should read --$C_7H_{15}$--.

COLUMN 75

Line 15, "$C_6H_{11}$" should read --$C_5H_{11}$--;
Line 31, "$C_7H_{16}$" should read --$C_7H_{15}$--;
Line 48, "$C_6H_{11}$" should read --$C_5H_{11}$--; and
Line 56, "$C_6H_{17}$" should read --$C_8H_{17}$--.

UNITED STATES PATENT AND TRADEMARK OFFICE
CERTIFICATE OF CORRECTION

PATENT NO. : 5,733,476

DATED : March 31, 1998

INVENTOR(S) : TAKAO TAKIGUCHI ET AL.

It is certified that error appears in the above-identified patent and that said Letters Patent is hereby corrected as shown below:

COLUMN 77

Line 46, "$C_7H_{16}$" should read --$C_7H_{15}$--.

COLUMN 79

Line 56, "$C_6H_{11}$" should read --$C_5H_{11}$--; and
Line 61, "$C_5H_{13}$" should read --$C_6H_{13}$--.

COLUMN 83

Line 10, "$C_6H_{11}$" should read --$C_5H_{11}$--; and
Line 33, "$C_5H_{17}$" should read --$C_8H_{17}$--.

COLUMN 85

Line 52, "$C_8H_{11}$" should read --$C_5H_{11}$--; and
Line 55, "$C_7H_{16}O$" should read --$C_7H_{15}O$--.

COLUMN 87

Line 19, "$C_2H_6$" should read --$C_2H_5$--.

COLUMN 89

Line 35, "$C_{12}H_{26}$" should read --$C_{12}H_{25}$--; and
Line 63, "$C_7H_{16}$" should read --$C_7H_{15}$--.

UNITED STATES PATENT AND TRADEMARK OFFICE
CERTIFICATE OF CORRECTION

PATENT NO. : 5,733,476
DATED : March 31, 1998
INVENTOR(S) : TAKAO TAKIGUCHI ET AL.

It is certified that error appears in the above-identified patent and that said Letters Patent is hereby corrected as shown below:

COLUMN 97

Line 30, "$CH_2O$" should read -- —$CH_2O$---.

COLUMN 99

Line 10, "$X4'$" should read --$X_4'$--.

COLUMN 101

Line 15, "$-(CH_2)_pCH-$" should read -- $-(CH_2)_p-CH-$.

COLUMN 106

Line 35, "$R_4.$" should read --$R_4'$ P (VIII)--.

COLUMN 110

Line 12, "$Z_1'$" should read --$Z_1'$ is--; and
Line 26, "$X1$" should read --$X_1'$--.

COLUMN 111

Line 12, "(XIII):" should read --(XIIf)--.

UNITED STATES PATENT AND TRADEMARK OFFICE
CERTIFICATE OF CORRECTION

PATENT NO. : 5,733,476
DATED : March 31, 1998
INVENTOR(S) : TAKAO TAKIGUCHI ET AL.

It is certified that error appears in the above-identified patent and that said Letters Patent is hereby corrected as shown below:

COLUMN 114

Line 44, "  " should read --  --; and

Line 57, "$R_6'$," should read $OR_6'$ --.

COLUMN 116

Line 14, "10" should read --$I_0$--; and
Line 15, "i" should read --1--.

COLUMN 121

Line 28, "$C_6H_{17}$" should read --$C_8H_{17}$--; and
Line 48, "0.44" should read --0.44 g--.

COLUMN 122

Line 46, "sunder" should read --under--.

COLUMN 123

Line 11, "(0.54" should read --(8.54--.

UNITED STATES PATENT AND TRADEMARK OFFICE
CERTIFICATE OF CORRECTION

PATENT NO. : 5,733,476
DATED : March 31, 1998
INVENTOR(S) : TAKAO TAKIGUCHI ET AL.

It is certified that error appears in the above-identified patent and that said Letters Patent is hereby corrected as shown below:

COLUMN 129

Line 14, "I-151" should read --I-154--.

COLUMN 130

Line 28, "gradually" should read --gradually cooled--; and
Line 44, "9,2" should read --9.2--.

COLUMN 133

Line 32, "$OC_8H_{17}$" should read --$OC_9H_{19}$--;
Line 58, "$C_6H_{11}$" should read --$C_5H_{11}$--; and
Line 65, "$C_6H_{13}$" should read --$C_7H_{15}$--.

COLUMN 135

Line 33, "$C_7H_{16}$" should read --$C_7H_{15}$--.

COLUMN 141

Line 28, "$C_6H_{11}$" should read --$C_5H_{11}$--.

COLUMN 149

Line 4, "$C_{11}H_{22}$" should read --$C_{11}H_{23}$--; and
Line 28, "states, in" should read --states. In--.

UNITED STATES PATENT AND TRADEMARK OFFICE
CERTIFICATE OF CORRECTION

PATENT NO. : 5,733,476
DATED : March 31, 1998
INVENTOR(S) : TAKAO TAKIGUCHI ET AL.

It is certified that error appears in the above-identified patent and that said Letters Patent is hereby corrected as shown below:

COLUMN 151

Line 2, "acid" should read --and--.

COLUMN 152

Line 30, "$CH_2PPh_3$-Br$^-$" should read --$CH_2\overset{\leftarrow}{P}Ph_3$-Br$^-$--.

COLUMN 153

Line 33, "denote" should read --denote —CN,--.

COLUMN 156

Line 5, " 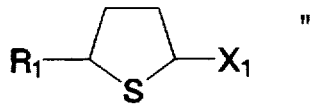 "

should read -- 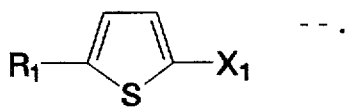 --.

COLUMN 173

Line 34, "(vii):" should read --(v):--.

COLUMN 176

Line 25, "$C_{18}H_{17}$." should read -- $C_8H_{17}$.--.

UNITED STATES PATENT AND TRADEMARK OFFICE
CERTIFICATE OF CORRECTION

PATENT NO. : 5,733,476

DATED : March 31, 1998

INVENTOR(S) : TAKAO TAKIGUCHI ET AL.

Page 12 of 12

It is certified that error appears in the above-identified patent and that said Letters Patent is hereby corrected as shown below:

COLUMN 177

Line 5, "$C_nH_{11}$" should read --$C_5H_{11}$--; and
Line 10, "$C_bH_{11}$" should read --$C_5H_{11}$--.

COLUMN 178

Line 37, "$C_9H_{13}$" should read --$C_9H_{19}$--;
Line 51, "$C_6H_{15}$" should read --$C_6H_{13}$--;
Line 57, "$C_7H_{18}$" should read --$C_7H_{15}$--; and
Line 65, "$C_{11}H_{28}$" should read --$C_{11}H_{23}$--.

COLUMN 179

Line 15, "$C_{12}H_{28}$" should read --$C_{12}H_{25}$--;
Line 19, "$C_{11}H_{28}$" should read --$C_{11}H_{23}$--;
Line 34, "$C_6H_{11}$" should read --$C_5H_{11}$--;
Line 37, "$C_7H_{16}$" should read --$C_7H_{15}$--; and
Line 50, "$C_{11}H_{28}$" should read --$C_{11}H_{23}$--.

Signed and Sealed this

Sixteenth Day of March, 1999

Attest:

*Attesting Officer*

Q. TODD DICKINSON

*Acting Commissioner of Patents and Trademarks*